(12) United States Patent
Tsiomplikas et al.

(10) Patent No.: US 11,525,783 B2
(45) Date of Patent: Dec. 13, 2022

(54) SYSTEMS, DEVICES AND METHODS FOR CELL CAPTURE AND METHODS OF MANUFACTURE THEREOF

(71) Applicant: IsoPlexis Corporation, Branford, CT (US)

(72) Inventors: Peter Tsiomplikas, Bridgeport, CT (US); Jerry Sedgewick, St. Paul, MN (US); Jeffrey Whynall, Killingworth, CT (US); Sean MacKay, New Haven, CT (US); Colin Ng, Branford, CT (US); Patrick Paczkowski, East Haven, CT (US); Sean McCusker, Pleasanton, CA (US); Igor Nikonorov, Whitestone, NY (US); Alaina Kaiser, West Haven, CT (US)

(73) Assignee: IsoPlexis Corporation, Branford, CT (US)

( * ) Notice: Subject to any disclaimer, the term of this patent is extended or adjusted under 35 U.S.C. 154(b) by 184 days.

(21) Appl. No.: 16/463,333

(22) PCT Filed: Nov. 22, 2017

(86) PCT No.: PCT/US2017/063145
§ 371 (c)(1),
(2) Date: May 22, 2019

(87) PCT Pub. No.: WO2018/098372
PCT Pub. Date: May 31, 2018

(65) Prior Publication Data
US 2019/0376898 A1    Dec. 12, 2019

Related U.S. Application Data

(60) Provisional application No. 62/569,408, filed on Oct. 6, 2017, provisional application No. 62/532,852, filed
(Continued)

(51) Int. Cl.
*G01N 21/64* (2006.01)
*B01L 3/00* (2006.01)
(Continued)

(52) U.S. Cl.
CPC .... *G01N 21/6458* (2013.01); *B01L 3/502761* (2013.01); *G01N 33/487* (2013.01);
(Continued)

(58) Field of Classification Search
None
See application file for complete search history.

(56) References Cited

U.S. PATENT DOCUMENTS

| 5,858,801 A | 1/1999 | Brizzolara |
| 6,039,897 A | 3/2000 | Lockhead et al. |

(Continued)

FOREIGN PATENT DOCUMENTS

| CN | 102690786 | 9/2012 |
| DE | 10127221 A1 | 11/2002 |

(Continued)

OTHER PUBLICATIONS

Adams et al. (2008) "Multitarget magnetic activated cell sorter", Proc Natl Acad Sci USA. , 105(47):18165-18170.
(Continued)

*Primary Examiner* — Matthew D Krcha
(74) *Attorney, Agent, or Firm* — Cooley LLP; Brian P. Hopkins; Andrew Henderson

(57) ABSTRACT

Embodiments of the current disclosure are directed to systems, methods and apparatus for evaluating single cell secretion profiles. In some embodiments, the apparatus may be configured to analyze substances expressed by a biological cell and may include a first compressible substrate, and a second substrate configured for removable sealing attachment with the first substrate. In some embodiments, upon
(Continued)

attachment of the second substrate with the first substrate, an assembly is formed such that the open side of the plurality of chambers are covered by the second substrate, and a portion of each of the plurality of capture areas are exposed in each of the chambers.

18 Claims, 43 Drawing Sheets

Related U.S. Application Data on Jul. 14, 2017, provisional application No. 62/425,502, filed on Nov. 22, 2016.

(51) Int. Cl.
*G01N 33/487* (2006.01)
*G01N 33/543* (2006.01)

(52) U.S. Cl.
CPC .... *G01N 33/543* (2013.01); *B01L 2200/0652* (2013.01); *B01L 2300/04* (2013.01); *B01L 2300/0627* (2013.01); *B01L 2300/0819* (2013.01); *B01L 2300/0851* (2013.01); *B01L 2300/0864* (2013.01); *B01L 2300/0877* (2013.01); *B01L 2300/0893* (2013.01)

(56) References Cited

U.S. PATENT DOCUMENTS

| | | |
|---|---|---|
| 6,165,739 A | 12/2000 | Clatch |
| 6,377,721 B1 | 4/2002 | Walt et al. |
| 6,429,027 B1 | 8/2002 | Chee et al. |
| 6,524,790 B1 | 2/2003 | Kopf et al. |
| 6,699,665 B1 | 3/2004 | Kim et al. |
| 6,924,153 B1 | 5/2005 | Boehringer |
| 7,312,197 B2 | 12/2007 | Gong |
| 7,381,375 B2 | 6/2008 | Ravkin et al. |
| 7,491,498 B2 | 2/2009 | Lapidus et al. |
| 7,541,444 B2 | 6/2009 | Milton et al. |
| 7,666,593 B2 | 2/2010 | Lapidus |
| 7,785,796 B2 | 8/2010 | Balasubramanian et al. |
| 8,105,845 B2 | 1/2012 | Notcovich |
| 8,236,532 B2 | 8/2012 | Ronaghi et al. |
| 8,394,590 B2 | 3/2013 | Kwong et al. |
| 8,460,878 B2 | 6/2013 | Walt et al. |
| 8,492,165 B2 | 7/2013 | Van Pelt et al. |
| 8,753,816 B2 | 6/2014 | Rigatti et al. |
| 8,802,368 B2 | 8/2014 | Lapidus |
| 9,005,929 B2 | 4/2015 | Ronaghi et al. |
| 9,051,612 B2 | 6/2015 | Zhao et al. |
| 9,121,060 B2 | 9/2015 | Milton et al. |
| 9,188,586 B2 | 11/2015 | Fan et al. |
| 9,388,464 B2 | 7/2016 | Milton et al. |
| 9,409,987 B2 | 8/2016 | Toporik et al. |
| 9,453,258 B2 | 9/2016 | Kain et al. |
| 9,506,917 B2 | 11/2016 | Fan et al. |
| 9,567,645 B2 | 2/2017 | Fan et al. |
| 9,567,646 B2 | 3/2017 | Fan et al. |
| 9,598,736 B2 | 3/2017 | Fan et al. |
| 9,701,998 B2 | 7/2017 | Hindson et al. |
| 9,727,810 B2 | 8/2017 | Fodor et al. |
| 9,765,391 B2 | 9/2017 | Swerdlow |
| 9,824,870 B1 | 11/2017 | Straume |
| 9,845,502 B2 | 12/2017 | Fodor et al. |
| 9,953,209 B2 | 4/2018 | Adalsteinsson et al. |
| 10,002,316 B2 | 6/2018 | Fodor et al. |
| 10,131,958 B1 | 11/2018 | Fan et al. |
| 10,137,426 B2 | 11/2018 | Love et al. |
| 10,151,003 B2 | 12/2018 | Fan et al. |
| 10,190,965 B2 | 1/2019 | Handigue et al. |
| 10,208,356 B1 | 2/2019 | Fan et al. |
| 10,253,375 B1 | 4/2019 | Fan et al. |
| 10,273,541 B2 | 4/2019 | Hindson et al. |
| 10,274,486 B2 | 4/2019 | Fan et al. |
| 10,337,063 B1 | 7/2019 | Brenner et al. |
| 10,378,051 B2 | 8/2019 | Meuleman et al. |
| 10,391,492 B2 | 8/2019 | Handique et al. |
| 10,391,493 B2 | 8/2019 | Handique et al. |
| 10,400,280 B2 | 9/2019 | Hindson et al. |
| 10,436,700 B1 | 10/2019 | Handique et al. |
| 10,513,731 B2 | 12/2019 | Milton et al. |
| 10,619,196 B1 | 4/2020 | Chee |
| 10,633,702 B2 | 4/2020 | Brenner et al. |
| 10,641,700 B2 | 5/2020 | Handique |
| 10,718,007 B2 | 7/2020 | Handique et al. |
| 10,676,789 B2 | 8/2020 | Hindson et al. |
| 10,746,648 B2 | 8/2020 | Handique |
| 10,752,950 B2 | 8/2020 | Hindson et al. |
| 10,774,374 B2 | 9/2020 | Frisen et al. |
| 10,793,904 B2 | 10/2020 | Swerdlow |
| 10,821,440 B2 | 11/2020 | Handique et al. |
| 10,921,237 B2 | 2/2021 | Handique |
| 10,927,419 B2 | 2/2021 | Fan et al. |
| 10,928,389 B2 | 2/2021 | Fan et al. |
| 10,941,396 B2 | 3/2021 | Fu et al. |
| 10,954,570 B2 | 3/2021 | Fan et al. |
| 11,021,749 B2 | 6/2021 | Hindson et al. |
| 11,066,689 B2 | 7/2021 | Paczkowski et al. |
| 2001/0016320 A1 | 8/2001 | He |
| 2002/0090649 A1 | 7/2002 | Chan |
| 2002/0100714 A1 | 8/2002 | Staats |
| 2002/0131974 A1 | 9/2002 | Segal |
| 2002/0146745 A1 | 10/2002 | Natan et al. |
| 2003/0013091 A1 | 1/2003 | Dmitrov |
| 2003/0082601 A1 | 5/2003 | Dill |
| 2003/0096232 A1 | 5/2003 | Kris et al. |
| 2003/0104486 A1 | 6/2003 | Selvan |
| 2003/0127610 A1 | 7/2003 | Gallagher |
| 2003/0190608 A1 | 10/2003 | Blackburb |
| 2003/0190689 A1 | 10/2003 | Crosby |
| 2004/0092032 A1 | 5/2004 | Winkler |
| 2004/0191124 A1 | 9/2004 | Noetzel |
| 2004/0224321 A1 | 11/2004 | Nicolau |
| 2004/0265889 A1 | 12/2004 | Durham |
| 2005/0032144 A1 | 2/2005 | Lombardi |
| 2005/0142033 A1 | 6/2005 | Glezer |
| 2005/0197311 A1 | 9/2005 | Cooper |
| 2005/0226779 A1 | 10/2005 | Oldham et al. |
| 2006/0246475 A1 | 11/2006 | Crosby |
| 2006/0263818 A1 | 11/2006 | Scherer |
| 2006/0286549 A1 | 12/2006 | Sohn |
| 2007/0074972 A1 | 4/2007 | Nassef |
| 2007/0122819 A1 | 5/2007 | Wu |
| 2007/0202538 A1 | 8/2007 | Glezer et al. |
| 2007/0243535 A1 | 10/2007 | Harris |
| 2008/0200343 A1 | 8/2008 | Clemens |
| 2008/0207461 A1 | 8/2008 | Ermantraut et al. |
| 2008/0317627 A1* | 12/2008 | Shirai ............... B01L 3/50273 422/52 |
| 2009/0017455 A1 | 1/2009 | Kwong |
| 2009/0053732 A1 | 2/2009 | Vermesh et al. |
| 2009/0137413 A1 | 5/2009 | Mehta et al. |
| 2009/0227043 A1 | 9/2009 | Huang |
| 2010/0009335 A1 | 1/2010 | Joseph |
| 2010/0152054 A1 | 6/2010 | Love et al. |
| 2010/0213063 A1* | 8/2010 | Zenhausern ............ G01N 1/10 204/452 |
| 2010/0279882 A1 | 11/2010 | Ronaghi et al. |
| 2010/0297145 A1 | 11/2010 | Tsujikawa et al. |
| 2011/0034908 A1 | 2/2011 | Hyde et al. |
| 2011/0048952 A1 | 3/2011 | Van Pelt et al. |
| 2011/0177537 A1 | 7/2011 | Nissum et al. |
| 2011/0224913 A1 | 9/2011 | Cui et al. |
| 2012/0015824 A1 | 1/2012 | Love et al. |
| 2012/0156675 A1 | 6/2012 | Luerssen et al. |
| 2012/0316074 A1 | 12/2012 | Saxonov |
| 2013/0274117 A1 | 10/2013 | Church et al. |
| 2013/0338047 A1 | 12/2013 | Love et al. |
| 2014/0044641 A1 | 2/2014 | Toporik et al. |
| 2014/0128281 A1* | 5/2014 | Zhang ................. B01L 3/5027 506/9 |
| 2014/0170642 A1 | 6/2014 | Huang et al. |

(56) References Cited

U.S. PATENT DOCUMENTS

| | | |
|---|---|---|
| 2015/0078999 A1 | 3/2015 | Heath et al. |
| 2015/0086424 A1 | 3/2015 | Putnam et al. |
| 2015/0204862 A1 | 7/2015 | Fan et al. |
| 2015/0204864 A1 | 7/2015 | Fan et al. |
| 2016/0129445 A1 | 5/2016 | Corey et al. |
| 2016/0160169 A1 | 6/2016 | Paczkowski et al. |
| 2016/0167049 A1 | 6/2016 | Narahara et al. |
| 2016/0238594 A1 | 8/2016 | Xue et al. |
| 2017/0067887 A1 | 3/2017 | Fan et al. |
| 2017/0138942 A1 | 5/2017 | Fan et al. |
| 2018/0105855 A1 | 4/2018 | Paczkowski et al. |
| 2018/0335419 A1 | 11/2018 | Love et al. |
| 2019/0024153 A1 | 1/2019 | Frisen et al. |
| 2019/0144936 A1 | 5/2019 | Gierahn et al. |
| 2019/0195869 A1 | 6/2019 | Fan et al. |
| 2019/0285626 A1 | 9/2019 | Ng et al. |
| 2019/0324028 A1 | 10/2019 | Fan et al. |
| 2019/0376898 A1 | 12/2019 | Tsiomplikas et al. |
| 2020/0166518 A1 | 5/2020 | Paczkowski et al. |
| 2020/0239926 A1 | 7/2020 | Paczkowski et al. |
| 2021/0388446 A1 | 12/2021 | Abate et al. |
| 2022/0017858 A1 | 1/2022 | Zheng et al. |

FOREIGN PATENT DOCUMENTS

| | | |
|---|---|---|
| EP | 1816476 A1 | 8/2007 |
| EP | 2 336 348 A1 | 6/2011 |
| EP | 3241913 A1 | 11/2017 |
| EP | 3480321 A1 | 5/2019 |
| JP | 2010-066146 | 3/2010 |
| WO | WO 96/28538 A1 | 9/1996 |
| WO | WO 02/077259 A2 | 10/2002 |
| WO | WO 2003/048736 A2 | 6/2003 |
| WO | WO 2005/007892 A1 | 1/2005 |
| WO | WO 2005/081867 A2 | 9/2005 |
| WO | WO 2005/090972 A1 | 9/2005 |
| WO | WO 2006/117541 A1 | 11/2006 |
| WO | WO 2007/014267 A2 | 2/2007 |
| WO | WO 2007/035633 A2 | 3/2007 |
| WO | WO 2008/016680 A1 | 2/2008 |
| WO | WO 2009/012340 A2 | 1/2009 |
| WO | WO 2009/012343 A1 | 1/2009 |
| WO | WO 2010/065929 A2 | 6/2010 |
| WO | WO 2010/117620 A2 | 10/2010 |
| WO | WO 2012/083225 A2 | 6/2012 |
| WO | WO 2013/090404 A2 | 6/2013 |
| WO | WO 2013/130674 A1 | 9/2013 |
| WO | WO 2013/148448 A1 | 10/2013 |
| WO | WO 2014/031997 A1 | 2/2014 |
| WO | WO 2014/052989 A2 | 4/2014 |
| WO | WO 2015/031691 | 3/2015 |
| WO | WO 2016/009446 A2 | 1/2016 |
| WO | WO 2016/057552 A1 | 4/2016 |
| WO | WO 2016/057705 A1 | 4/2016 |
| WO | WO 2016/090148 A1 | 6/2016 |
| WO | WO 2016/090320 A1 | 6/2016 |
| WO | WO 2016/118915 A1 | 7/2016 |
| WO | WO 2016/130704 A2 | 8/2016 |
| WO | WO 2016/138496 A1 | 9/2016 |
| WO | WO 2018/098372 A1 | 5/2018 |
| WO | WO 2019/213254 | 11/2019 |

OTHER PUBLICATIONS

Adler et al. (2005) "Detection of femtogram amounts of biogenic amines using self-assembled DNA-protein nanostructures," Nature Methods, 2(2):147-149.

Amir et al., (2013) "viSNE enables visualization of high dimensional single-cell data and reveals phenotypic heterogeneity of leukemia", Nat Biotechnol,, 31(6):545-52.

Anderson et al. (2002) "The human plasma proteome: history, character, and diagnostic prospects," Mol. Cell. Proteomics, 1 : 845-867.

Arenkov et al. (2000) "Protein microchips: use for immunoassays and enzymatic reactions," Anal. Biochem., 278:123-131.

Armstrong et al. (2000) "Suspension arrays for high throughput, multiplexed single nucleotide polymorphism genotyping," 40(2):102-108.

Ashton et al. (1973) "Smoking and carboxhemoglobin," Lancet. 2:857-858.

Balaban et al., (2004) "Bacterial persistence as a phenotypic switch", Science, 305(5690):1622-5.

BD Biosciences (2007) "Purified Mouse Anti-Human IL-2," Accessible on the Internet at URL:http://www.bdbiosciences.com/ptProduct.jsp?prodid=6725.

BD Pharmingen (2003) "Technical data sheet: Purified mouse anti-human IL-2 monoclonal antibody (ELISA capture)," BD Biosciences. Accessible on the Internet at URL: http://www.bdbiosciences.com/ds/pm/tds/555051.pdf.

Becker et al. (2005) "Direct readout of protein-protein interactions by mass spectrometry from protein-DNA microarrays," Angew. Chemie. Int. Ed. 44:7635-7639.

Bendall et al., (2012) "From single cells to deep phenotypes in cancer", Nat Biotechnol., 30(7):639-47.

Bendall et al., (2011) "Single-cell mass cytometry of differential immune and drug responses across a human hematopoietic continuum", Science, 332(6030):687-96.

Bernard et al. (2001) "Micromosaic immunoassays," Analytical Chemistry. 73:8-12.

Betensky et al. (2002) "Influence of unrecognized molecular heterogeneity on randomized clinical trials," J. Clin. Oncol. 20:2495-2499.

Boozer et al. (2004) "DNA directed protein immobilization on mixed ssDNA/oligo(ethylene glycol) self-assembled monolayers for sensitive biosensors," Anal. Chem. 76:6967-6972.

Boozer et al. (2006) "DNA-Directed Protein Immobilization for Simultaneous Detection of Multiple Analytes by Surface Plasmon Resonance Biosensor," Analytical Chemistry. 78:1515-1519.

Breslauer et al. (2006) "Microfluidic-based systems biology," Mol. Biosyst. 2:97-112.

Bunimovich et al. (2006) "Quantitative Real-Time Measurements of DNA Hybridization with Alkylated Nonoxidized Silicon Nanowires in Electrolyte Solution," J. Am. Chem. Soc. 128:16323-16331.

Chattopadhyay, P. et al. (2014) "Single-cell technologies for monitoring immune systems," Nature Immunology, 15(2):128-135.

Chen et al. (2002) "Discordant protein and mRNA expression in lung adenocarcinomas," Mol. Cell. Proteomics. 1:304-313.

Chen et al. (2004) "Plasma proteome of severe acute respiratory syndrome analyzed by two-dimensional gel electrophoresis and mass spectrometry," Proc. Natl. Acad. Sci. USA. 101:17039-17044.

Chen et al. (2005) "Marked Differences in Human Melanoma Antigen-Specific T Cell Responsiveness after Vaccination Using a Functional Microarray," PLoS Medicine, 2(10):1018-1030.

Chen et al., (2007) "Multiplexed analysis of glycan variation on native proteins captured by antibody microarrays", Nat Methods, 4(5):437-44.

Chen X. et al. (2012) "Microfluidic Devices Targeting Blood Cell Lysis", On-Chip Pretreatment of Whole Blood by Using MEMS Technology, p. 64-83.

Cheong et al. (2009) "Using a microfluidic device for high-content analysis of cell signaling", Sci Signal, 2(75), p. 12.

Choi et al., (2011) "Immuno-hybridization chain reaction for enhancing detection of individual cytokinesecreting human peripheral mononuclear cells", Anal Chem, 83(17):6890-5.

Chou et al. (2000) "Sorting biomolecules with microdevices," Electrophoresis. 21:81-90.

Coussens et al. (2002) "Inflammation and cancer," Nature. 420:860-867.

Crowley et al. (2005) "Isolation of plasma from whole blood using planar microfilters for lab-on-a-chip applications," Lab on a Chip, 5:922-929.

Dandy et al. (2007) "Array feature size influences nucleic acid surface capture in DNA microarrays," Proc Natl. Acad. Sci. USA, 104:8223-8228.

(56) References Cited

OTHER PUBLICATIONS

Das S. et al., (2015) "A General Synthetic Approach for Designing Epitope Targeted Macrocyclic Peptide Ligands", Angewandte Chemie, 54:13219-13224.
De Marzo et al. (2007) "Inflammation in prostate carcinogenesis," Nature Reviews Cancer. 7:256-269.
Degenaar et al. (2001) "A method for micrometer resolution patterning of primary culture neurons for SPM analysis," J. Biochem. 130:367-376.
Dehqanzada et al. (2005) "Assessing serum cytokine profiles in breast cancer patients receiving a HER2/neu vaccine using Luminex technology," Annals of Surgical Oncology, 12:S47-S48.
Delamarche et al. (1997) "Patterned delivery of immunoglobulins to surfaces using microfluidic networks," Science, 76:779-781.
Deyle, Kaycie M et al. (2015) "Protein-targeting strategy used to develop a selective inhibitor of the E17K point mutation in the PH domain of Aktl"; Nat. Chem., 7(5), p. 455-462.
Dirks et al. (2004) "Paradigms for computational nucleic acid design," Nucleic Acids Research. 32(4):1392-1403.
Downward, J., (2003) "Targeting RAS Signalling Pathways in Cancer Therapy", Nature Reviews, vol. 3, 22 pages.
Elitas, Meltem et al. (2014) "A microchip platform for interrogating the single-cell level", Lab on a Chip, vol. 14, No. 18, p. 3582.
Engvall et al. (1972) "Enzyme-linked immunosorbent assay, Elisa. 3. Quantitation of specific antibodies by enzymeabeled antiimmunoglobulin in antigen-coated tubes," J. Immunol. 109:129-135.
Erickson et al. (2003) "Modeling of DNA hybridization kinetics for spatially resolved biochips," Anal. Biochem, 317:186-200.
Eyer K. et al. (2013) "Implementing Enzyme-Linked Immunosorbent Assays on a Microfluidic Chip to Quantify Intracellular Molecules in Single Cells", Analytical Chemistry, vol. 85, No. 6, pp. 3280-3287.
Fainerman et al. (1998) "Adsorption of surfactants and proteins at fluid interfaces," Colloids and Surfaces, 143:141-165.
Fan et al., (2008) "Integrated barcode chips for rapid, multiplexed analysis of proteins in microliter quantities of blood", Nature Biotechnology, vol. 26, p. 1373-1378.
Fan et al., (2008) "Integrated blood barcode chips", Nature Biotechnology, vol. 26, No. 12, p. 1373-1378.
Fuji et al. (2005) "Clinical-scale high-throughput human plasma proteome analysis: lung adenocarcinoma," Droteomics. 5:1150-1159.
Fung (1973) "Stochastic flow in capillary blood vessels," Microvasc. Res. 5:34-38.
Galbraith, W. et al. (1993) "Remapping disparate images for conincidence", Journal of Microscopy, vol. 172, No. 2, pp. 163-176.
Gorelik et al. (2005) "Multiplexed immunobead-based cytokine profiling for early detection of ovarian cancer," Cancer Epidemiol, Biomarkers Prev. 14:981-987.
Green et al. (2006) "Capturing the uncultivated majority", Current Opinion in Biotechnology, 17(3), p. 250-255.
Groves et al. (1995) "In vitro maturation of clonal CD4+CD8+ cell lines in response to TCR engagement," J. Immunol, 154:5011-5022.
Guan et al. (2004) "Recombinant protein-based enzyme-linked immunosorbent assay and immunochromatographic tests for detection of immunoglobulin G antibodies to severe acute respiratory syndrome (SARS) coronavirus in SARS patients," Clinical and Diagnostics Laboratory Immunology, 11(2):287-291.
Hainfeld et al. (2002) "Silver and Gold-Based Autometallography of Nanogold," Ch. 3, Gold and Silver Staining, CRC Press. Washington, DC. pp. 29-46.
Han et al., (2010) "Multidimensional analysis of the frequencies and rates of cytokine secretion from single cells by quantitative microengraving", Lab Chip, 10(11):1391-400.
Han et al., (2012) "Polyfunctional responses by human T cells result from sequential release of cytokines", Proc Natl Acad Sci USA, 109(5):1607-12.
Heath et al. (2007) "Nanotechnology and cancer," Annual Review of Medicine. 59:251-265.

Henshall et al. (2007) "Assay: Validating biomarkers with VeraCode", Genet Eng Biotechnol News, 27(17):1-3.
Holland et al. (1991) "Detection of specific polymerase chain reaction product by utilizing the 5'—3' exonuclease activity of Thermus aquaticus DNA polymerase" Proc. Natl. Acad. Sci. USA. 88:7276-7280.
Hong et al. (2003) "Integrated nanoliter systems," Nature Biotechnology, 21:1179-1183.
Hong et al. (2004) "A nanoliter-scale nucleic acid processor with parallel architecture," Nature Biotechnology, 22 (4):435-439.
Hsieh et al. (2006) "Systematical evaluation of the effects of sample collection procedures on low-molecular-weight serum/plasma proteome profiling," Proteomics. 6:3189-3198.
Huang et al. (2001) "Detection of multiple proteins in an antibody-based protein microarray system," Journal of Immunological Methods. 255:1-13.
Huang et al. (2004) "Continuous particle separation through deterministic lateral displacement," Science, 304:987-990.
Huang et al. (2007) "Counting low-copy No. proteins in a single cell," Science. 315:81-84.
Huber et al. (2004) "Comparison of proteomic and genomic analyses of the human breast cancer cell line T47D and the antiestrogen-resistant derivative T47D-r," Molec. Cell. Proteomics. 3:43-55.
Hughes et al. (2003) "Molecular Monitoring of Chronic Myeloid Leukemia," Seminars in Hematology, 40(2):62-68.
Hughes, A. et al. (2014) "Single-cell western blotting", Nat Methods, 1(7):749-55.
Iannone et al. (1999) "Multiplexed single nucleotide polymorphism genotyping by oligonucleotide ligation and flow cytometry," Cytometry, 39(2):131-140.
Inerowicz et al. (2002) "Multiprotein immunoassay arrays fabricated by microcontact printing," Langmuir, 18:5263-5268.
Ivanova et al. (2002) "Polymer Microstructures Fabricated via Laser Ablatoin Used for Multianalyte Protein Microassay", Langmuir, vol. 18, p. 9539-9546.
Jeon et al. (1991) "Protein-surface interactions in the presence of polyethylene oxide: II. Effect of protein size," Journal of Colloid and Interface Science. 142(1):159-166.
Kim et al. (1979) "Establishment and characterization of BALB/c lymphoma lines with B cell properties," J. Immunol, 122:549-554.
Kiyonaka et al. (2004) "Semi-wet peptide/protein array using supramolecular hygrogel," Nature Materials. 3:58-64.
Kochenderfer et al. (2012) B-cell depletion and remissions of malignancy along with cytokine-associated toxicity in a clinical trial of anti-CD19 chimeric-antigen-receptor-transduced T-cells Blood, vol. 119, No. 12, p. 2709-2720.
Kozlov et al. (2004) "Efficient strategies for the conjugation of oligonucleotides to antibodies enabling highly sensitive protein detection," Biopolymers. 73:621-630.
Krzywinski M. et al. (2009) "Circos: An information aesthetic for comparative genomics"; Genome Res., 19, p. 1639-1645.
Kwak, M. et al. (2013) "Single-cell protein secretomic signatures as potential correlates to tumor cell lineage evolution and cell-cell interaction", Frontiers in Oncology, 3, Art. 10, p. 1-8.
Kwon et al. (2004) "Antibody arrays prepared by cutinase-mediated immobilization on self-assembled monolayers,"Anal Chem. 76:5713-5720.
Kwong et al. (2005) "Synchronous global assessment of gene and protein expression in colorectal cancer progression," Genomics. 86:142-158.
Lamb et al. (2006) "The Connectivity Map: using gene-expression signatures to connect small molecules, genes, and disease," Science. 313(5795):1929-1935.
Lambeck et al. (2007) "Serum cytokine profiling as a diagnostic and prognostic tool in ovarian cancer: a potential role or interleukin 7," Clinical Cancer Research, 13:2385-2391.
Lange et al. (2004) "Microcontact printing of DNA molecules," Analytical Chemistry. 76:1641-1647.
Lathrop (2003) "Therapeutic potential of the plasma proteome," Current Opinion in Molecular Therapeutics, 5:250-257.
Lecault et al., (2011) "High-throughput analysis of single hematopoietic stem cell proliferation in microfluidic cell culture arrays", Nat Methods, 8(7):581-586.

(56) References Cited

OTHER PUBLICATIONS

Lee et al. (2001) "SPR Imaging Measurements of 1-D and 2-D DNA Microarrays Created from Microfluidic Channels on Gold Thin Films," Analytical Chemistry, 73(22):5525-5531.

Lee et al., (2012) "Quantitative and dynamic assay of single cell chemotaxis", Integr Biol (Camb). 4(4):381-390.

Lin et al. (2005) "Evidence for the Presence of Disease-Perturbed Networks in Prostate Cancer Cells by Genomic and Droteomic Analyses: A Systems Approach to Disease," Cancer Res. 65:3081-3091.

Lin et al. (2007) "A cytokine-mediated link between innate immunity, inflammation, and cancer," Journal of Clinical Investigation, 117:1175-1183.

Liotta et al. (2003) "Protein microarrays: meeting analytical challenges for clinical applications", Cancer Cell, 3(4):317-325.

Liu et al. (2000) "Photopatterning of antibodies on biosensors," Bioconjugate Chem. 11 :755-761.

Love et al. (2006) "A microengraving method for rapid selection of single cells producing antigenspecific antibodies", Nat Biotechnol, 24(6):703-707.

Lu, Yao et al. (2013) "High-Throughout Secretomic Analysis of Single Cells to Assess Functional Cellular Heterogeneity", vol. 85, No. 4, pp. 2548-2556.

Ma, Chao et al. (2011) "A clinical microchip for evaluation of single immune cells reveals phenotypically similar T cells", Nature Medicine, vol. 17, No. 6, pp. 738-743.

MacBeath et al. (2000) "Printing proteins as microarrays for high-throughput function determination," Science, 289:1760-1763.

Madoz-Gurpide et al. (2001) "Protein based microarrays: A tool for probing the proteome of cancer cells and issues," Proteomics, 1(10):1279-1287.

Martin et al. (2006) "Molecular biology of breast cancer," Clin. Trans. Oneel. 8(1):7-14.

Mellinghoff et al. (2006) "Molecular determinants of the response of glioblastomas to EGFR kinase inhibitors," N. Engl. J. Med. 353:2012-2024.

Michel et al. (2002) "Printing meets lithography: Soft approaches to high-resolution patterning," Chimia. 56:527-542.

Michor et al. (2010) "The origins and implications of intratumor heterogeneity", Cancer Prev Res (Phila), 3(11):1361-1364.

Mischel et al. (2004) "DNA-microarray analysis of brain cancer: molecular classification for therapy," Nature Rev. Neurosci. 5:782-794.

Nagrath et al. (2007) "Isolation of rare circulating tumour cells in cancer patients by microchip technology," Nature, 450:1235-1239.

Nam et al. (2003) "Nanoparticle-based bio-bar codes for the ultrasensitive detection of proteins," Science, 301 :1884-1886.

Nam et al. (2003) "Nanoparticle-based bio-bar codes for the ultrasensitive detection of proteins," Science, 301:1884-1886,—Supporting Material pp. 1 to 12.

Nathanson et al. (2014) "Co-targeting of convergent nucleotide biosynthetic pathways for leukemia eradication", J. Exp. Med., vol. 211(3), p. 473-486.

Niemeyer (2007) "Functional devices from DNA and proteins," Nano Today, 2:42-52.

Niemeyer et al. (2005) "Immuno-PCR: high sensitivity detection of proteins by nucleic acid amplification," Trends in Biotechnology, 23:208-216.

Ostrem, J.M. et al. (2013) "K-Ras(G12C) inhibitors allosterically control GTP affinity and effector interactions", Nature, vol. 503, 14 pages.

Ottesen et al. (2006) "Microfluidic digital PCR enables multigene analysis of individual environmental bacteria," Science, 314:1464-1467.

Pal et al. (2006) "Differential Phosphoprotein Mapping in Cancer Cells Using Protein Microarrays Produced from 2-D Liquid Fractionation," Anal. Chem. 78:702-710.

Park et al. (2002) "Array-Based Electrical Detection of DNA with Nanoparticle Probes," Science. 295:1503-1506.

Peluso et al. (2003) "Optimizing antibody immobilization strategies for the construction of protein arrays," Anal. Biochem. 312:113-124.

Phillips (2004) "Rapid analysis of inflammatory cytokines in cerebrospinal fluid using chip-based immunoaffinity electrophoresis," Electrophoresis. 25:1652-1659.

Pirrung (2002) "How to make a DNA chip," Angew. Chem. Int. Ed. 41:1276-1289.

Prados et al. (2003) "Temozolomide + OS1-774," Proc. Am. Soc. Clin. Oncology, 22:99.

Prime et al. (1991) "Self-assembled organic monolayers: model systems for studying adsorption of proteins at Urfaces," Science, 252:1164-1167.

Prime et al. (1993) "Adsorption of proteins onto surfaces containing end-attached oligo(ethylene oxide): a model system using self-assembled monolayers," J. Am. Chem. Soc.115(23):10714-10721.

Quake et al. (2000) "From Micro- to Nanofabrication with Soft Materials," Science, 290:1536-1540.

Radich et al. (2006) "Gene expression changes associated with progression and response in chronic myeloid leukemia," Proc. Natl. Acad. Sci. USA, 103(8):2794-2799.

Ramsden (1995) "Puzzles and Paradox in Protein Adsorption," J. Chem. Soc. Rev. 24:73-78.

Rich et al. (2004) "Phase II trial of gefitinib in recurrent glioblastoma," J. Clin.Oncology 22:133-142.

Rowat et al., (2009) "Tracking lineages of single cells in lines using a microfluidic device", Proc Natl Acad Sci USA, 106(43):18149-54.

Sachdeva et al., (2007) "Cytokine quantitation: technologies and applications", Front Biosci. M12:4682-95, Review.

Sano et al. (1992) "Immuno-PCR: very sensitive antigen detection by means of specific antibody-DNA conjugates," Science, 258:120-122.

Sarkar A. et al. (2014) "Microfluidic probe for single-cell analysis in adherent tissue culture", Nature Communications, vol. 5, 8 pages.

Schena et al. (1995) "Quantitative monitoring of gene expression patterns with a complementary DNA microarray," Science, 270:467-470.

Schubbert, S. et al. (2007) Hyperactive Ras in developmental disorders and cancer, Nature Reviews, vol. 7, 14 pages.

Schweitzer et al. (2002) "Multiplexed protein profiling on microarrays by rolling-circle amplification," Nature Biotechnology, 20:359-365.

Sedgwick H. et al. (2008) "Lab-on-a-chip technologies for proteomic analysis from isolated cells", A Journal of the Royal Society, vol. 5, No. 2, pp. S123-S130.

Shi Q. et al. (2011) "Single-cell proteomic chip for profiling intracellular signaling pathways in single tumor cells", Proceedings National Academy of Sciences PNAS, vol. 109, No. 2, pp. 419-424.

Shin Y. et al. (2010) "Chemistries for Patterning Robust DNA MicroBarcodes Enable Multiplex Assays of Cytoplasm Proteins from Single Cancer Cells", ChemPhysChem, vol. 11, No. 14, pp. 3063-3069.

Shin et al., (2011) "Protein signaling networks from single cell fluctuations and information theory profiling", Biophys J., 100(10):2378-86.

Sia et al. (2003) "Microfluidic devices fabricated in poly(dimethylsiloxane) for biological studies," Electrophoresis, 24:3563-3576.

Soen et al. (2003) "Detection and characterization of cellular immune responses using peptide-MHC microarrays," PLoS Biology, 1 (3):429-438.

Sorger, P. (2008) "Microfluidics closes in on point-of-care assays", Nature Biotechnology, vol. 26, p. 1345-1346.

Spiro et al. (2000) "A bead-based method for multiplexed identification and quantitation of DNA sequences using flow cytometry," 66(10):4258-4265.

Svanes et al. (1968) "Variations in small blood vessel hematocrits produced in hypthermic rats by micro-occlusion," Microvascular Research, 1:210-220.

Taton et al. (2000) "Scanometric DNA array detection with nanoparticle probes," Science, 289:1757-1760.

(56) References Cited

OTHER PUBLICATIONS

Thirumalapura et al. (2005) "Lipopolysaccharide microarrays for the detection of antibodies," Journal of Immunological Methods. 298:73-81.

Thorsen et al. (2002) "Microfluidic large-scale integration," Science. 298:580-584.

Thuillier et al. (2005) "Development of a low-cost hybrid Si/PDMS multi-layered pneumatic microvalve," Microsystem Technologies. 12(1):180-185.

Tian et al. (2004) "Integrated genomic and proteomic analyses of gene expression in mammalian cells," Mol. Cell. Proteomics. 3:960-969.

Toner et al. (2005) "Blood-on-a-chip," Annual Review of Biomedical Engineering. 7:77-103.

Toure, M. et al., (2016) "Small-Molecule PROTACS: New Approaches to Protein Degradation", Angew. Chem. Int. Ed., vol. 55, 9 pages.

Unger et al., (2000) "Monolithic microfabricated valves and pumps by multilayer soft lithography", Science, 288(5463): 113-6.

Van Duijn et al. (2002) "Detection of genetically modified organisms in foods by protein-and DNA-based techniques: bridging the methods," JAOAC Int. 85(3):787-791.

Wacker (2004) "DDI-microFIA-A readily configurable microarray-fluorescence immunoassay based on DNA-direcled immobilization of proteins," Chembiochem. 5:453-459.

Wang et al., (2010) "Single cell analysis: the new frontier in 'omics'", Trends Biotechnol., 28(6):281-90.

Wei et al., (2013) "Microchip platforms for multiplex single-cell functional proteomics with applications to immunology and cancer research", Genome Med., 5(8):75.

Wegner et al. (2003) "Fabrication of Histidine-Tagged Fusion Protein Arrays for Surface Plasmon Resonance maging Studies of Protein-Protein and Protein-DNA Interactions," Analytical Chemistry, 75:4740-4746.

Whitesides et al. (2001) "Soil lithography in biology and biochemistry," Annual Review of Biomedical Engineering, 3:335-373.

Wysocki et al. (1978) "Panning for lymphocytes: a method for cell selection," Proc. Nall. Acad. Sci. USA. 75(6):2844-2848.

Yamanaka Y. J. et al. (2012) "Single-cell analysis of the dynamics and functional outcomes of interactions between human natural killer cells and target cells" Integrative Biology, vol. 4, No. 10, p. 1175-1184.

Yang et al. (2006) "A microfluidic device for continuous, real lime blood plasma separation," Lab on a Chip, 5:871-880.

Yang et al., (2007) "Using a cross-flow microfluidic chip and external crosslinking reaction for monodisperse TPP-chitosan microparticles", Sensors and Acuators, 124:510-516.

Yu et al. (2005) "Contextual interactions determine whether the Drosophila homeodomain protein, Vnd, acts as a repressor or activator," Nucleic Acids Research, 33(8):1-11.

Yu Y. et al. (2015) "Analysis of the surface, secreted, and intracellular proteome of Propionibacterium acnes", EUPA Open Proteonomics, vol. 9, pp. 1-7.

Yu J. et al. (2014) "Microfluidics-Based Single-Cell Functional Proteomics for Fundamental and Applied Biomedical Applications," Annual Review of Analytical Chemistry, vol. 7, p. 275-295.

Zhang, K. et al. (2006) "Sequencing genomes from single cells by polymerase cloning", Nature Biotechnology 24(6):680-686.

Zhao et al. (2007) "High-Affinity TCRs Generated by Phage Display Provide CD4$^+$ T Cells with the Ability to Recognize and Kill Tumor Cell Lines", The Journal of Immunology, vol. 179, No. 9, p. 5845-5854.

Zimmermann et al. (2005) "Modeling and optimization of high-sensitivity, low-volume microfluidic-based surface immunoassays," Biomedical Microdevices. 7(2):99-110.

Anonymous: "Isolight System Guide", Internet Article, 2018, pp. 1-24; Retrieved from the Internet: URL:http://isoplexis.com/wp-content/uploads/2018/04/IsoLight-User-Manual-1.pdf.

Anonymous: "Code Plex", Internet Article, 2020, pp. 1-12; Retrieved from the Internet: URL:https://offers.thescientist.com/hubfs/downloads/TS/TS_Isoplexis_2020/IsoPlexis_CodePlex_eBook/IsoPlexis_CodePlex_Ebook_final_jr_ck.pdf.

Olanrewaju et al.(2018) "Capillary microfluidics in microchannels: from microfluidic networks to capillaric circuits", Lab on a Chip, vol. 18, No. 16, pp. 2323-2347.

Shi Q. et al. "Supplementary Information: Single-Cell Proteomic Chip for Profiling Intracellular Signaling Pathways in Single Tumor Cells", Proceedings of the National Academy of Sciences of the United States of America, 2011, pp. 1-28; Retrieved from the Internet: URL:https://www.pnas.org/content/pnas/suppl/2011/12/22/1110865109.DCSupplemental/Appendix.pdf.

\* cited by examiner

Cells are dispensed into the flow cell portion of the cartridge

Cells are captured by compression of silicone

Capture agent substrate stained by washing reagents through flow cell

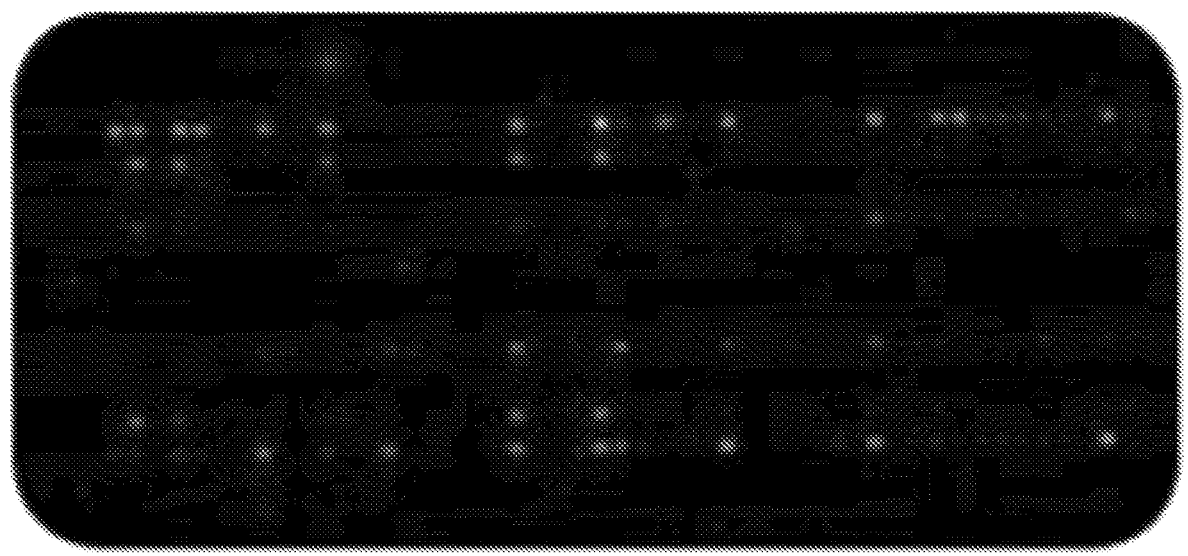
FIG. 16C
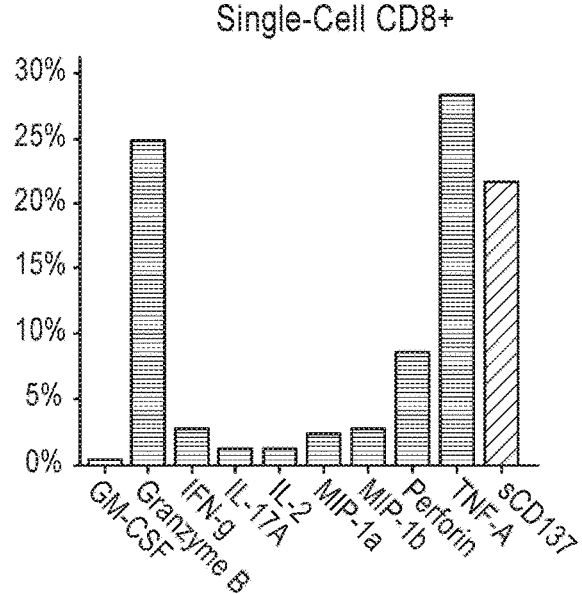
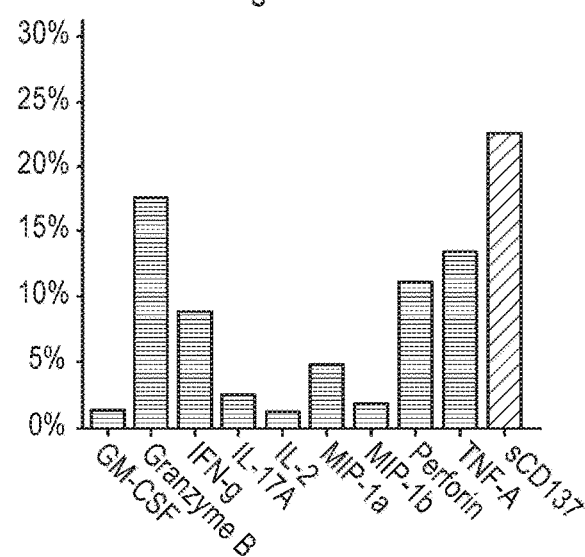
FIG. 16D  FIG. 16E

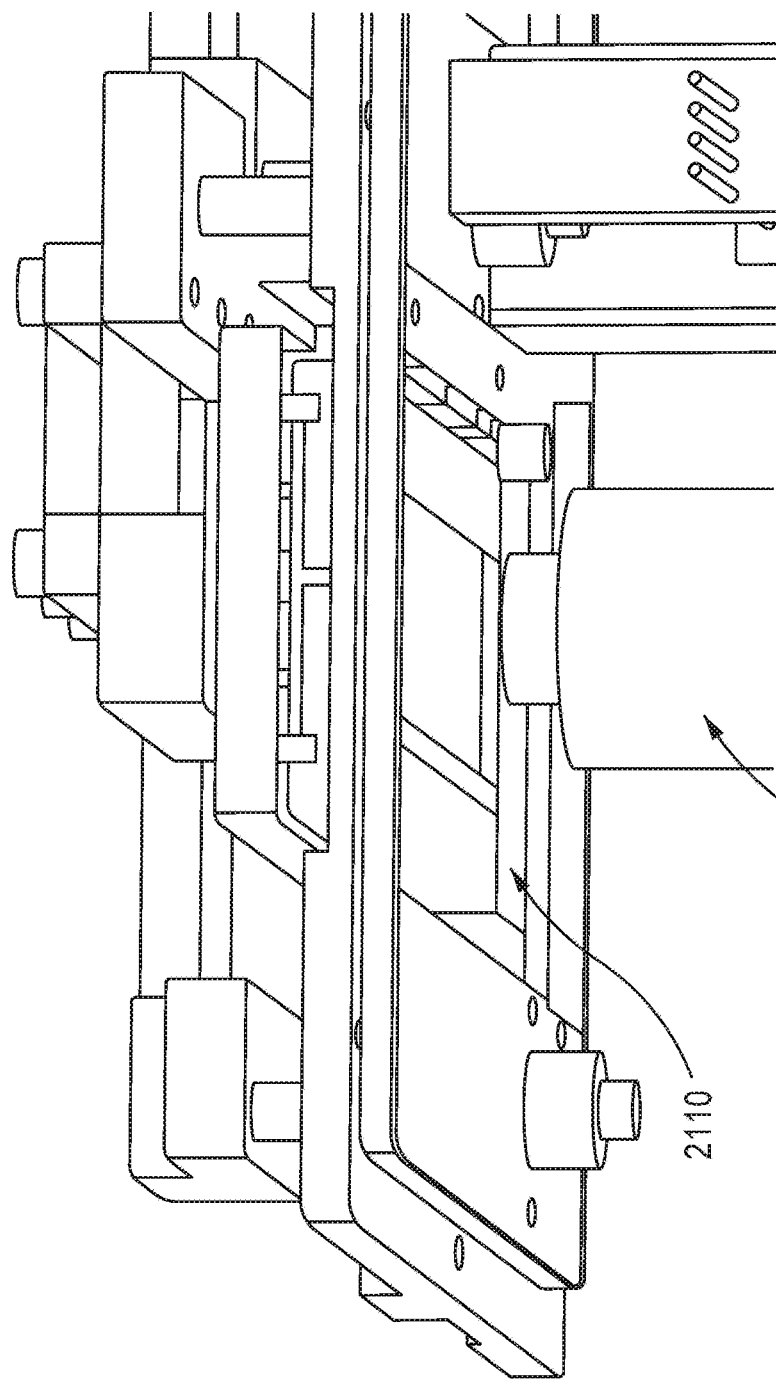

SYSTEMS, DEVICES AND METHODS FOR CELL CAPTURE AND METHODS OF MANUFACTURE THEREOF

CROSS REFERENCES TO RELATED APPLICATIONS

This application is a 35 U.S.C. § 371 national stage entry of PCT/US2017/063145, entitled "Systems, Devices and Methods for Cell Capture and Methods of Manufacture Thereof," filed Nov. 22, 2017, which claims priority to U.S. Provisional Patent Application No. 62/425,502, entitled "Systems, Devices and Methods for Positioning, Sealing, and Isolation of Single Cells and Washing of Capture Substrates for Analysis, and Methods of Manufacture Thereof," filed Nov. 22, 2016; U.S. Provisional Patent Application No. 62/532,852, entitled the same, filed Jul. 14, 2017; and U.S. Provisional Patent Application No. 62/569,408, entitled "Apparatus, Methods and Systems for Microarray Imaging of Samples," filed Oct. 6, 2017. The disclosure of each of the above applications is incorporated by reference herein in its entirety.

FIELD OF THE DISCLOSURE

Embodiments of the current disclosure are directed toward systems, methods and apparatus for evaluating single cell secretion profiles, and more particularly, systems, devices and methods for positioning, sealing, and isolating single cells and washing of capture substrates for analysis, and methods of manufacture thereof.

BACKGROUND

Reliance on methods for bulk analysis of the immune response has become a major obstacle in developing effective therapeutic treatments as these technologies are unable to evaluate the crucial cellular interactions at the single-cell level within the cellular population that dictate drug response and drug resistance. Recent investigations using single-cell analysis have shown that immune cells and cancer cells display highly heterogeneous cytokine profile even in cells with similar phenotypes further demonstrating a significant limitation of focusing only on cellular response, both cytokine and intracellular signaling protein based, at the bulk population level.

These heterogeneous subsets of cells within the population may dictate a complex signaling interplay between cells that represent important checks and balances for disease immunotherapy evaluation. This is particularly notable when a cellular population's response can be determined by the cell-cell interactions in a rare subset of cells. As result, it will be appreciated that understanding these interactions may play a crucial to developing future more effective therapeutic treatments.

Recently, efforts have been made to develop improved single cell analysis technologies to better understand the immune response. Methods for single-cell molecular profiling have revealed dynamic and bimodal gene expression. Single-cell multicolor flow cytometry and mass cytometry have also been applied to quantify phenotypic diversity and differential drug response.

A limitation exists in that these devices are unable to directly measure protein secretion in a highly multiplexed manner or analyze cell-cell interactions at the single cell level.

SUMMARY OF SOME OF THE EMBODIMENTS

Some embodiments of the present disclosure present systems, methods and devices, as well as, methods for construction and manufacture of such systems and devices, that are configured for evaluating single cell secretion profiles in a highly multiplex manner. Also disclosed are apparatus, methods and systems for properly analyzing images of samples, for producing homogenous illumination of light sources on samples, and for reducing or removing glare from light sources applied onto samples.

In some embodiments of the disclosure, an apparatus configured to analyze substances expressed by a biological cell is provided and includes a first compressible substrate comprising a length extending in a first direction, a first end and a second end separated by the length, and a width extending in a second direction, a plurality of micro-chambers having an open side and configured to receive a sample comprising a biological cell, each micro-chamber having a width extending in the second direction, a length extending in the first direction, and a depth. The apparatus further comprises a second substrate configured for removable sealing attachment with the first substrate, the second substrate including an array of approximately linear and/or parallel, isolated capture areas (CAs) extending in the second direction, each CA having a predetermined width, wherein each CA comprises a specific capture antibody. Upon attachment of the second substrate with the first substrate an assembly is formed such that the open side of the plurality of chambers are covered by the second substrate, and a portion of each of the plurality of CAs are exposed in each of the chambers.

Such embodiments may include one and/or another of the following additional features, functionalities, and/or clarifications (yielding yet further embodiments):

a compression compartment for housing the assembly, where the compression compartment can comprise compression means configured to compress the assembly;

the first substrate is secured, bonded or attached to the second substrate;

the bond is established between the second substrate and first substrate by activating corresponding mating surfaces of each substrate, where activating of mating surfaces can comprise plasma treatment;

a base of the compartment is configured with one or more features that allow easy insertion and removal of the apparatus, where the one or more features comprise a cutout;

the compression means (see above) comprises a spring, and/or a clamp;

the base can be configured with at least one shaft, the at least one shaft is configured to accurately guide a top of the compartment onto the base;

shoulder screws configured for hand manipulation by a user;

the compression ring may include one or more compression springs, where upon fully engaging the shoulder screws, the one or more compression springs provide a uniform and/or magnitude specific compression force between the second substrate and first substrate, where the magnitude specific compression force is configured to be repeatable and/or not place excessive stress on the second substrate;

one or more openings configured for providing a pathway for light;

a feature on a base of the compartment configured to enable viewing one or more CAs of the second substrate; and the second substrate comprises a glass substrate.

Some embodiments of the current disclosure may include a flowchip configured for manufacturing a capture substrate. The flowchip may comprise a substrate comprising a compressible material; a plurality of inlets; a plurality of outlets; and a plurality of flowchannels, where the substrate is configured for reversible sealing engagement against a capture substrate.

Some embodiments of the current disclosure may include a method for manufacturing a capture substrate that comprises the steps of providing a flowchip comprising a compressible substrate, the substrate including a plurality flowchannels, each flow channel including a corresponding inlet and outlet; arranging a substrate to cover and removably attached to at least the plurality of flow channels of the compressible substrate, the substrate being removably attached to the compressible substrates via negative pressure; providing a sample adjacent each inlet; and applying a negative pressure to each of the plurality of inlets such that the sample is distributed within each flow channel such that each sample is deposited on a portion of the substrate which corresponds to a respective flow channel. In some embodiments, after a predetermined period of time of applied pressure, capture areas (CAs) are formed on each portion.

In some embodiments, applying the negative pressure comprises applying a vacuum to a single tubing line attached to a pressure chamber encompassing the plurality of outlets, such that the sample is pulled, drawn, and/or distributed through the channels. The negative pressure may be configured to aid in securing and/or sealing the pressure chamber to at least a portion of the flowchip, wherein the securing and/or sealing can be at least due in part to an elastomeric property of the compressible substrate. In some embodiments, the applied pressure is applied for a predetermined period of time, which may be between about 1-4 hours.

Some embodiments of the current disclosure may include a method for manufacturing a capture substrate. In some embodiments, the method comprises the steps of providing a flowchip substrate, the substrate including a plurality flowchannels, each flow channel including a corresponding inlet and outlet; providing a sample adjacent each inlet; and arranging a substrate to cover and removably attached to at least the plurality of flow channels of the substrate. In some embodiments, respective portions of the substrate correspond to and are exposed to each flow channel, and the sample can be distributed within each flow channel and deposited on respective portions of the substrate without thermal bounding of the substrate to the flowchip substrate.

Some embodiments of the current disclosure may include a method of producing a compressible substrate having a plurality of micro-chambers. In some embodiments, the method comprises the steps of placing a housing against a mold, the mold configured to produce a compressible substrate having a plurality of micro-chambers; pouring an elastomer into the mold; curing the mold; and de-molding the substrate from the mold, wherein support features within the mold allow for efficient de-molding of the compressible substrate. In some embodiments, the mold geometry produces: chambers on the micro-chamber substrate that extend beyond a first surface of the holder such that a seal can form between the micro-chamber substrate and a capture substrate; a cavity through which reagents are flowed; and openings on each side of the micro-chamber substrate which are correspondingly configured to serve as an inlet and outlet for reagents. In some embodiments, the height of the cavity is configured to be between 20 and 200 µm.

Some embodiments of the current disclosure may include a consumable device for cell analysis. In some embodiments, the device may comprise a housing; a first micro-chamber substrate arranged within the housing, the substrate including a plurality of micro-chambers, a cavity and at least one inlet and at least one outlet; and a second capture agent substrate arranged within the housing and configured to cover the micro-chamber substrate, the second substrate comprising an array of approximately linear and parallel, spaced apart capture areas (CAs) having a predetermined width, wherein each CA comprises a specific capture antibody. In some embodiments, the housing is configured to securely seal the micro-chamber substrate against the antibody encoded slide; and the seal is configured to allow liquid to flow through the inlet to the outlet.

In some embodiments, the device may be configured for positioning, sealing, and isolation of single cells. In some embodiments, the device may further comprise a used reagent reservoir. In yet some embodiments, the device is further configured to compress the first and second substrates together.

Some embodiments of the current disclosure may include a method for analyzing one or more substances expressed by a biological cell. In some embodiments, the method comprises the step of providing the aforementioned consumable device. The method further comprises the steps of dispensing biological cells into the inlet of the first substrate; applying a negative pressure to the outlet of the device such that a single biological cell is received by each micro-chamber; trapping the single cell in a respective chamber by applying a force to at least the assembly of the first and second substrates, such that the first substrate compresses against the second substrate, wherein upon the trapped cell expressing at least one substance, the at least one substance is captured by one and/or another of the CAs of the second substrate; staining the second substrate; and imaging the stained second substrate.

Some embodiments of the current disclosure may include an instrument for analyzing one or more substances expressed by a biological cell. In some embodiments, the instrument may comprise a first area configured for receiving one or more consumables. In some embodiments, each consumable may be according to any of the aforementioned embodiments, wherein each consumable include a one-way feature configured to enable insert each consumable in a single orientation. Further, in some embodiments, a compressing means may be configured to compress at least the first and second substrates together.

Some embodiments of the current disclosure may include one and/or another of the following additional features, functionalities, and/or clarifications (yielding yet further embodiments):

the compressing means comprises a rigid member configured for guiding over a surface of the first substrate which does not include the microchambers;

the compressing means comprises a double-flexure mechanism, where the double-flexure mechanism comprises a double-leaf-spring arrangement;

an incubating means;

at least one door operable to open and close relative to an incubating area, the incubating area housing the first area and the compressing means;

a dispensing mechanism that operates to dispense biological cells and/or reagents into or proximate to respective inlets of the consumables;

an optically clear substrate which is configured such that the one or more consumables rest thereon;

an imaging device arranged to a side of the clear substrate for which the one or more consumables do not rest;

the imaging device is configured to image at least cells within the micro-chambers using bright field or fluorescence microscopy;

a plurality of lights arranged around the imaging device and configured to provide a bright field-type illumination, where the plurality of lights comprise a xenon lamp, the xenon lamp may be arranged such that it is guided through tubing to a phototube, the phototube including a plurality of multiband filters configured to enable imaging stained cells and/or substance signals of the antibody encoded substrates after incubation;

a multi-axis means configured to enable imaging of a plurality of consumables.

Some embodiments of the current disclosure may include an instrument for analyzing one or more substances expressed by a biological cell. In some embodiments, the instrument may comprise a housing; a user interface; a first area configured for receiving one or more consumables, each consumable being according to any of the aforementioned embodiments, where each consumable include a one-way feature configured to enable insert each consumable in a single orientation; a compressing means configured to compress at least the first and second substrates together; an incubating means; at least one door operable to open and close relative to an incubating area, the incubating area housing the first area and the compressing means; a dispensing mechanism operate to dispense biological cells and/or reagents into or proximate to respective inlets of the consumables; an optically clear substrate which is configured such that the one or more consumables rest thereon; an imaging device arranged to a side of the clear substrate for which the one or more consumables to not rest; and a plurality of lights arranged around the imaging device and configured to provide a bright field-type illumination.

Some embodiments of the current disclosure may include an apparatus, methods and systems for microarray imaging of samples. In some embodiments, a biological sample image analysis method comprises the step of receiving image data corresponding to digital information for at least one color image of a biological sample contained in a microarray. In some embodiments, the image data corresponds to red, green and blue (RGB) channels, each channel including a plurality of grayscale tones of varying intensity. The method further includes the steps of storing the image data and selecting a color model of a plurality of color models, each color model configured to control grayscale intensities for one and/or another of the RGB channels; wherein selection of the color model is based on at least one of: boosting brightness of one or more specific colors in the image data, and reducing brightness of one or more specific colors in the image data. The method also includes the step of de-mosaicizing the image data based on the color model, wherein de-mosaicizing includes: applying the color model to one or more of the color channels of the image data, such that, image data corresponding to the brightness of the one or more specific colors is boosted and/or reduced to produce enhanced image data. In some embodiments, the method further includes the steps of analyzing the enhanced image date for the presence of one or more predetermined colors; and outputting resultant data corresponding to the presence of one or more predetermined colors.

Some embodiments of the present disclosure also include a system for analyzing a biological sample comprising: a computer processor having computer instructions operating thereon such as to cause the processor to perform the above-noted method steps of biological image analysis.

In some embodiments, a system for a biological analysis illumination is disclosed. Such a system may comprise a laser configured to provide a coherent beam of light; a diffusion disk configured to rotate at a predetermined speed, and to receive the coherent beam of light; and reflection means, wherein: the diffusion disc is rotated at the predetermined speed such that the disc produces a homogenized beam of light from the received coherent beam of light, and the homogenized beam of light is received and reflected from the reflection means such that the homogenized beam of light is projected onto a glass structure configured to support a biological specimen.

In some embodiments, the biological analysis illumination system further comprises a motor configured to power a rotation of the diffusion disk. In some embodiments, the speed of the rotation of the diffusion disk can exceed about 50 rpm. Further, the system may include a diffusion filter configured to remove non-uniform patterns in one or more of the coherent beam of light and the homogenized beam of light. In some embodiments, the diffusion filter can include a glass configured for blurring one or more of the coherent beam of light and the homogenized beam of light.

In some embodiments, a method for illuminating a biological sample on a glass structure is disclosed. The method may comprise the steps of providing a laser configured to provide a coherent beam of light, a diffusion disk configured to rotate at a predetermined speed, and to receive the coherent beam of light, and reflection means; generating a coherent beam of light via the laser; rotating the diffusion disc at a predetermined speed such that the disc produces a homogenized beam of light from the received coherent beam of light, and directing the homogenized beam of light at the reflection means such that the homogenized beam of light is projected onto a glass structure configured to support a biological specimen.

In some embodiments, a widefield compound microscope (WCM) comprising: a glass substrate configured to hold a sample for imaging; a first optics means comprising an objective lens and an aperture is disclosed. In some embodiments, the WCM may optionally include an imaging device; and a second optics means comprising a set of lenses, wherein: the first optics means is arranged between the glass substrate and the aperture; and the second optics means is arranged between the imaging device and the aperture.

In some embodiments, the aperture of the WCM may be fixed in size. In some embodiments, it may be configured for adjustment in size. In some embodiments, the aperture can be arranged downstream from the objective lens towards the imaging device. In some embodiments, the WCM includes a single aperture. In some embodiments, the WCM may not include a mirror. For example, the WCM may not include a dichroic mirror. In some embodiments, the first optics means of the WCM may be configured to at least one of focus light upon the sample and focus light from a light source.

In some embodiments, the aperture of the WCM is configured to remove glare when imaging. Further, the WCM comprises a light source selected from the group consisting of a laser and a widefield light(s). In some embodiments, the aperture may be configured to position light from the light source in a path prior to entry into the first optics means.

In some embodiments, a method for projecting light from a light source onto a sample in a widefield compound microscope (WCM) is disclosed. The method may comprise the steps of providing a light source; arranging a first optics means comprising an objective lens between a glass substrate configured to hold a sample for examination and an aperture; and arranging a second optics means between the light source and the aperture, wherein light from the light source is at least one of focus light from the light source and focus light upon the sample.

BRIEF DESCRIPTION OF THE DRAWINGS

FIGS. 4A-B are example diagrams illustrating the flow of single cell suspension through the cartridge assembly, according to some embodiments. FIGS. 4C-D are example diagrams illustrating the compression of silicone to isolate single cell suspension within the microchambers, according to some embodiments. FIG. 4E is an example diagram illustrating the scanning of the microchambers to identify microchambers containing only one cell, according to some embodiments. FIG. 4F is an example diagram illustrating that the microchambers containing no cells or at least two cells are disregarded (shown as black stripes), according to some embodiments. FIG. 4G is a diagram illustrating that incubated cells secrete proteins which bond to antibody barcode arrays for identification, according to some embodiments. FIG. 4H is an example image of the cartridge assembly with fluorescent proteins, according to some embodiments.

FIGS. 16A-E are diagrams illustrating testing a prototype cartridge, according to some embodiments.

FIG. 21 is a diagram illustrating optical components that can take images of a capture agent substrate and a microchamber substrate, according to some embodiments.

FIG. 25B shows an example specific implementation of the noted use of model, according to some embodiments.

DETAILED DESCRIPTION OF SOME OF THE EMBODIMENTS

Figures 1A, 1B, 1C:
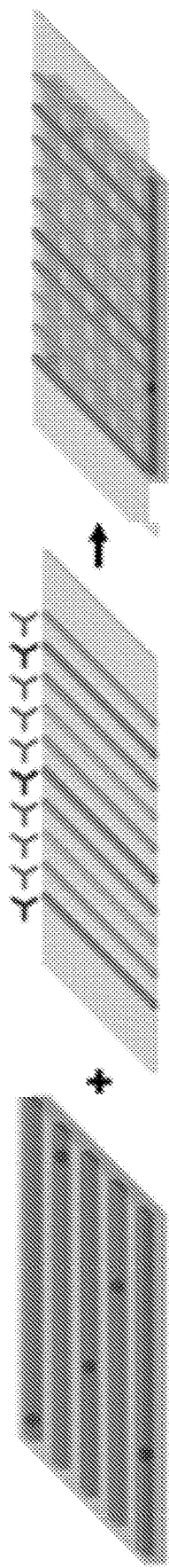
FIGS. 1A-C are diagrams illustrating an example single-cell barcode chip (SCBC) comprising a single cell microchamber array and an antibody barcode array slide, according to some embodiments.

FIGS. 1A-C are diagrams illustrating an example single-cell barcode chip (SCBC) comprising a single cell microchamber array and an antibody barcode array slide, according to some embodiments. For example, FIG. 1A-B shows a single-cell barcode chip (SCBC) comprising two parts: an antibody barcode array (e.g., FIG. 1B), and a sub-nanoliter microchamber array chip (FIG. 1A). The antibody barcode array (herein called a "capture agent substrate" or an "antibody-encoded slide") can be patterned in the parallel line fashion on a poly-amine-functionalized glass slide. The width of each line/bar of the antibody feature can be about 5-50 µm, about 10-40 µm, about 15-35 µm, about 20-30 µm, including values and subranges therebetween. In some embodiments, each line/bar of the antibody feature can be about 10 µm, 15 µm, 20 µm, 25 µm, or 30 µm in width. The sub-nanoliter microchamber array chip (herein called "silicone," "microchamber substrate," or "microchamber array") can be fabricated in polydimethylsiloxane, and can include a large number of microchambers per chip (e.g., in the range from about 1000 to about 15000, from about 5000 to about 15000, from about 10000 to about 15000, from about 11000 to about 13000, including values and subranges therebetween), each microchamber comprising a range of sizes (e.g., width and depth in the range from about 10 µm to about 30 µm, from about 15 µm to about 25 µm, including values and subranges therebetween, and the length being in the range from about 1800 µm to about 2400 µm, from about 2000 µm to about 2200 µm, including values and subranges therebetween). For example, the microchamber array chip can include about 12000 microchambers per chip, each microchamber having the dimensions of about 20 uM (width)×2060 uM (length)×20 uM (depth), for a total volume of ~1.2 nL per chamber.

Cells can be dispensed onto this microchamber substrate and can be isolated and trapped when the capture agent substrate is placed against the microchamber substrate. Each microchamber can be exposed to a full set of 2 or more capture antibody lines/bars and can permit co-detection of a panel of secreted proteins. In some embodiments, the number of capture antibody lines/bars can be in the range from about 2 to about 200, from about 2 to about 100, from about 20 to about 100, from about 20 to about 50, including values and subranges therebetween. In some embodiments, the number of capture antibody lines/bars can be up to 45. Spectral encoding (e.g., 1 color, 2 colors, 3 colors, or more) and spatial encoding (e.g., 1-100 bars (such as 15 bars, for example)) can be combined in each microchamber to achieve a very high, even unprecedented, degree of multiplexing (e.g., 45-plex including 42 proteins and 3 positive controls) for single-cell protein secretion assay. In some embodiments, the degree of multiplexing can be determined by the number of colors times the number of antibody bars. A representative scanned image can show the co-detection of 42 proteins using 15 bars/spots and 3 colors (blue, green, red), e.g., FIG. 1C. Apparatuses and methods described herein can count the number of cells in each microchamber, e.g., using software to analyze the bright field images of the whole device. The fluorescence intensity (protein signal) of all the bars in every microchamber can be quantified using a microarray scanner. Combining these two sets of data (cell counting and protein signal) and selecting for single-cell microchambers can yield a data sheet, each row of which can be a single cell (typically greater than 1000 single cells per device) and each column of which is a protein of interest. A single-cell cytokine profile can be analyzed by the software.

Figure 2A:
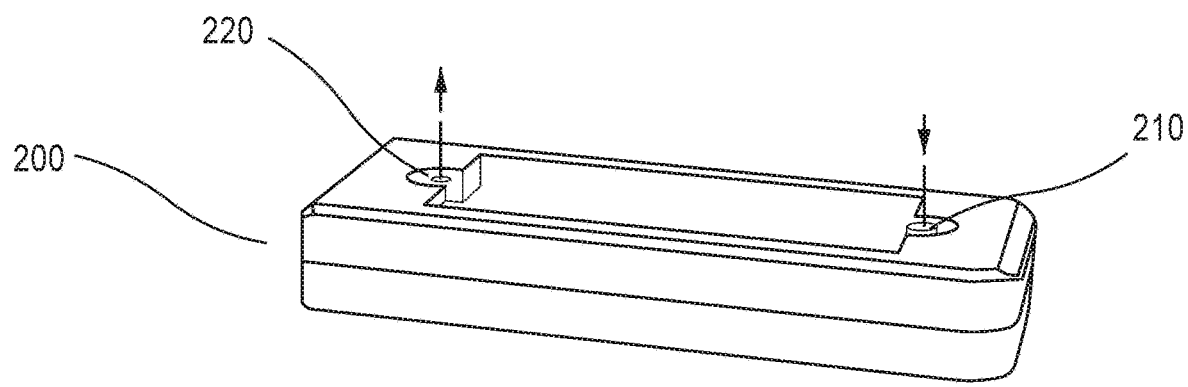
FIGS. 2A-B are diagrams illustrating an example cartridge assembly for encasing an SCBC, according to some embodiments.
Figure 2B:
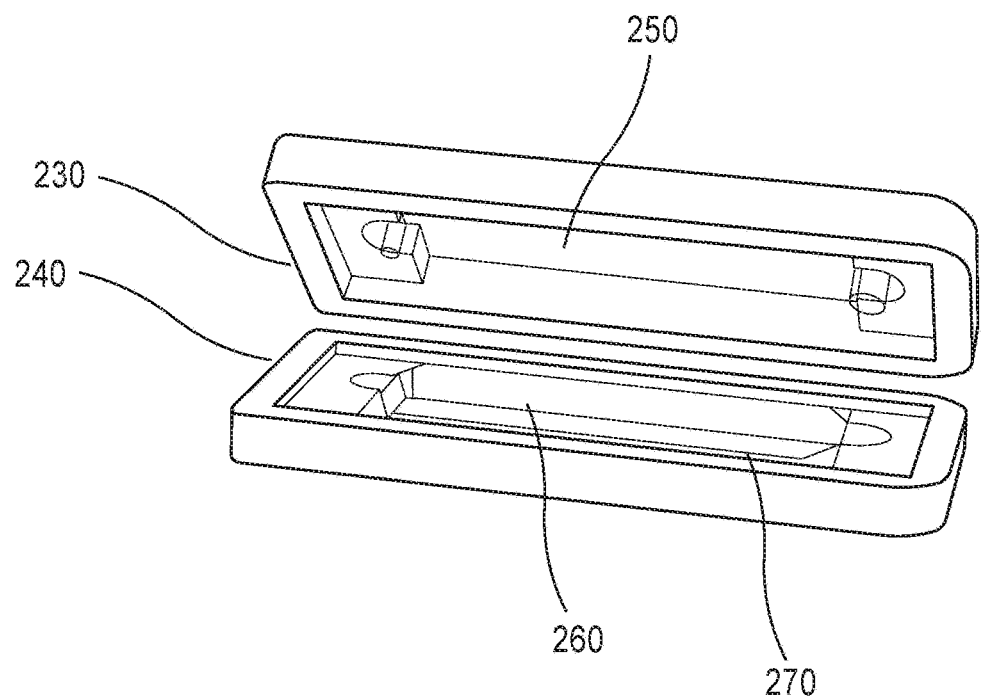

FIGS. 2A-B show diagrams illustrating an example cartridge assembly for encasing an SCBC, according to some embodiments. In some embodiments, the cartridge assembly 200 includes an inlet orifice 210 and an outlet orifice 220 for facilitating the flow of single cell suspension through the cartridge assembly 200 (FIG. 2A). In some embodiments, the diameter of the inlet and outlet orifices may be about 0.028" (0.71 mm). FIG. 2B shows a detailed view of the cartridge assembly including the silicone (i.e., microchamber array chip) 250 in one side of the cartridge assembly 200 (e.g., top side 230) and the glass slide (i.e., antibody barcode array) 260 in the other side of the cartridge assembly 200 (e.g., top side 240). In some embodiments, one or both of the silicone 250 and the glass slide 260 may be transparent. In some embodiments, the cartridge assembly 200 may include a gasket 270 (e.g., a double-sided tape) that is configured to create or facilitate a flow path between the silicone 250 and the glass slide 260.

Figure 2C:
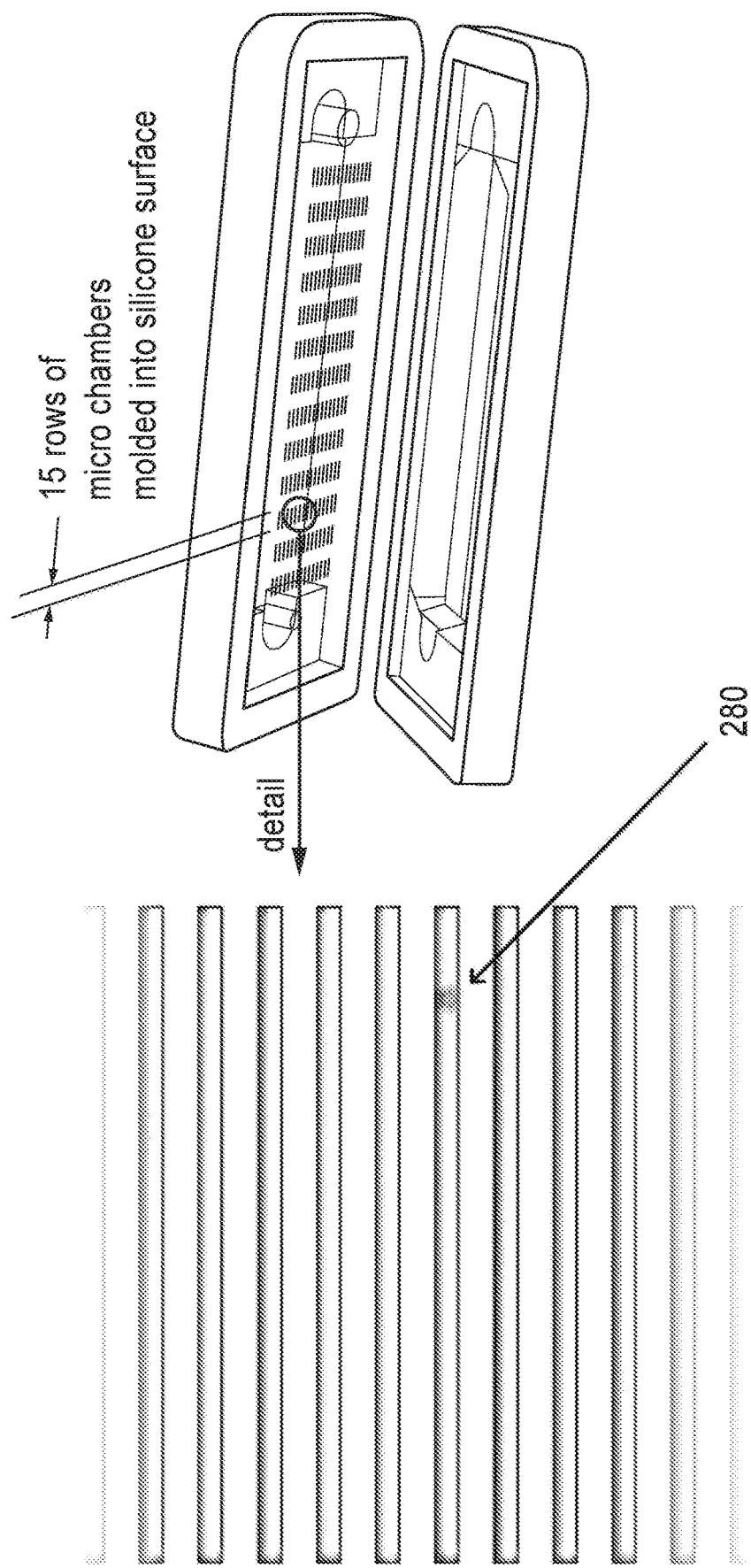
FIG. 2C is a diagram illustrating an example cartridge assembly containing a plurality of microchambers molded into a silicone surface, according to some embodiments.
Figure 2D:
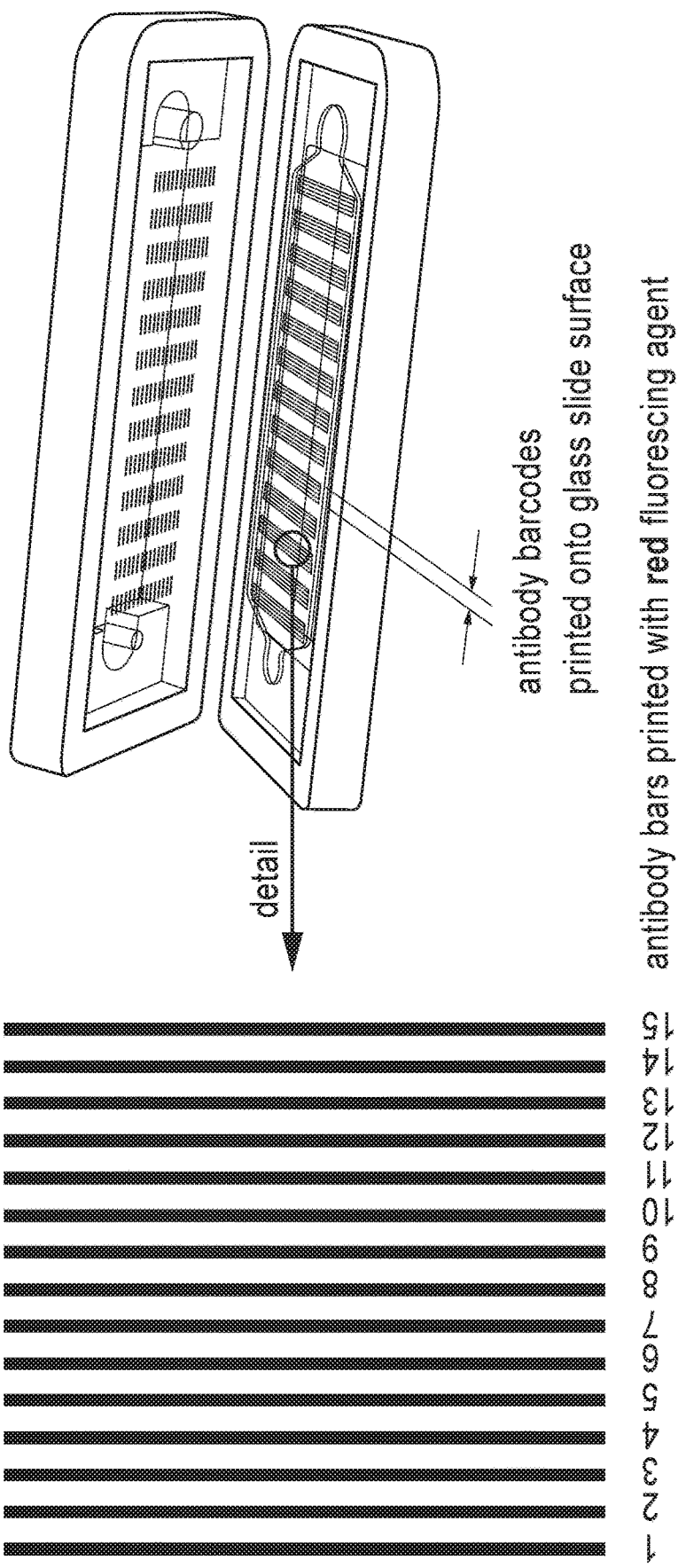
FIGS. 2D-F are example diagrams illustrating one, two and three antibody barcode arrays printed onto a glass slide surface, respectively, according to some embodiments.
Figure 2E:
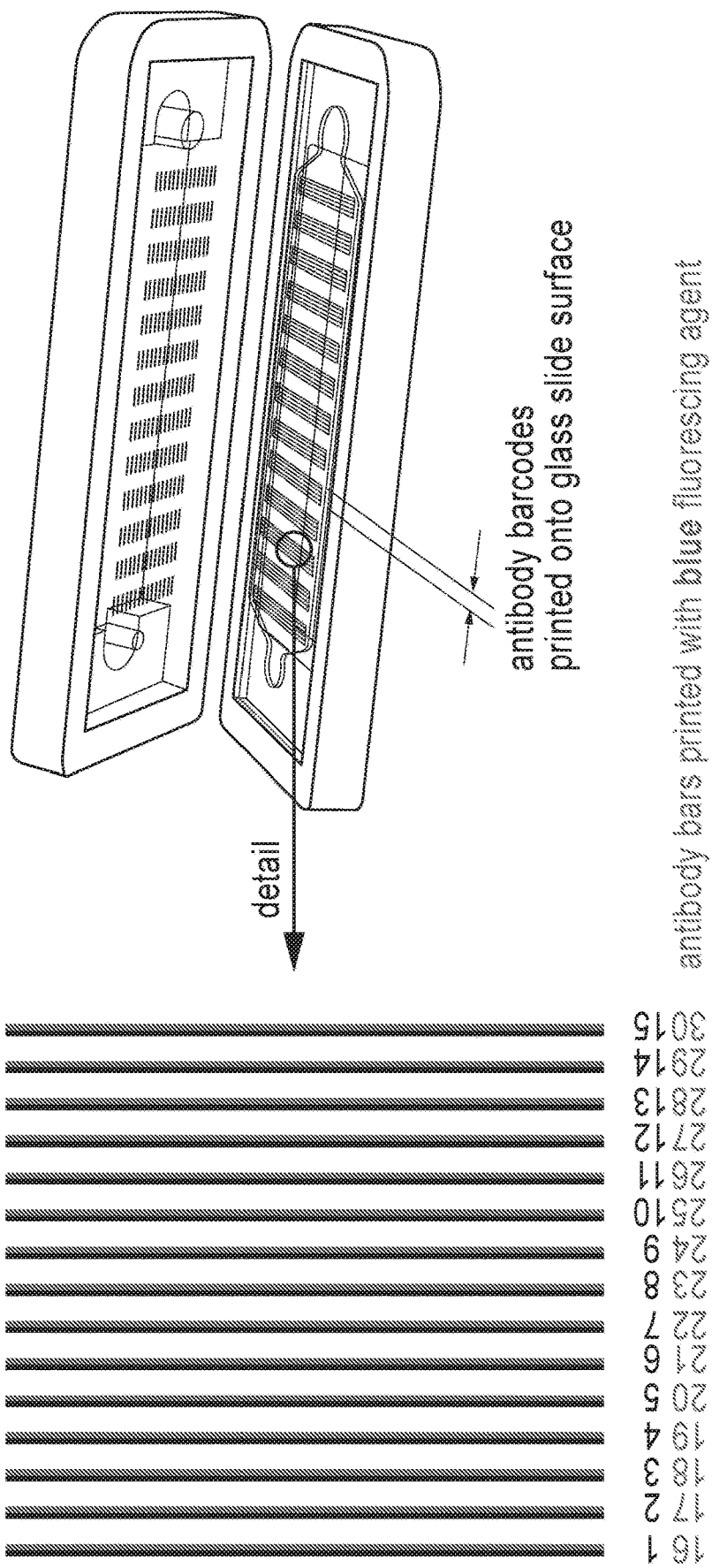
Figure 2F:
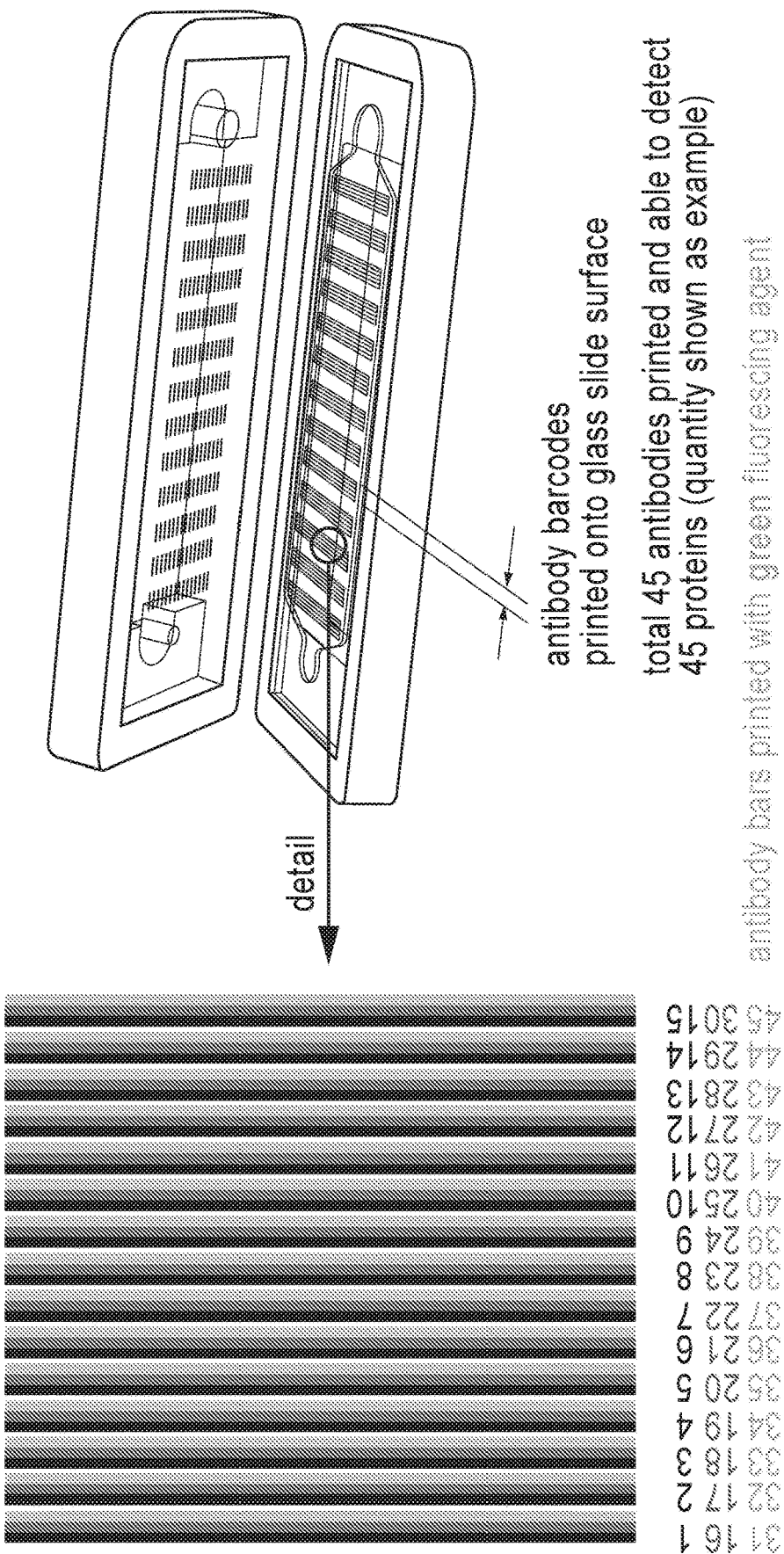
Figure 2G:
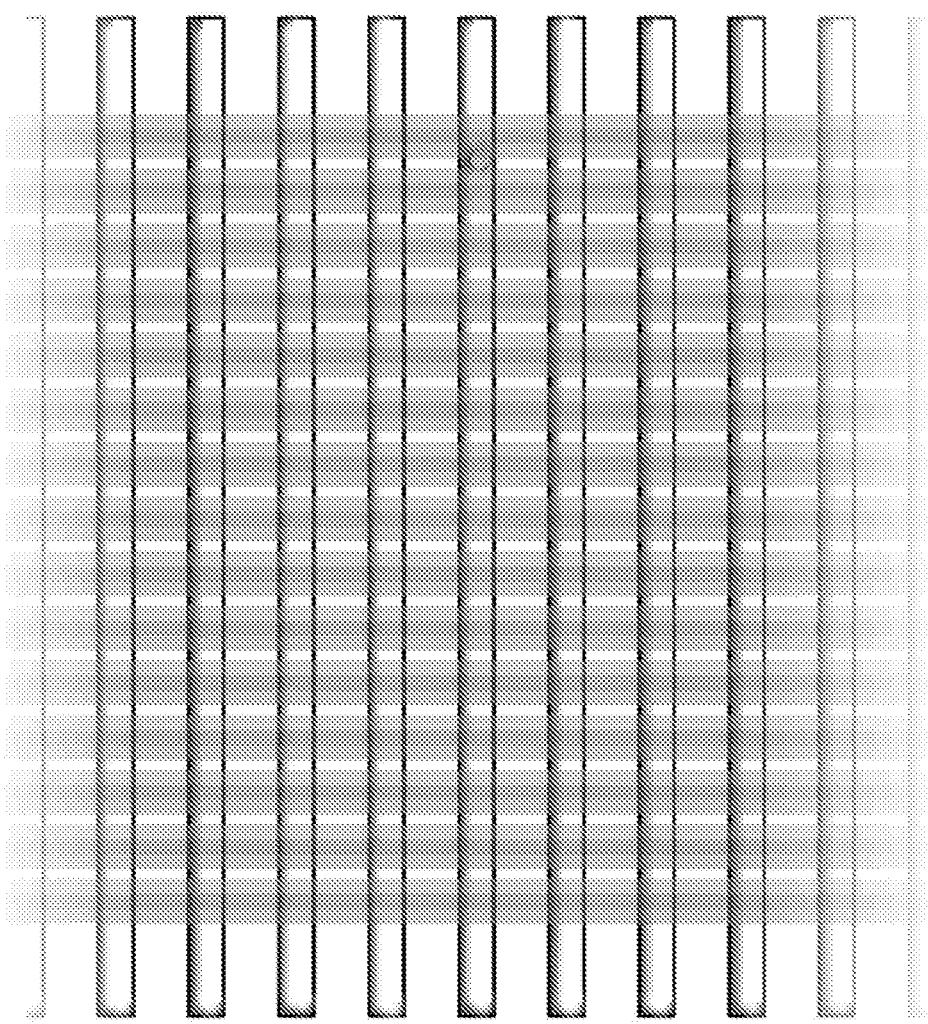
FIG. 2G is a diagram depicting an example illustration of the crossover of microchambers and antibody barcode arrays, according to some embodiments.

FIG. 2C shows a diagram illustrating an example cartridge assembly containing a plurality of microchambers molded into a silicone surface, according to some embodiments. The microchambers may be arranged in rows (a plurality of rows such as 15, for example), each row configured to contain individual cells, e.g., 280. FIGS. 2D-F show example diagrams illustrating one, two and three antibody barcode arrays printed onto a glass slide surface, respectively, according to some embodiments. In some embodiments, a plurality of antibody barcode arrays may be printed onto the glass slide surface, and the antibody bars may be printed with different fluorescing agents, allowing for spectral encoding. For example, the antibody bars may be printed with fluorescing agents of different colors (e.g., 1 color, 2 colors, 3 colors, or more), and the presence of multiple colors may facilitate spectral encoding. Further, in some embodiments, spatial encoding may be provided by the number of barcodes molded or available in the silicone surface (e.g., 1-100 bars (as a specific example, 15 bars)). In some embodiments, by combining spectral encoding and spatial encoding in each microchamber, a very high, even unprecedented, degree of multiplexing may be obtained for single-cell protein secretion assay. For example, with reference to the embodiment of FIGS. 2D-F, 3 different color fluorescing agents (e.g., green, red, blue) and 15 antibody barcodes may facilitate the detection of 45 proteins, with a total of 45 antibodies printed (e.g., 45-plex including 42 proteins and 3 positive controls). FIG. 2G shows an illustrative diagram of the crossover of microchambers and antibody barcode arrays, in some embodiments.

FIGS. 3A-F illustrate the workflow of an assay according to some embodiments using such a chip. For example, the assay can be fully validated in terms of analytic metrics and robustness via several comparative studies and control experiments including (1) examining batch-to-batch consistency (e.g., correlation R of about 0.89), (2) validation with population multiplexed secretion measurement (e.g., a correlation R of about 0.58 (e.g., because the population measurement is more substantially affected by paracrine signaling)), (3) validation using the flow cytometric intracellular cytokine staining assay (a correlation of about 0.87), and (4) several control experiments performed to verify the workflow (e.g., aforementioned workflow) does not perturb cells to introduce variation or artifacts (for example, tests performed on substrates, silicone vs conventional petri dish, with different rigidity effects showed a high Pearson correlation R about 0.99). Cell viability can be greater than 95.5% after incubating immune cells in the microdevice for 20 hrs and a hypoxia test confirmed greater than 99.9% of cells incubated in the microchambers remains normoxia after 24-h culture.

Antibody/Capture Substrate. Spatially located thin-line capture agent array deposition techniques may greatly increase throughput capabilities versus conventional methods. The present disclosure describes various methods for high throughput manufacturing and quality control of spatially differentiable and high resolution microscale capture agents for use in single-cell functional and poly-functional profiling. One exemplary method comprises a high throughput vacuum patterning (HTVP) technique capable of increasing the quality and consistency of the antibody deposition for substrates including thin-line capture agent arrays.

The methods and apparatus disclosed herein provide high throughput sample deposition techniques with superior resolution, consistency, and throughput. Further, these methods are particularly suitable for parallel sample processing and scale well for manufacturing. The methods have the added benefits of significant reductions in hands-on preparation time, reduced material costs, and overall reduction in processing time. Disclosed herein are devices and instruments that simplify the user's tasks and automate the entire workflow.

Figure 3A:
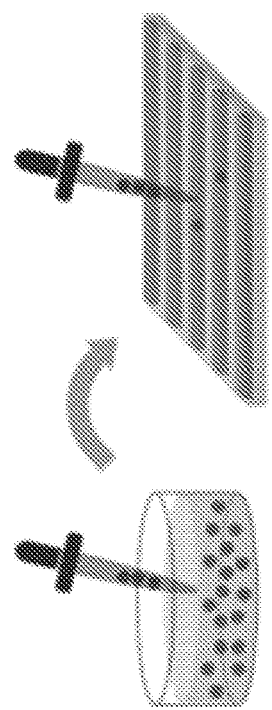
FIGS. 3A-F are diagrams illustrating an example workflow of an assay, according to some embodiments.
Figure 3B:
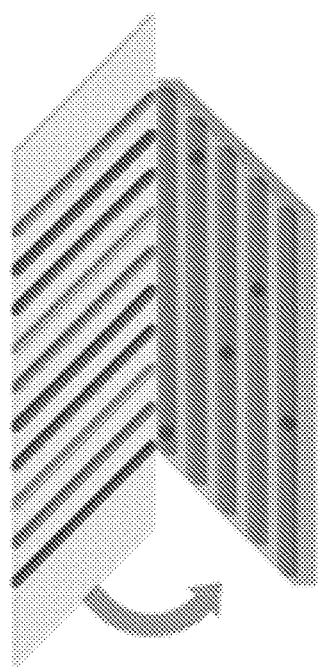
Figure 3C:
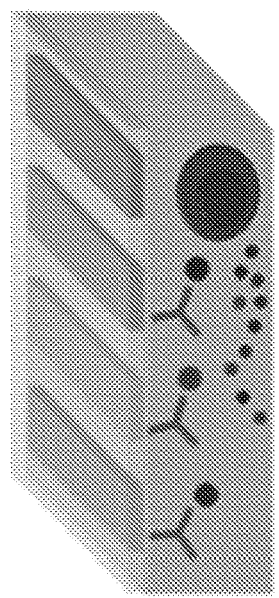
Figure 3D:
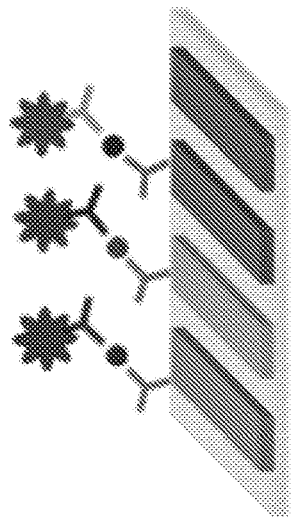
Figures 3E, 3F:
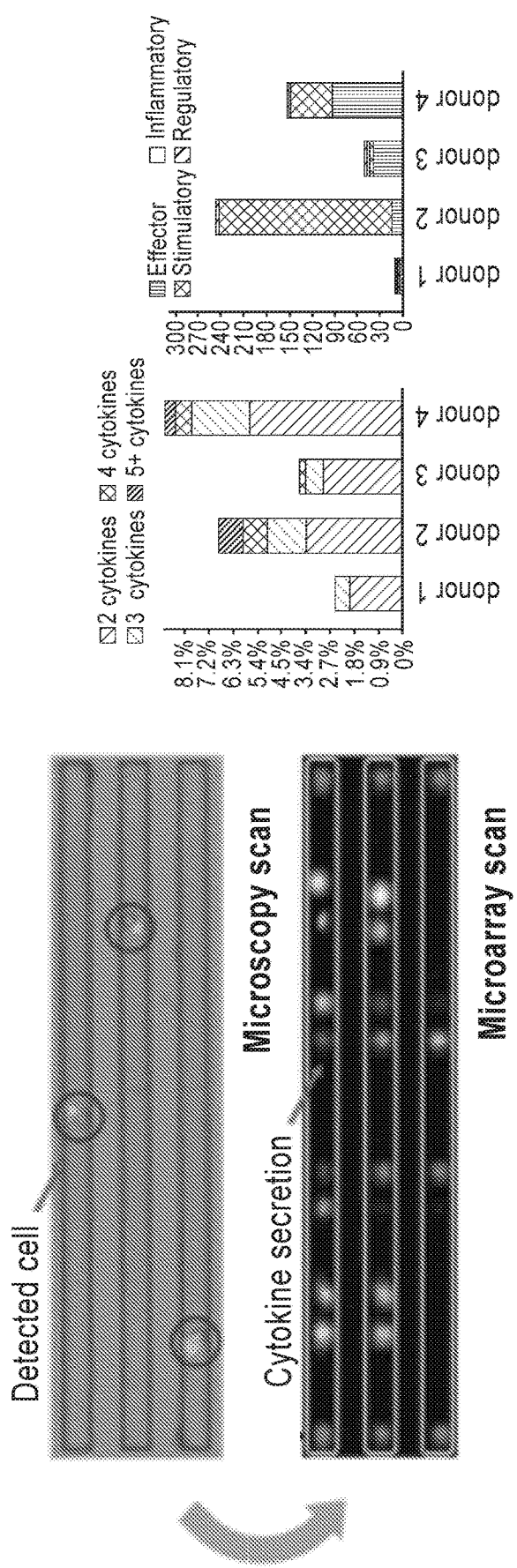

An example embodiment of the workflow of an assay as disclosed herein may comprise the following steps. FIG. 3A shows an example embodiment of suspended cells being petted onto microchamber array for single-cell capture. In some embodiments, the antibody barcode array slide is placed over the microchamber array and imaged with a microscope, e.g., FIG. 3B. In some embodiments, with reference to FIG. 3C, the cells incubated for some duration (e.g., 12-16 hrs) secrete cytokines that are then captured by the antibody barcode. The slide may then be removed and the completed sandwich assay may be imaged with microarray scanner, e.g., FIG. 3D. In some embodiments, with reference to FIG. 3E, a software (e.g., CytoSpeak) may be utilized to extract data by overlaying detected cells with quantified cytokine secretions, which allows for the presentation of single-cell polyfunctionality data as shown in FIG. 3F. FIGS. 4A-H provide example embodiments of the workflow of single cell detection.

Figure 4A:
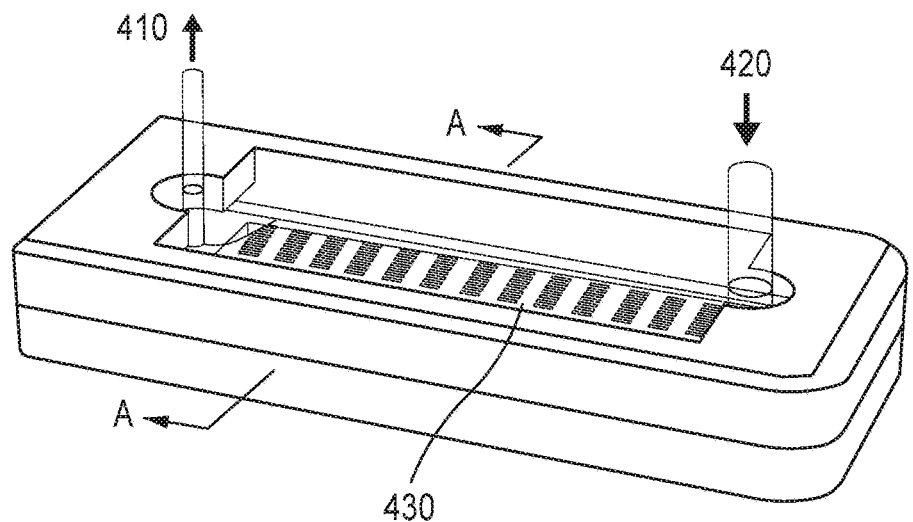
FIGS. 4A-H are example diagrams illustrating the workflow of single cell detection using the cartridge assembly, according to some embodiments.
Figure 4B:
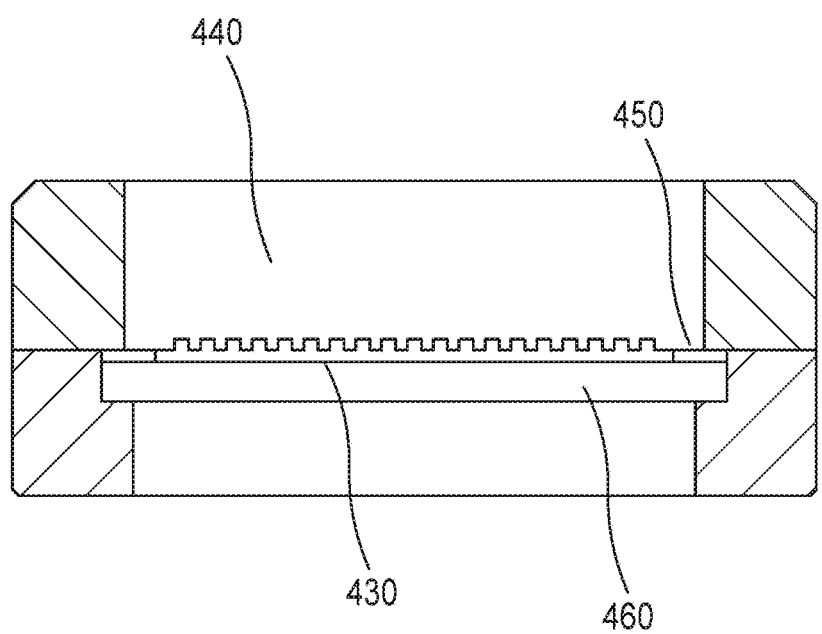

FIGS. 4A-H are example diagrams illustrating the workflow of single cell detection using the cartridge assembly, according to some embodiments. FIGS. 4A-B are example diagrams illustrating the flow of single cell suspension through the cartridge assembly, according to some embodiments. In some embodiments, the diameters of the inlet orifice 420 and outlet orifice 410 may be different. For example, the former may be larger than the latter. In some embodiments, the flow chip may comprise inlets 420, outlets 410, and flow channels 430 which seal against a glass substrate for making a capture substrate. A gasket 450 may also be used to facilitate in creating the flow path 430. The device may be fabricated at least partially from silicone and may be modified to accommodate the methods discussed below. Flow chip inlet and outlet diameters cut with, for example, a 0.028" (0.71 mm) punch allow for sealing against 23 gauge stainless steel needles due in part to the elastomeric properties of the silicone. In some embodiments (e.g., FIG. 5), enlarging the inlet and outlet diameters to approximately 1.5-2 mm permits sample volumes of approximately 1 µL-4 µL to be deposited using, for example, a 10 µl pipette tip into the microliter sized reservoirs formed by the larger inlet cutouts. This process can also be suitable for adaptation to a robotic platform for depositing antibodies into the inlets. A flow chip modified to include enlarged inlets and outlets can be used for vacuum pattering antibodies onto an antibody-encoded slide.

In some embodiments, sample or liquid flow through channels 430 may be effected via motorized and/or manual pipetting, pumping and positive/negative pressure differentials. For example, sample flow through channels 430 may be achieved by applying pressure individually with tubing per inlet using for example compressed nitrogen. Such techniques may be extended using a device and method designed to substantially uniformly apply pressure across multiple or substantially all sample inlets. In various embodiments, a sample can be pipetted into the inlet side of the Flow Chip. A pressure chamber, which can surround the pattern or outline of the inlets, can be placed on the inlet side of the Flow Chip attached for example by a single line of tubing.

Figure 6:
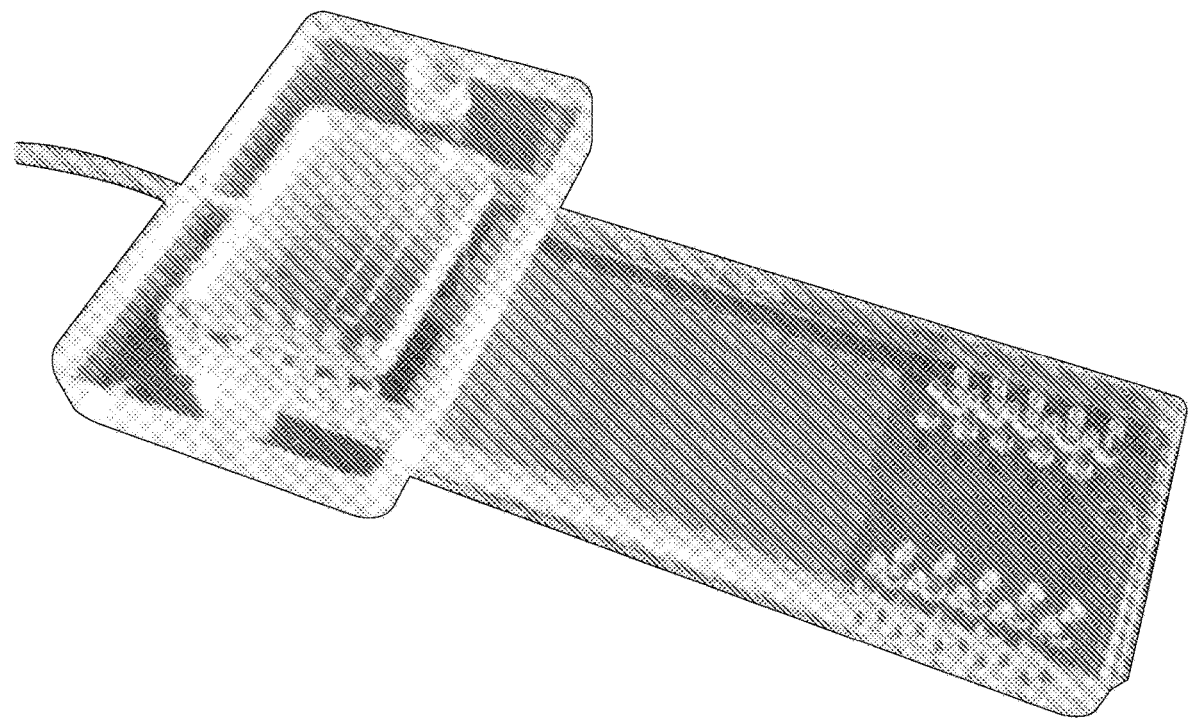
FIG. 6 is a diagram illustrating setting up a pressure chamber and a single vacuum line, according to some embodiments.

Additionally, vacuum or negative pressure may be applied to a single tubing line attached to a pressure chamber on the outlets to pull, draw, or distribute a sample through the channels. In various embodiments, the negative pressure aids in securing or sealing the pressure chamber to the Flow Chip due in part to the elastomeric sealing properties of the silicone. Vacuum may be applied to the flow chip for several hours (e.g., 3 or more hours) and then further processed. Once the capture agents (antibodies or nucleic acids) are patterned on the glass substrate, the patterned glasses slide is referred to as the antibody-encoded slide (e.g., as shown in FIG. 6). FIG. 6 shows a pressure chamber with a single vacuum line that enables high throughput pulling of antibodies through long microchannels. This method enables all channels to be pulled in parallel, at speeds ten times that of previous methods. These two parts can be discarded after manufacturing, leaving the antibody-encoded slide.

Figure 4C:
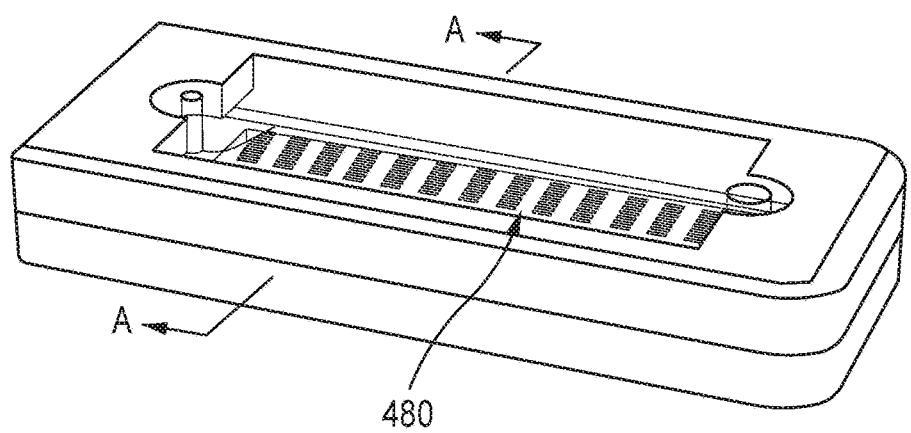
Figure 4D:
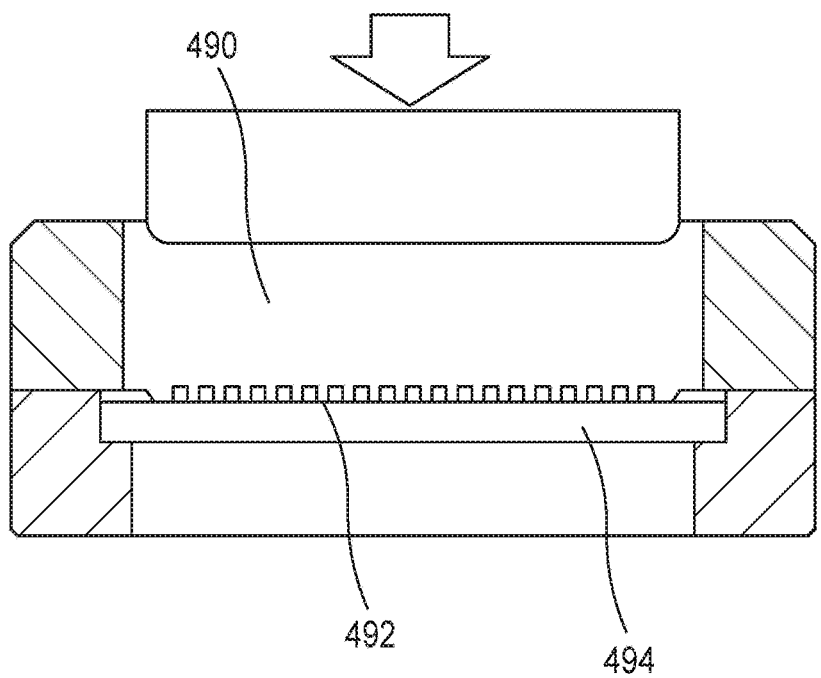
Figure 5:
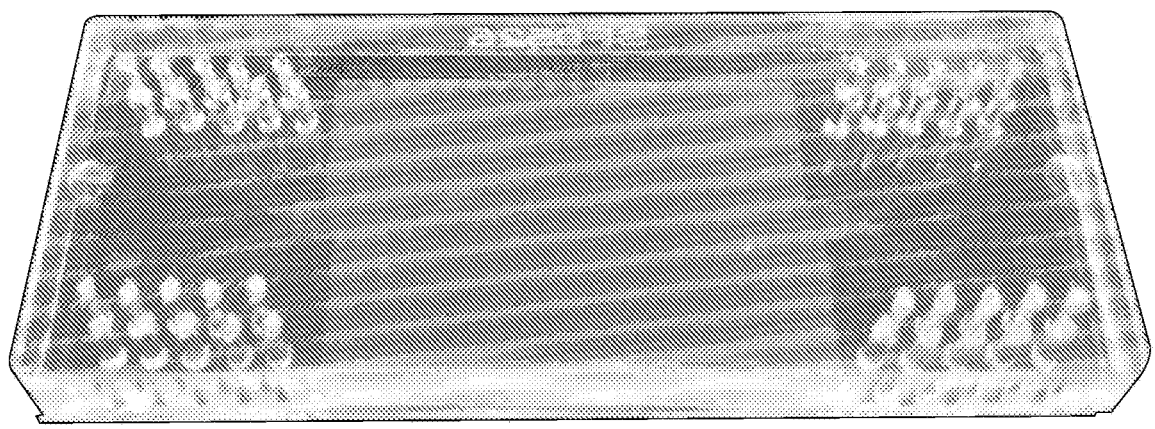
FIG. 5 is a diagram illustrating an example modified Flow Chip with enlarged inlets and outlets, according to some embodiments.

FIGS. 4C-D are example diagrams illustrating the compression of silicone to isolate single cell suspension within the microchambers, according to some embodiments. For example, the compression of the silicone 490 closes the flow path 492 adjacent to the glass side 494 of the flow chip, resulting in the isolated micro-chambers 480.

Figure 4F:
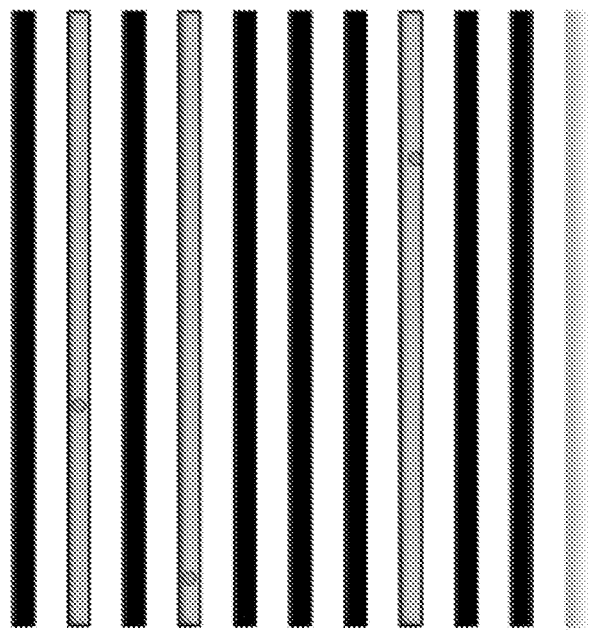
Figure 4E:
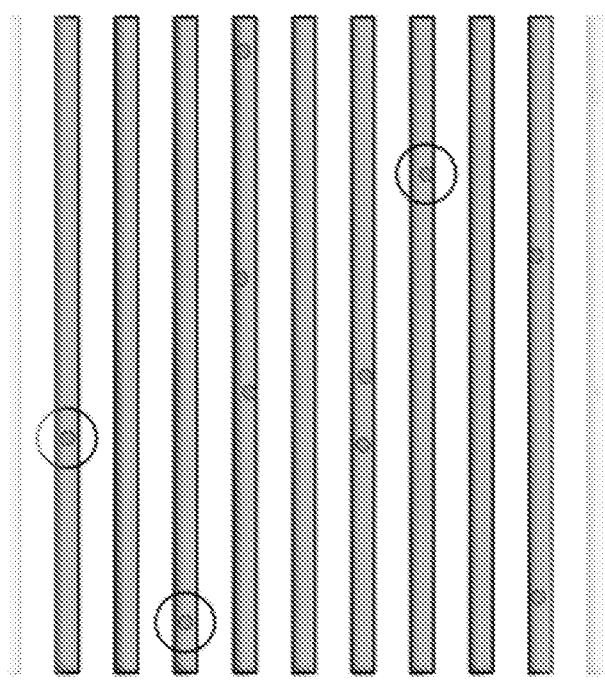
Figure 4G:
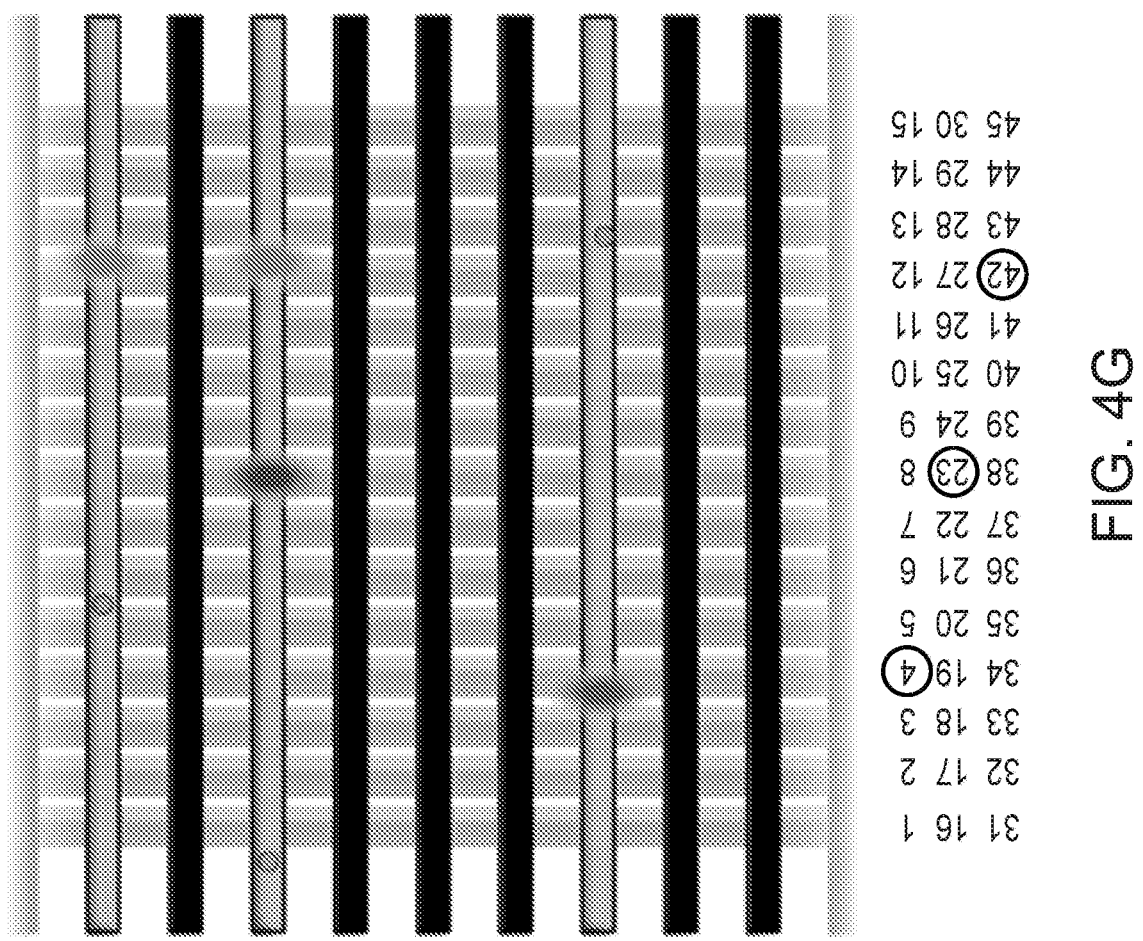
Figure 4H:
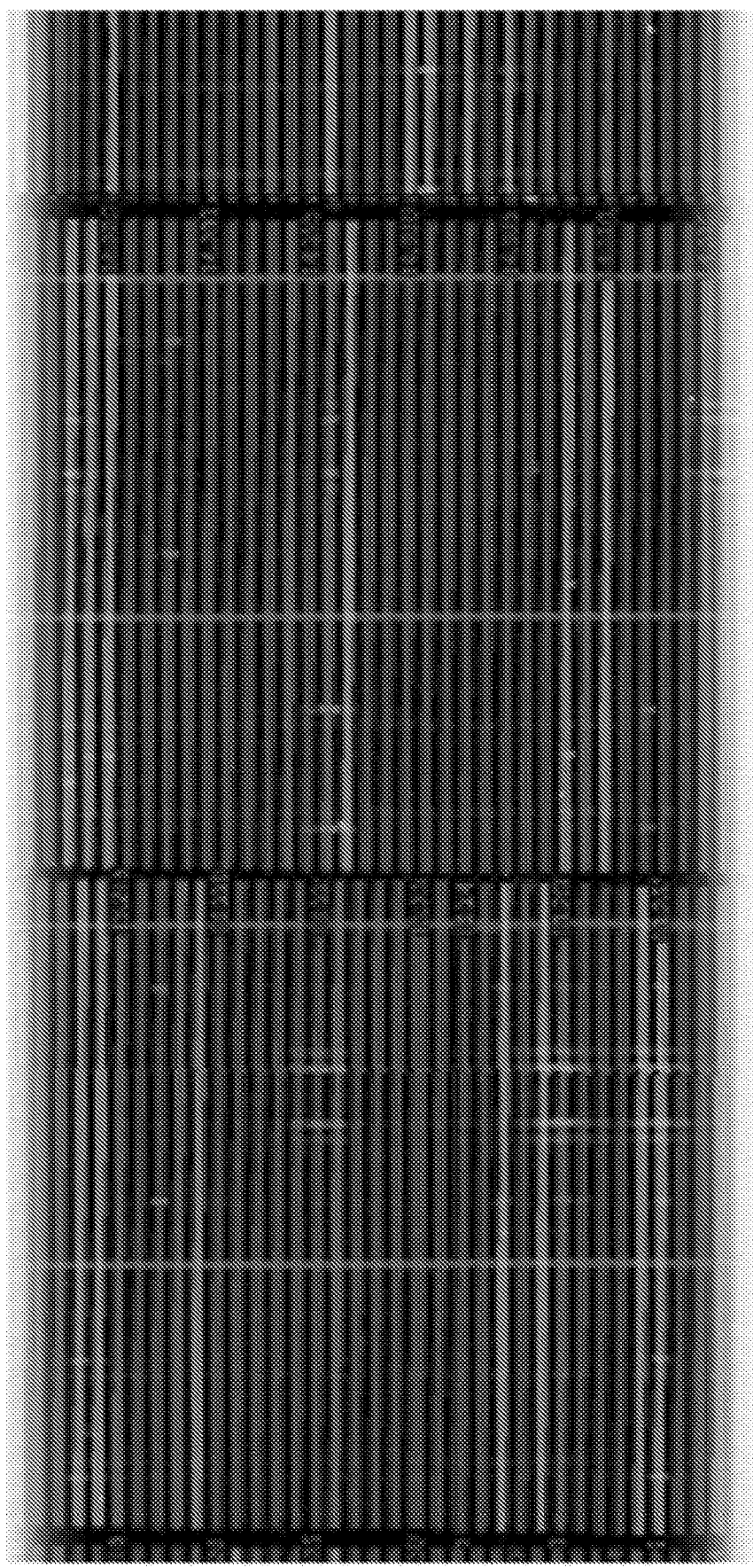

FIG. 4E is an example embodiment illustrating the scanning of the microchambers to identify microchambers containing only one cell. Some microchambers may have a plurality of cells (two or more) and others may have none. The microchambers with only a single cell are indicated with circles identifying the single cells in the respective microchamber in FIG. 4E. FIG. 4F provides another illustration of microchambers containing only single cells (microchambers containing no cells or at least two cells are disregarded (shown as black stripes)). As discussed above with reference to some embodiments, incubated cells secrete proteins which bond to antibody barcode arrays for identification, e.g., FIG. 4G. FIG. 4H provides an example image of the cartridge assembly with fluorescent proteins, according to some embodiments.

Figure 7:
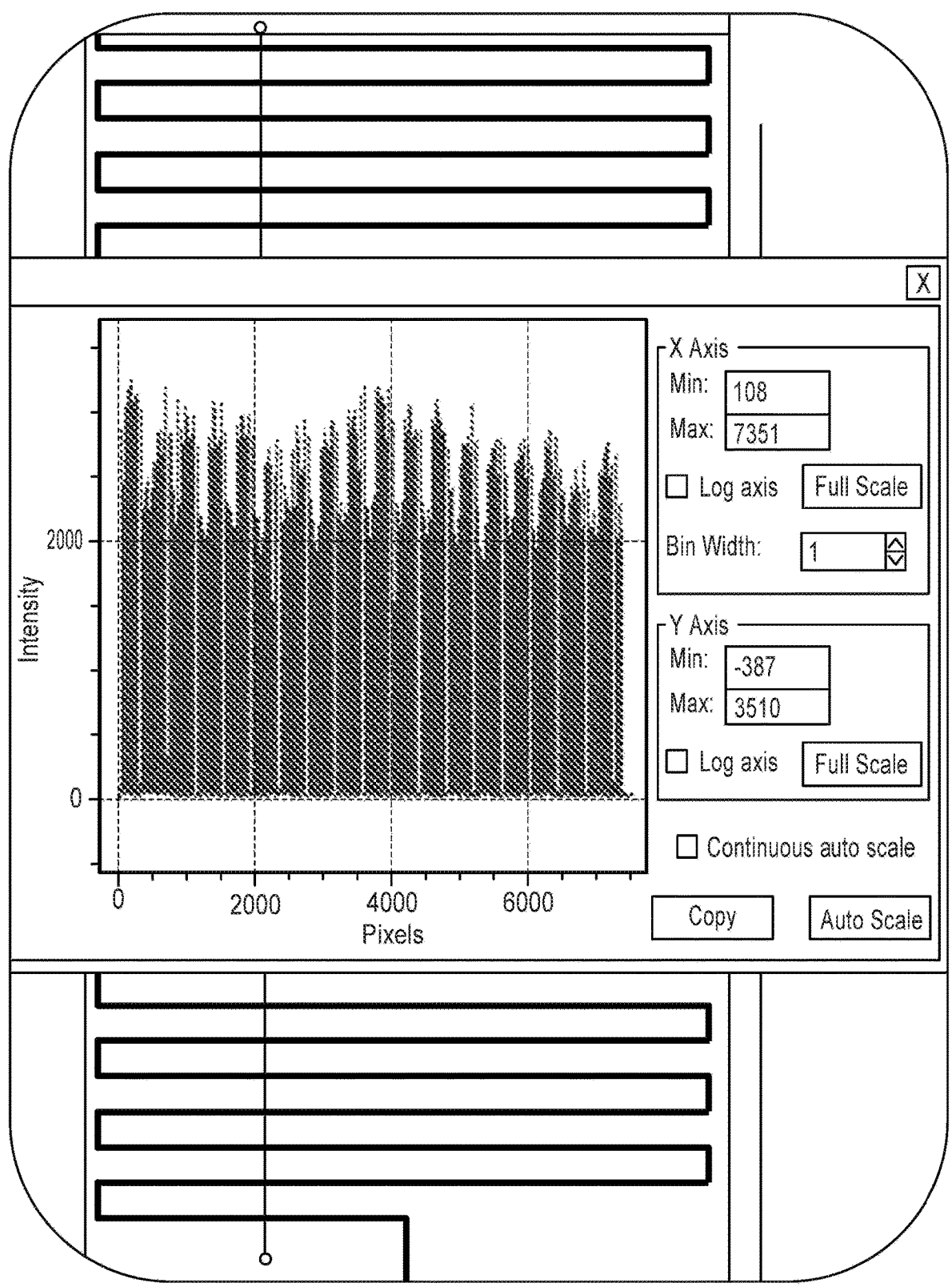
FIG. 7 is a diagram illustrating example antibody IGG fluorescence uniformity across the entire slide, according to some embodiments.

FIG. 7 is a diagram illustrating example antibody IGG fluorescence uniformity across the entire microscope slide. For example, in some embodiments, vacuum or negative pressure may be applied to the single tubing line attached to the pressure chamber on the outlets to pull, draw, or distribute sample through the channels. In various embodiments, the negative pressure aids in securing or sealing the pressure chamber to the Flow Chip due in part to the elastomeric sealing properties of the silicone. Vacuum may be applied to the flow chip for 3+ hours and then further processed. Once the capture agents are patterned on the glass substrate, the patterned glasses slide can be referred to as the capture agent substrate.

Figure 9:
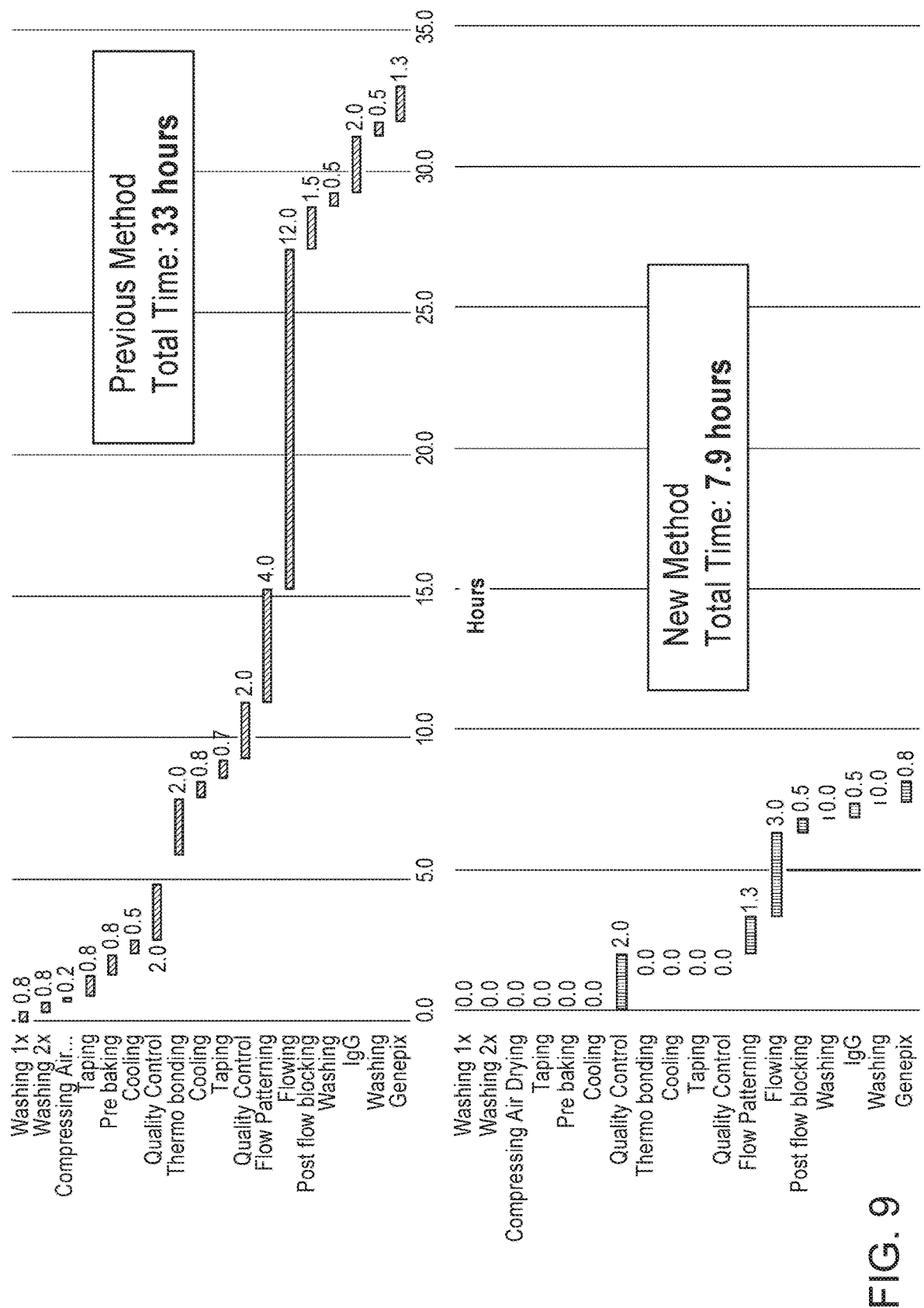
FIG. 9 is a diagram illustrating example Gantt charts demonstrating the manufacturing time of the Vacuum Patterning method, according to some embodiments.

The disclosed methods provide advantageous methods for vacuum-based flow chip filling that can achieve bonding of silicone to the glass substrate without thermal mechanisms. These vacuum-based techniques address disadvantages of positive pressure sources which, for example, can delaminate silicone from the substrate. The disclosed methods may further save substantial processing time avoiding delays due to bonding and cooling times (e.g., such as that illustrated in FIG. 9, which demonstrates a five-fold reduction in bonding and cooling times). In various embodiments, the disclosed methods reduce or eliminate sources of contamination as compared to other processes which, for example, may result in heated silicone leaching onto the substrate. According to the present methods, the silicone does not require heating and thus reduces or eliminates a significant source of surface contamination. Additionally, the silicone does not require pre-washing prior to being used in the process.

Figure 8:
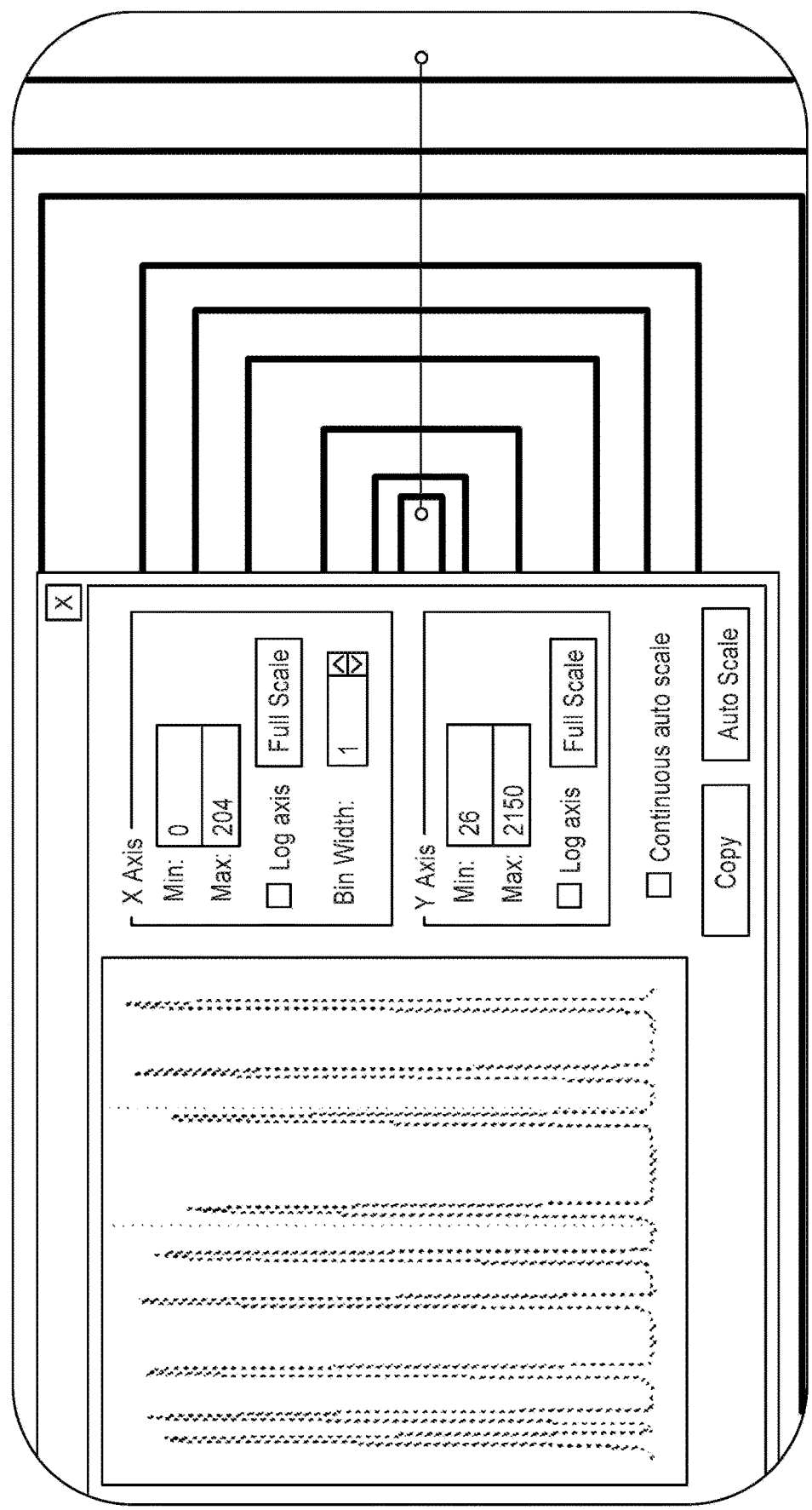
FIG. 8 is a diagram illustrating example antibody IGG fluorescence uniformity across all channels, according to some embodiments.

FIG. 8 is a diagram illustrating example antibody IGG fluorescence uniformity across all channels. For example, in some embodiments, the vacuum-based methods for sample deposition remove or reduce a primary failure mode as compared to methods which apply pressure to the channels to push or distribute sample through the channels. When applying pressure, blockages and pressure build ups can result in delamination of the flow chip from the substrate. Such conditions may render the product inoperative wasting time and materials. Applying vacuum-based methods for sample deposition, failures from pressure build up can be eliminated as no positive pressure is applied. The negative pressure of vacuum draws the sample through the channels and the flow chip down onto the surface which facilitates a better seal. The use of single tubing to pull vacuum through a pressure chamber reduces complexity by eliminating the need to use a single piece of tubing for each outlet. The single tube and pressure chamber arrangement also reduces assembly time over multiple tubes. The vacuum-based method provides a tenfold improvement in throughput in comparison to previous methods. In some embodiments, methods and apparatuses herein can also capture proteins and various nucleic acids.

Figure 10:
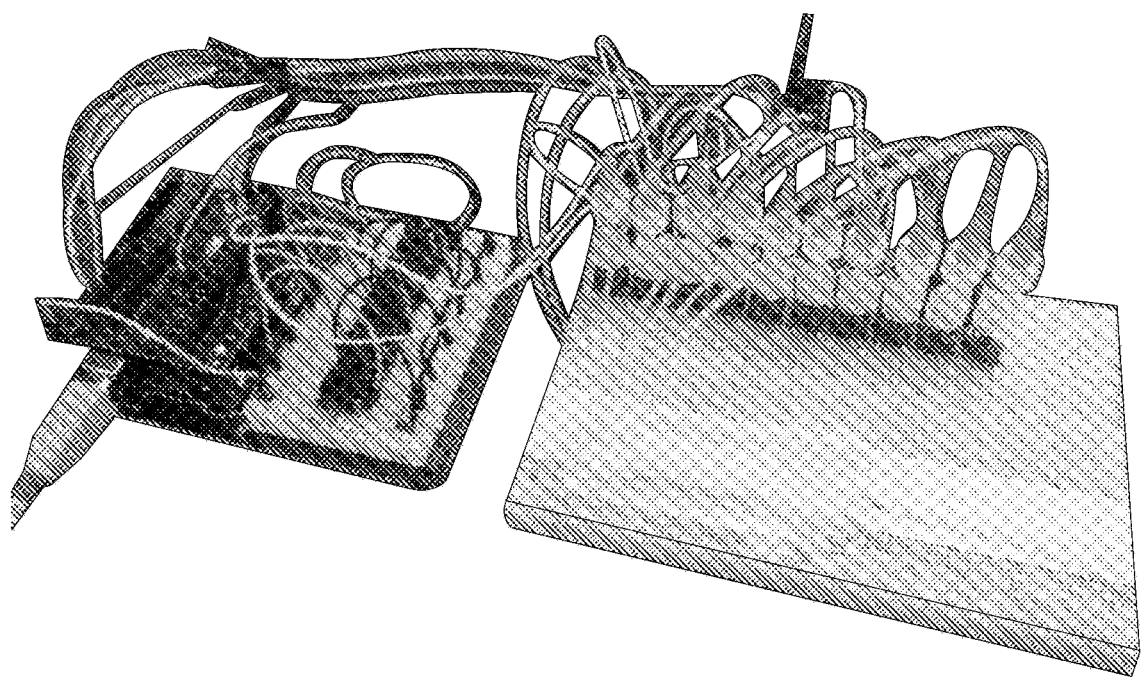
FIG. 10 is a diagram illustrating a quality control fixture for evaluating whether channels on a flow chip have blockages before the flow chip is used, according to some embodiments.
Figure 11:
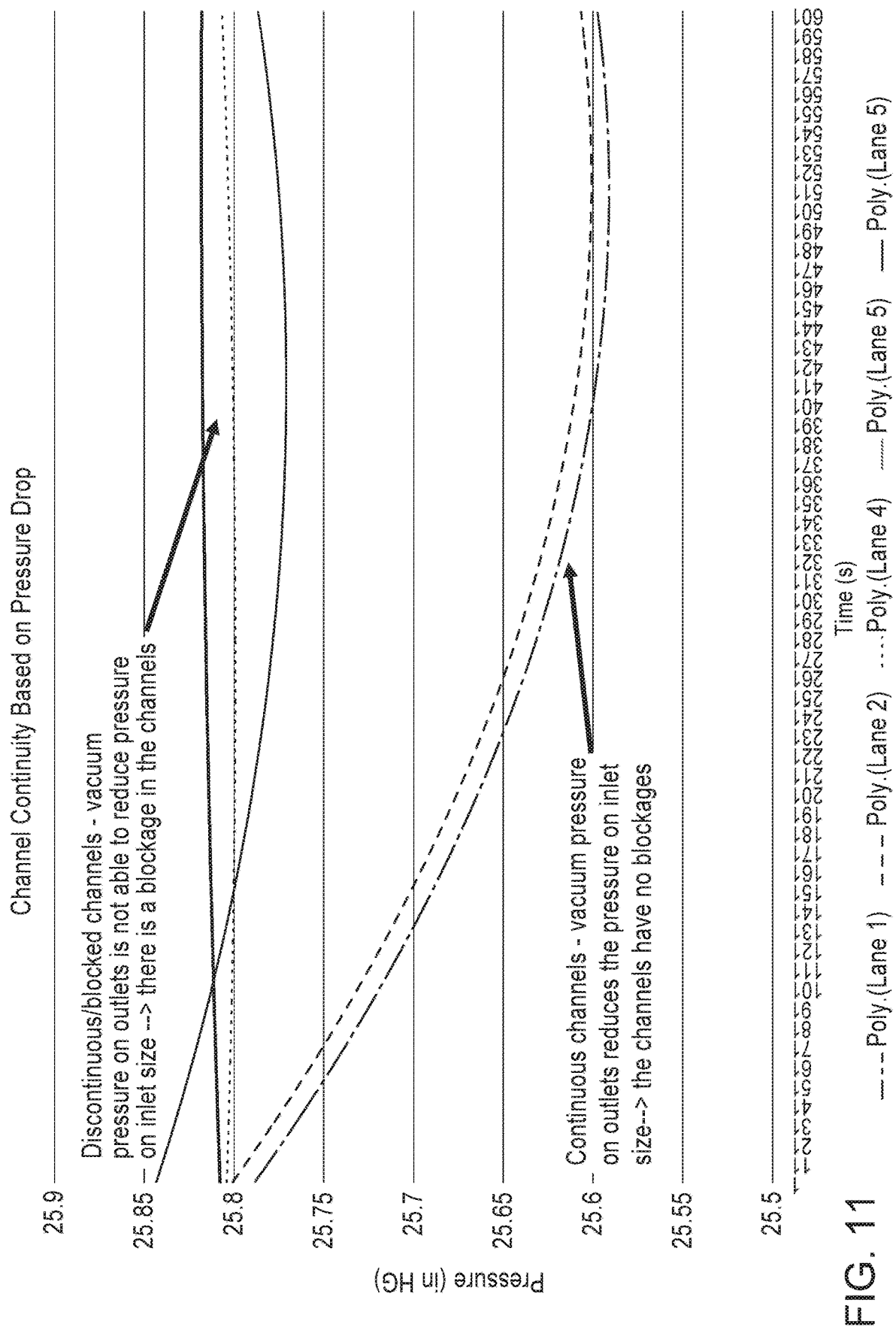
FIG. 11 is a diagram illustrating example pressure data from a quality control fixture, according to some embodiments.

In various embodiments, a quality control device and methods may be used to evaluate or identify blockages in the flow chip when assembled with the glass substrate. Pressure sensors may be adapted for use with the channels and pulling vacuum on the outlets (e.g., such as that illustrated in FIG. 10). Each channel may be configured as a closed system with a pressure sensor. In various embodiments, where the channel is continuous with no blockages, the pressure may be observed to drop on the inlet side of the chip where the pressure sensor is located. In instances where a blockage may be present in the channel, the pressure sensor may not detect a pressure drop as the air flow is discontinuous due to the blockage (e.g., such as that illustrated in FIG. 11).

Figure 12:
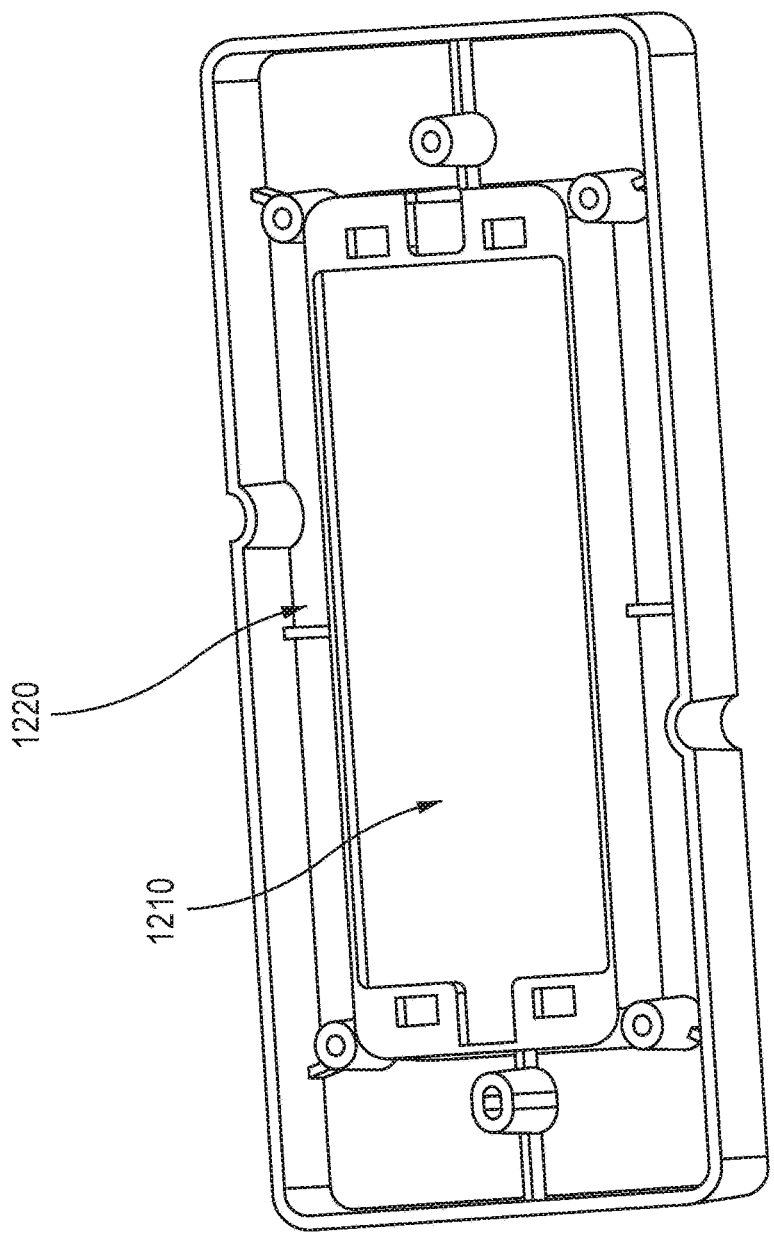
FIG. 12 is a diagram illustrating an example housed microchamber substrate, according to some embodiments.

Compressible (e.g., silicone) Substrate and optional housing. FIG. 12 is a diagram illustrating an example housed microchamber substrate. For example, in some embodiments, a microchamber substrate housing 1220 allows for fast and efficient manufacturing of the microchamber substrate 1210. This microchamber substrate housing 1220 can be used within the consumable and the automated instrument, each of which is disclosed herein. The housing 1220 can be placed against a mold, and an elastomer (silicone) can be poured into the mold. Once cured, support features within the holder allow for efficient demolding by retaining the silicone. The mold geometry can produce a chamber substrate 1210 that extends beyond the bottom surface of the holder. This allows for a seal to be created between the chamber substrate and the capture agent substrate. The mold geometry can also feature a recessed area that can serve as a cavity through which reagents can be flowed. The height of the cavity can be in the range of about 20-200 μm. Two openings on each side of the microchamber substrate can serve as an inlet and outlet for reagents. A taller cavity may be less likely to collapse, and may receive less pressure to push liquids through. A shorter cavity may collapse, therefore impeding the flow of reagents; a shorter cavity height can also be beneficial, however, because it can reduce reagent waste. A collapsed microchamber substrate is defined as an unwanted liquid flow obstruction caused by the microchamber substrate fixing to the antibody-encoded substrate. Thus, the microchambers can allow for the capture of individual cells for multiplexed analysis of analytes from single-cells.

Figure 13:
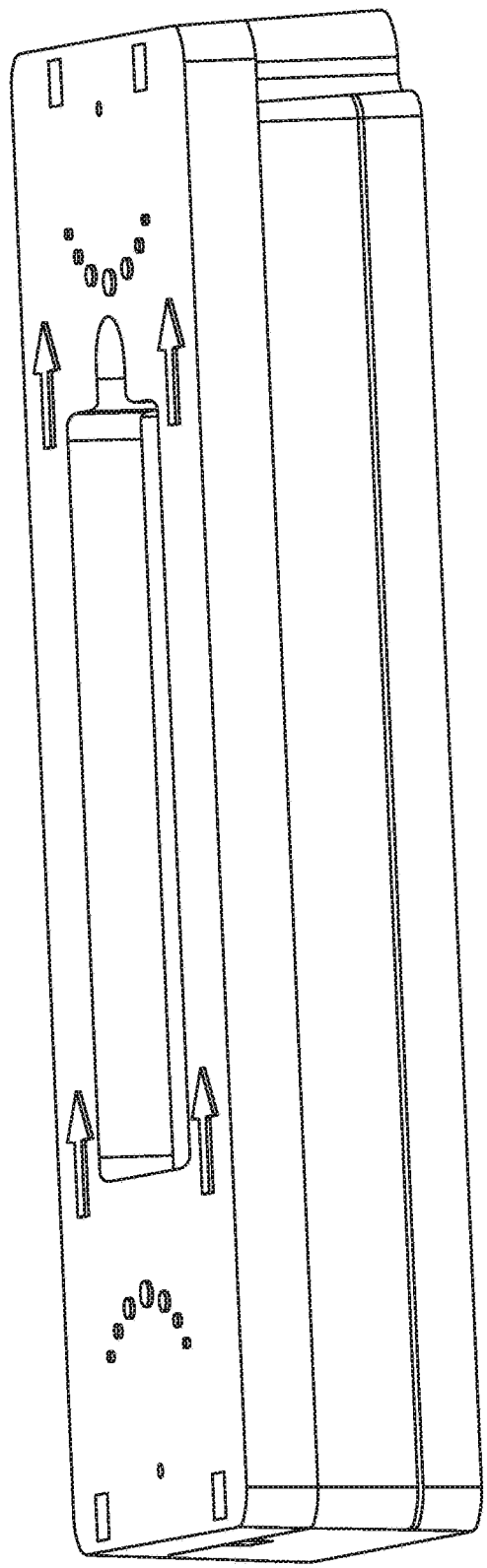
FIG. 13 is a diagram illustrating an example consumable, according to some embodiments.
Figure 14:
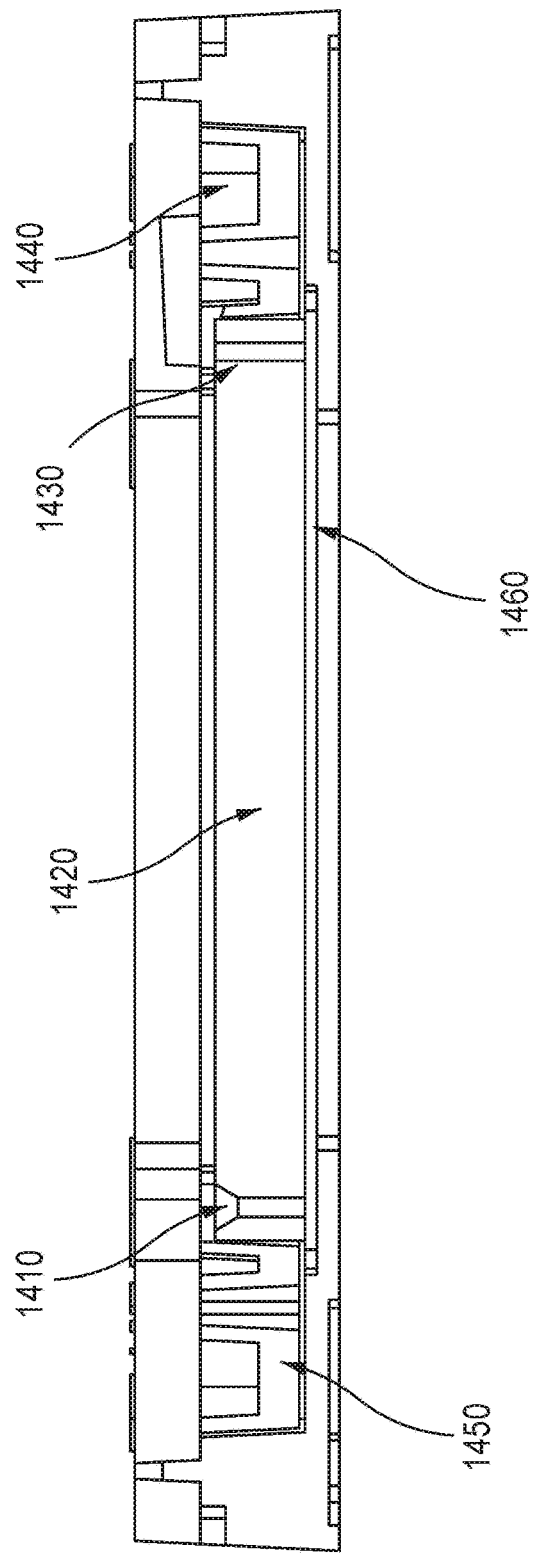
FIG. 14 is a diagram illustrating an example cross-section of a consumable, according to some embodiments.

Consumable (example). FIG. 13 is a diagram illustrating an example consumable. For example, in some embodiments, an injection molded consumable is composed of the housed microchamber substrate, the capture agent substrate (e.g., the antibody-encoded slide), and the two-part consumable structure. The two-part consumable structure retains the housed microchamber substrate and securely seals it against the capture agent substrate. The seal that is created allows for liquid to flow through the inlet of the housed microchamber substrate to its outlet. The integrity of the seal is important, as a poor seal may retain reagents, which can contaminate subsequent reagents flowed through the cavity. This consumable is easy to handle and is easily placed into the automated instrument (e.g., as shown in FIG. 14) by the user. The consumable has features that retain used reagents that come out of the outlet. This allows the user to dispose of the entire consumable at the end of the assay without the need to clean any components.

FIG. 14 illustrates a cross-section of an example consumable. The consumable can include components such as (1) the silicone or other material microchamber substrate 1420, (2) the antibody encoded slide (i.e. antibodies) $1460_{[41]}$, (3) the housing, which retains the chamber substrate, (4) the used reagent reservoir 1440, which is a feature of the housing that retains allow liquids that are passed through the cavity, (5) an inlet 1410 for all reagents to enter the cavity created between the antibody encoded slide and microchamber substrate, and (6) and an outlet 1430, which provides a path for used liquids to exit the cavity and enter the used reagent reservoir 1440.

Figure 15A:
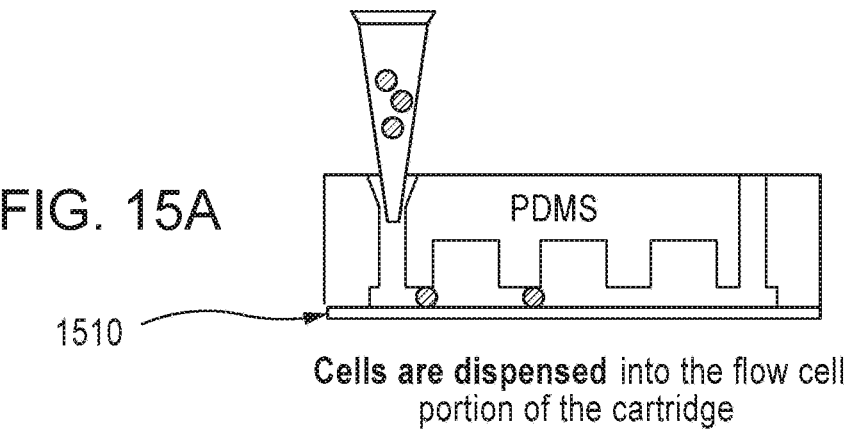
FIGS. 15A-C are diagrams illustrating capturing of cells within an example consumable and staining capture agent substrate for secretion detection, according to some embodiments.
Figure 15B:
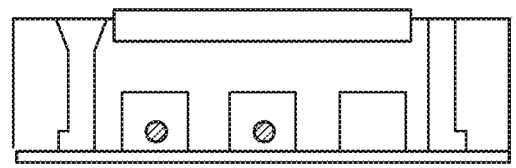
Figure 15C:
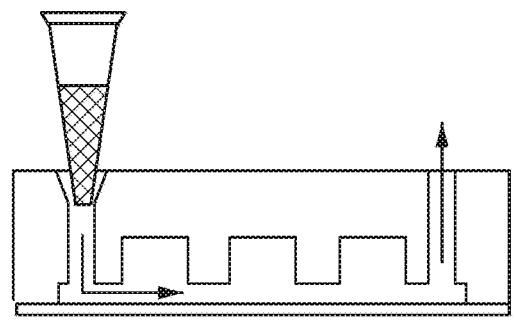

FIG. 15 is a diagram illustrating capturing of cells within an example consumable and staining a capture agent substrate 1510 for secretion detection. For example, in some embodiments, cells are dispensed into the cavity and then trapped in the microchambers through compression of the microchamber substrate against the capture agent substrate. The cells can then be imaged using fluorescent and bright field microscopy to locate the cells. Through an incubation period, cells can be exposed to capture agents (e.g., such as antibodies or nucleic acids) on the capture agent substrate (e.g., on an antibody encoded slide). An incubation period can be about 5-50 hours, e.g., 6-48 hours, 6-30 hours, 12-48 hours, or 12-24 hours. Compression is then relieved and reagents are dispensed through the cavity for cleaning and fluorescent tagging of proteins. The surface of the capture agent slide can then be imaged to detect secretion signal.

Said another way, cell capture can be performed based on the following example process: (1) cells are dispensed into the flow cavity, which is created within the consumable device, and (2) cells are captured within the microchambers by compression of the chamber substrate. Secreted proteins and nucleic acids (from lysed cells) are captured by the encoded antibodies and nucleic acids (3) compression force is removed to again reveal the flow cavity so that antibodies and secondary antibodies can be labeled (or in the case of nucleic acids, different washing steps are included to remove the nucleic acids from the flow cell to enable next generation sequencing downstream) by the dispensing of reagents, (4) labeled antibodies or secondary antibodies are imaged using fluorescent microscopy.

In some embodiments, the mechanism behind protein detection described herein can be similar to that of a sandwich enzyme-linked immunosorbent assay (ELISA). Specifically, the secreted protein is captured by the capture antibody on the antibody barcode array. Then a second antibody is added, and binds to the secreted protein (hence the 'sandwich': the secreted protein is stuck between two antibodies). Enzyme-linked secondary antibodies are then applied as detection antibodies that also bind specifically to the second antibody. A chemical is added to be converted by the enzyme into a color or fluorescent or electrochemical signal.

In some embodiments, the capture antibodies bind to cytokines. In some embodiments, the second antibodies bind to cytokines. Examples of suitable anti-cytokine antibodies include, but are not limited to, anti-human G-CSF, anti-human IL-10, anti-human GM-CSF, anti-human IL-13, anti-human GROα anti-human IL-15, anti-human IFN-γ, anti-human MCP-1 anti-human IL-1α, anti-human MCP-2, anti-human IL-2, biotinylated anti-human MCP-3, anti-human IL-3, biotinylated anti-human MIG, biotinylated anti-human IL-5, biotinylated anti-human/mouse/pig TGFβ1, anti-human IL-6, polyclonal rabbit anti-human RANTES, anti-human IL-7, biotinylated anti-human TNF-α, anti-human IL-8, anti-human TNF-β, monoclonal anti-human ENA-78 antibody, monoclonal anti-human I-309 antibody, monoclonal anti-human IL-11 antibody, monoclonal anti-human IL-12 p70, antibody, monoclonal anti-human IL-15 antibody, monoclonal anti-human IL-17 antibody, monoclonal anti-human M-CSF antibody, monoclonal anti-human MDC antibody, monoclonal anti-human MIP-1α antibody, monoclonal anti-human MIP-10 antibody, monoclonal anti-human MIP-1δ/Leukotactin antibody, monoclonal anti-human SCF antibody, monoclonal anti-human/mouse SDF-1 antibody, monoclonal anti-human Tarc antibody and monoclonal anti-human IL-4 antibody.

In some embodiments, the capture antibodies and second antibodies bind to growth factor related proteins, angiogenesis or anti-angiogenesis related proteins, particularly secreted angiogenesis factors.

In some embodiments, the capture antibodies and second antibodies are selected from species which bind to infection-associated antibodies or antigens. These antibodies or antigens may be proteins or antigens from the pathogenic species which infects the infected subject, or may be protein, antigens or antibodies elicited in response to infection of a subject.

FIGS. 16A-E illustrate the testing of a prototype consumable in cartridge form, in some embodiments. For example, in some embodiments, a flow cell can include consumable device components, including the microchamber substrate and the capture agent substrate. Cells can be manually pipetted into the cartridge and a load can be applied on the microchamber substrate to trap and isolate cells in the microchambers. Images showing isolated cells and secretion signal can be shown, along with correlation data showing agreement with workflow protocols.

Figure 16A:
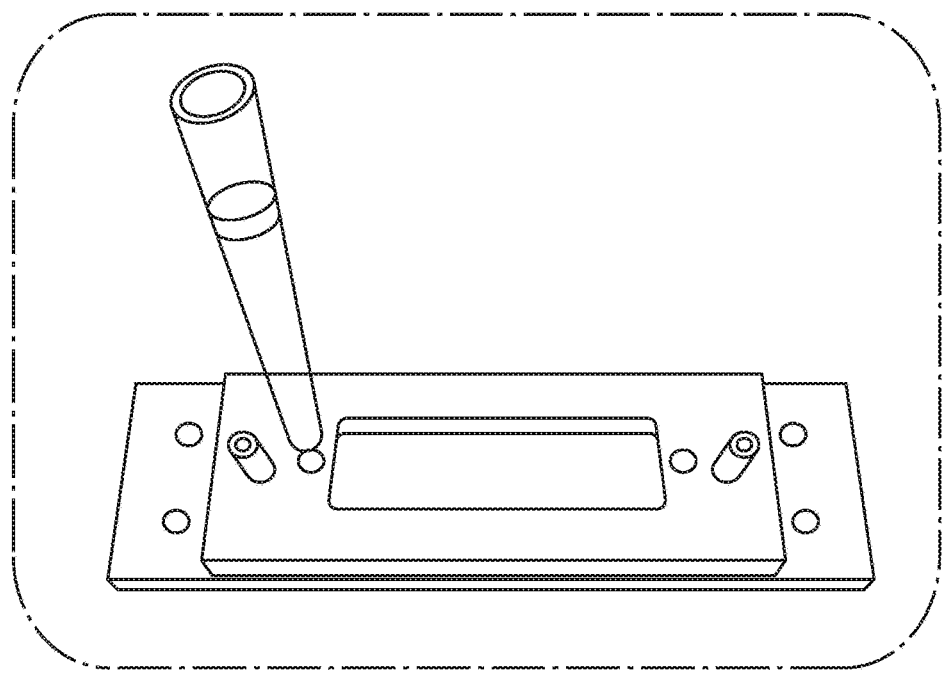
Figure 16B:
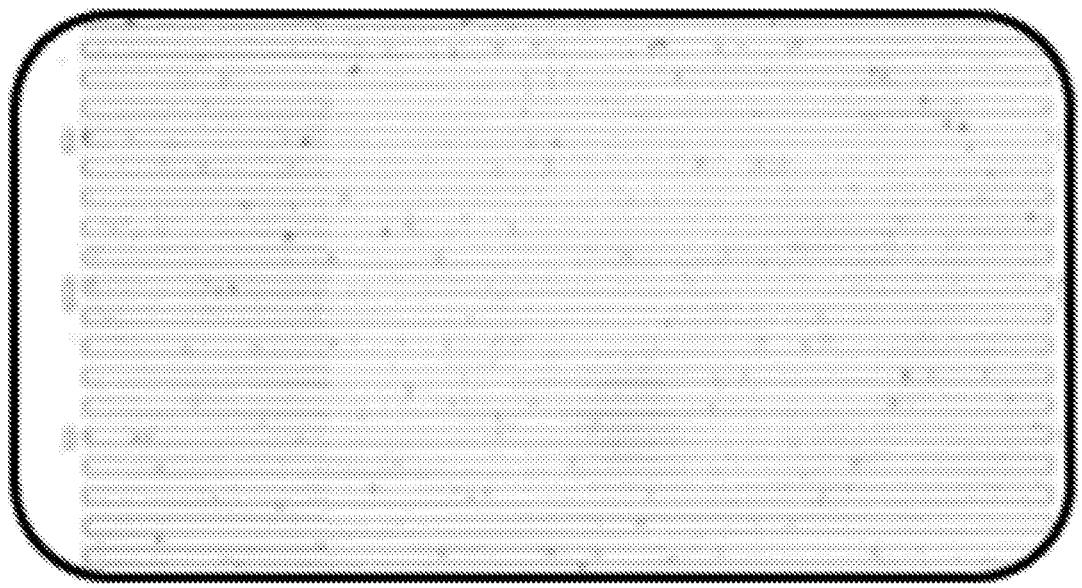

Specifically, FIG. 16 illustrates cellular imaging and proteomic capture data from the testing of a flow cell for multiplexed single-cell p silliconeroteomics, based on methods described in FIGS. 13-15. The data includes images of (1) a consumable device for single-cell multiplexed proteomic and nucleic acid capture (e.g., FIG. 16A), (2) cells imaged within microchambers as shown in FIG. 15 (e.g., FIG. 16B), (3) images of captured proteins as shown in FIG. 15 (e.g., FIG. 16C), and (4) secretion data for specific proteins showing good correlation between data obtained with the flow cell and data obtained by current IsoPlexis workflow using a manual device, disclosed herein (e.g., FIGS. 16D-E).

Figure 17:
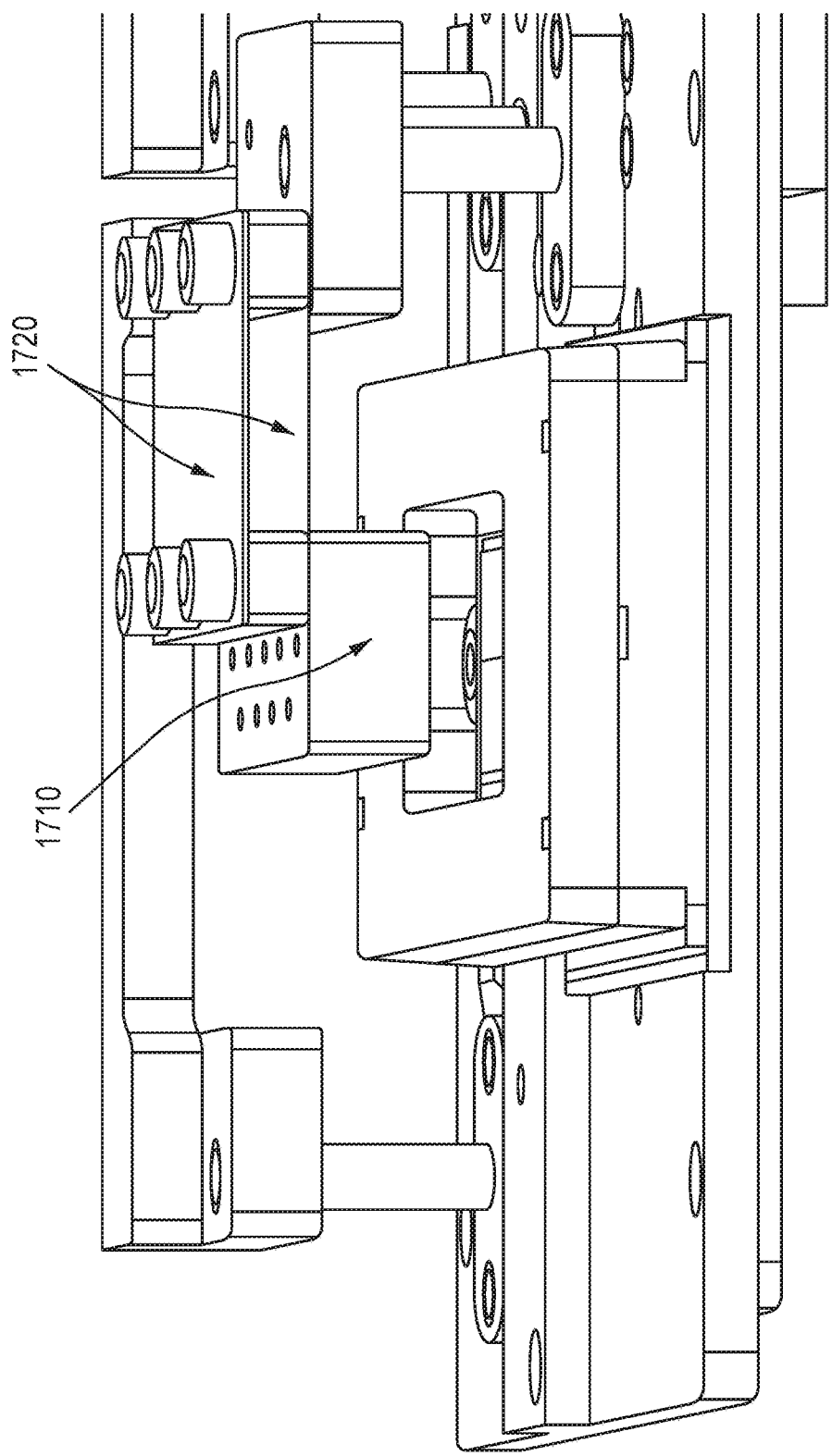
FIG. 17 is a diagram illustrating a double flexure arrangement for compressing a microchamber substrate against a capture agent substrate, according to some embodiments.

Consumable with System (e.g., automated). FIG. 17 is a diagram illustrating a double flexure arrangement for compressing a microchamber substrate against a capture agent substrate. The consumable device is designed to allow for full automation: cell loading and proteomic and nucleic acid readout. A double flexure arrangement can be used for compression of the microchamber substrate against the antibody encoded slide to facilitate the process in FIG. 15. For example, in some embodiments, a plurality of consumables can be placed into the automated instrument by the user. The consumables have a feature that only allows the user to insert them in one orientation. Immediately surrounding the consumables is a compression mechanism, which applies a load on the top of the microchamber substrate to introduce the microchamber features to the capture agent substrate. The force can be applied by guiding a rigid member 1710 to the top of the microchamber substrate by means of a double flexure (double leaf-spring) arrangement 1720. The double flexure arrangement can guide the rigid member in a linear direction to apply a uniform load against the microchamber substrate to ensure a uniform pressure between the microchamber silicone substrate and capture agent substrate. The arrangement can ensure that any cells trapped within the microchambers are sufficiently sealed. An uneven, insufficient, or excessive pressure can result in collapsed microchambers or leaking of microchamber contents.

Figure 18:
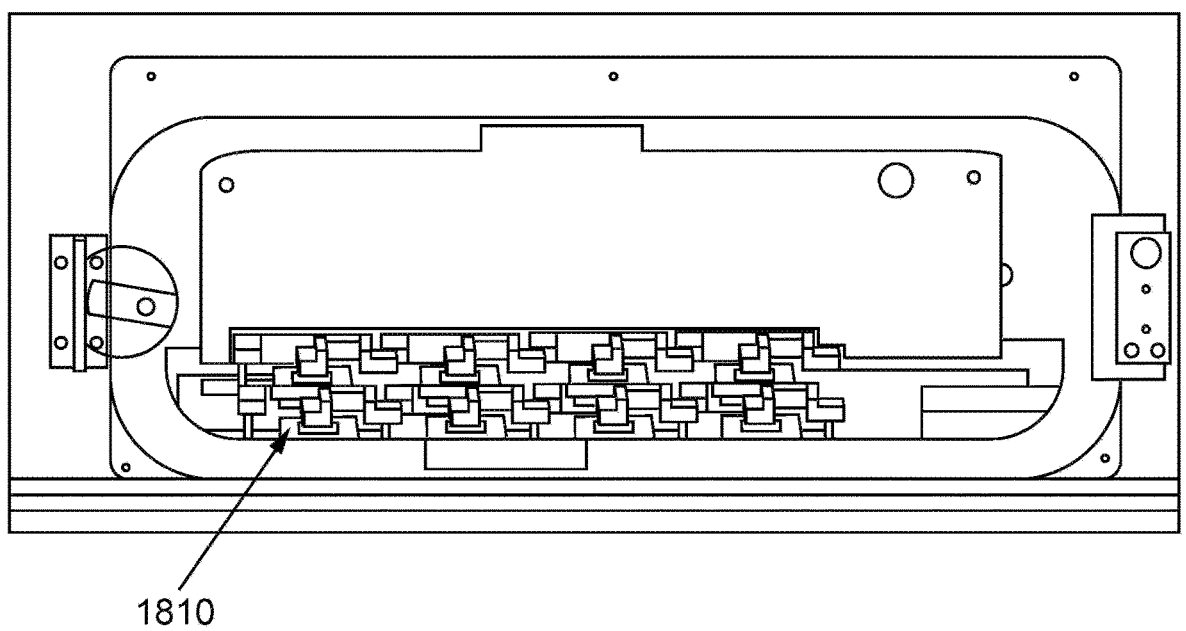
FIG. 18 is a diagram illustrating incubator module in automated instrument, according to some embodiments.

FIG. 18 is a diagram illustrating incubator module in automated instrument plurality of consumable 1810 and compression mechanism assemblies. Temperature can be controlled, while imaging both cells in their chambers and their captured analytes (protein or nucleic acids). The temperature control module in the automated instrument can accommodate a range of temperatures and CO2 settings. For example, in some embodiments, an incubator can allow for programmable temperature and CO2 injection. In this arrangement, the environment of the cells can be controlled by the user for a desired period. The incubator can be a module within the automated instrument. The incubator features an automated hinged door mechanism at the top to allow an automated reagent dispensing device to enter and interface with the inlet of the microchamber substrates.

Figure 19:
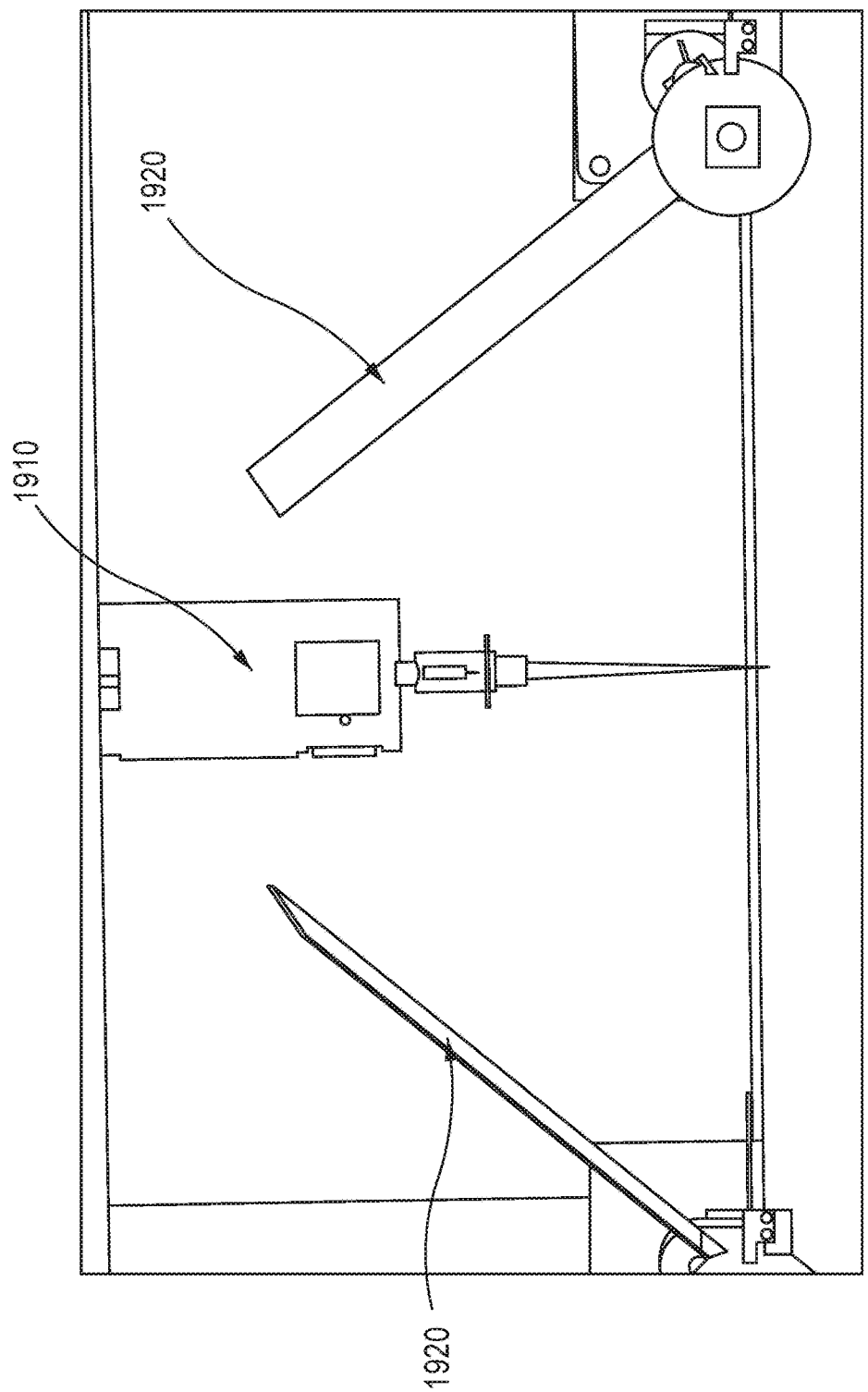
FIG. 19 is a diagram illustrating automated hinged doors on incubator that allow a dispensing head to interface with consumables, according to some embodiments.

FIG. 19 illustrates an automated hinged door on the incubator that can allow a dispensing head 1910 to interface with a consumable. The consumable device (within the incubator) is accessed by a dispensing head through the automation of hinged doors 1920 on the incubator. The hinged doors close to maintain the environment within the incubator and only open when the dispensing head must interface with the consumable device. The incubator can include a sanitization feature that destroys bacteria by increasing the temperature sufficiently. The sanitization procedure can be conducted without any consumables installed. The consumable rests on an optically clear substrate (such as optically clear acrylic, glass, and/or a similar substance). An optical imaging device below the glass substrate images cells within the microchambers using bright field or fluorescence microscopy. A ring of lights around the objective can provide a bright field-type illumination. This type of illumination can image all cells, regardless of whether they are stained. For fluorescent imaging, a xenon lamp can produce light, which is guided through tubing to the phototube. The phototube includes a select configuration of multiband filters to allow for the imagining of stained cells and of the capture agent substrate after incubation. The light passes through a single multiband excitation filter, a single multiband dichroic, and single multiband emission filter. The use of single filters allows for faster imaging, as single-band filters would need to be rotated into position.

There are many benefits to consolidating the emitted spectral range of the fluorophores that stain the cells with the emitted spectrum of the capture agent substrate. One benefit is the use of less stains to complete the entire workflow, which reduces complexity and cost. Multiband filters in the optical device also allow for the imaging of both cells and the capture agent substrate at a fast rate. The imaging device reduces complexity because it completes both imaging tasks, which were previously conducted by two separate expensive instruments: a fluorescence microscope and microarray scanner.

Figure 20:
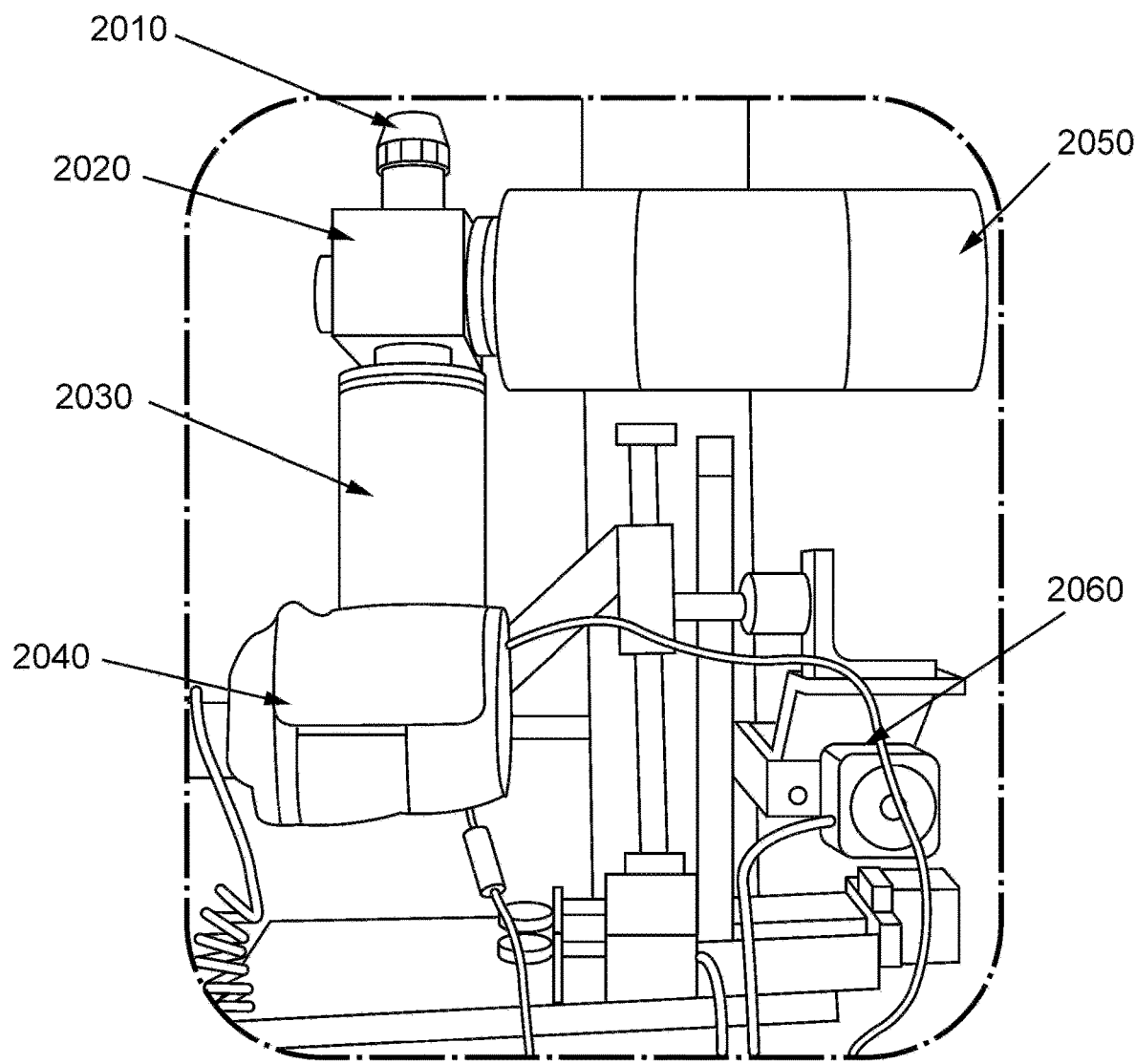
FIG. 20 is a diagram illustrating example optics for imaging isolated cells within microchambers and for imaging a secretion signal on a capture agent substrate, according to some embodiments.

FIG. 20 is a diagram illustrating example optics for imaging isolated cells within microchambers and for imaging a secretion signal on a capture agent substrate. A multi-axis stage 2060 moves the optics to the correct position for imaging. A light lamp 2050 produces light that is directed towards the multiband imaging filters 2020, which guide the light through the phototube 2030 and objective 2010. Reflected light from the image is passed through the multiband filters 2020, through the phototube 2030, and to the camera. A dichroic filter, within the filter assembly, separates the light from the lamp 2050 from the reflected light from the image. For example, in some embodiments, the multi-axis stage 2060 traverses laterally to image the plurality of consumables. The imaged can be focused by two mechanisms: a piezoelectric actuator that moves the objective; or a larger actuator which moves the entire imaging device in the up/down direction. The larger actuator would be mounted to the multi-axis stage.

In some embodiments, the imaging of samples as outlined above with reference to FIG. 20 using fluorescence imaging techniques may be complicated by the presence of glares from light sources and/or by the lack of uniformity of the illumination provided by the light sources. FIGS. 25-28, and the description thereof, disclose apparatus, methods and systems for microarray imaging of samples, and more particularly, apparatus, methods and systems for properly analyzing images of samples, for producing homogenous illumination of light sources on samples, and for reducing or removing glare from light sources applied onto samples.

FIG. 21 illustrates a view of the optical device beneath the incubator in the imaging position. The IsoPlexis optics including the objective 2120 can be mounted below the incubator. The optics move to the correct position to image cells or protein signal. The consumable device rests on an optically clear substrate 2110, which provides unobstructed vision for the imaging of the cell and secreted protein data, as shown in FIG. 15.

Figure 22B:
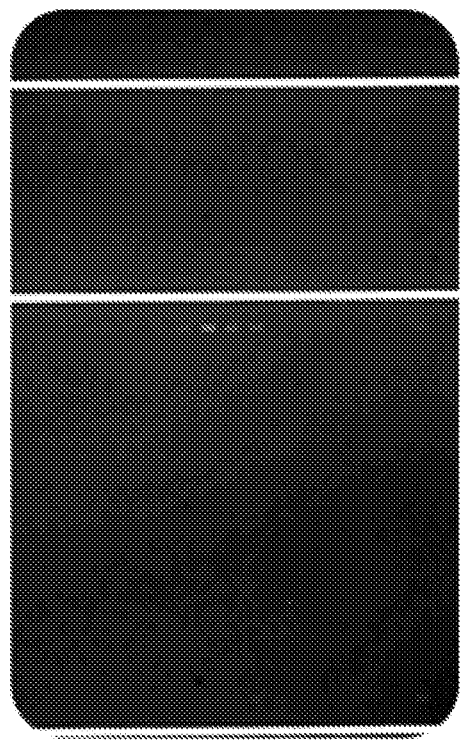
FIGS. 22A-C are diagrams illustrating an example image of a secretion signal from capture agent substrate, an example image of an alignment marker from a capture agent substrate, and an example image of stained cells within microchambers, respectively, according to some embodiments.
Figure 22A:
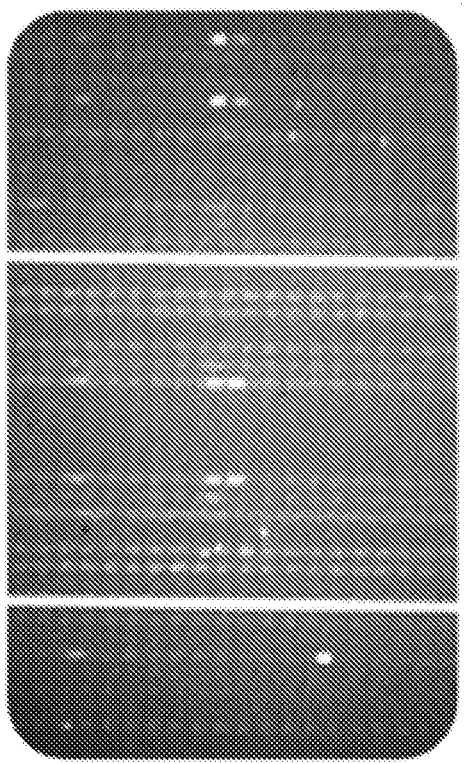
Figure 22C:
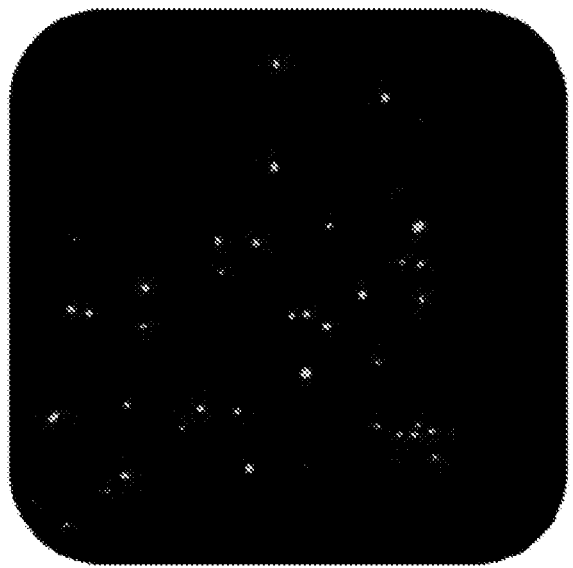

FIGS. 22A-C is a diagram illustrating an example image of a secretion signal from antibody encoded slide, an example image of an alignment marker from a capture agent substrate, and an example image of stained cells within microchambers. For example, the emitted spectral range of FIG. 22A shows a secretion signal from single-cells, which was captured by the antibody capture agents on the antibody encoded slide. The emitted spectral range of the FIG. 22B shows a fiducial, used for aligning the cell image with the secretion image (capture agent substrate). Specifically, FIG. 22B illustrates an alignment marker from the antibody encoded slide to allow for image processing software to spatially align the image of the cells with the image of the secreted protein signal. The fiducial is imaged with the cells and with the secretion image. The fiducial is used by software to spatially align the cell image with the secretion image for accurate representation of single cell secretion data. FIG. 22C shows stained cells within the microchambers. These cells may secrete proteins or lysed components (nucleic acids or proteins).

The automated instrument completes all biological tasks for the user. The user simply places their cell media onto the instrument, and the consumable devices into the incubation module. The consumable device design along with the integration of an incubator within the automated instrument eliminates liquid spills and the need for user skill.

Figure 23:
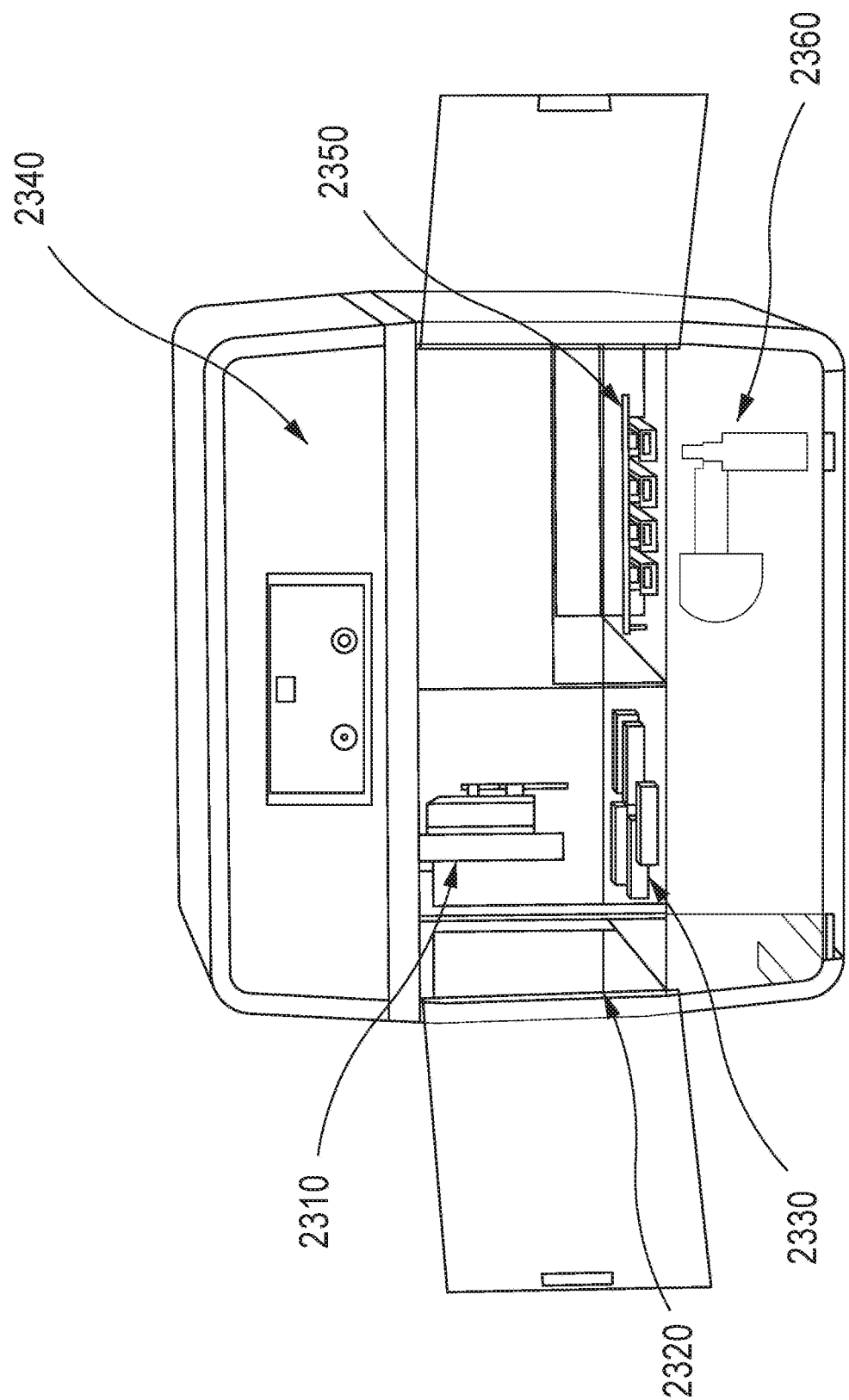
FIG. 23 is a diagram illustrating an example image of an automated instrument, according to some embodiments.

FIG. 23 is a diagram illustrating an example image of an automated instrument. For example, FIG. 23 illustrates an example rendered image of the entire automated instrument, which includes the incubator module 2350, the optical device 2360 beneath the incubator 2350, the liquid dispensing module 2310, the area for reagents 2330, and a simple user interface 2340. Consumable devices 2320 are placed into the incubator. The user places reagents on the deck of the device and the automated liquid handling head 2310 transfers the appropriate cells or reagents to the consumable devices. The IsoPlexis optics below the incubator traverse laterally to image cells and protein secretion data from within a plurality of consumable devices. The user controls the automated instrument through a user interface 2340.

Manual Consumable. In various embodiments, the device comprises a compression compartment used for a polyfunctional analysis assay such as disclosed assays. In a first step, cells may be located in microchambers on a microchamber substrate and capture agents may be located on a capture agent substrate. The microchamber substrate and capture agent substrate may be compressed together. A uniform and specific compression force may be used to ensure the glass slide seals and isolates the individual microchambers apart to eliminate cross-contamination. Alignment between the capture agent substrate and the microchambers on the microchamber substrate may be desirable for proper interaction between the antibodies and cells.

The reproducible positioning of the microchamber substrate in relation to the overall geometry of the compartment may be desirable for the microscopy imagining of the cells after clamping. Such configurations simplify user workflows during imaging and may reduce error. In various embodiments, the user may not adjust a microscope stage to accommodate slight adjustment in the position of the device.

In various embodiments, tools may not be used to achieve clamping. In various embodiments, the user can perform clamping, without experience with compressing the capture agent substrate to the microchamber substrate without clamping. After clamping, the compartment allows for microscopy of the microchambers and cells. Images without artifacts are desired to provide data on the maximum amount of microchambers and cells.

Figure 24A:
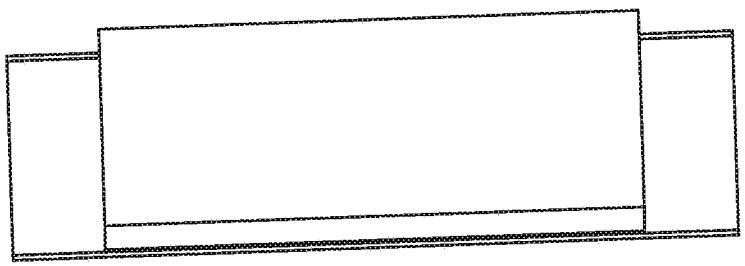
FIG. 24A is a diagram illustrating an example microchamber substrate on a glass slide, according to some embodiments.

FIG. 24A is a diagram illustrating an example microchamber substrate on a glass slide. For example, in various embodiments, a consumable assembly is described in conjunction with a compartment. For this consumable, a microchamber substrate may be secured or attached to a glass slide. A bond may be created between the glass slide and microchamber substrate by activating the surfaces through a plasma treatment process. See for a CAD image of the consumable.

The base of the compartment may be configured with features that allow the user to easily insert and remove the consumable. These features may be in the form of cutouts. The consumable may be located accurately to the base by features that limit the movement of the glass slide. A spring may be used to apply a nesting force on the glass slide for proper positioning and retention. Once the consumable is positioned on the base, the user can perform various cell loading procedures.

Figure 24B:
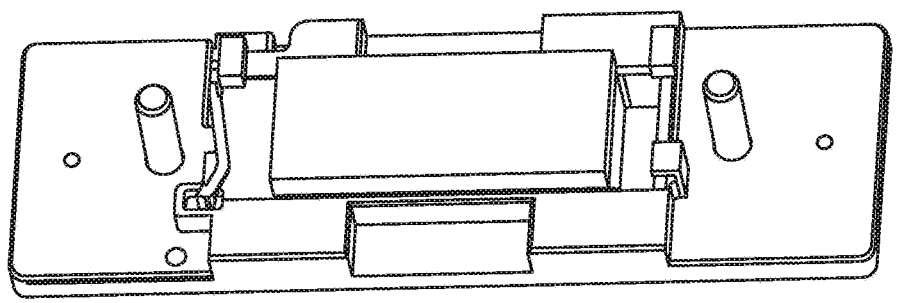
FIG. 24B is a diagram illustrating a base of an example compartment, according to some embodiments.
Figure 24C:
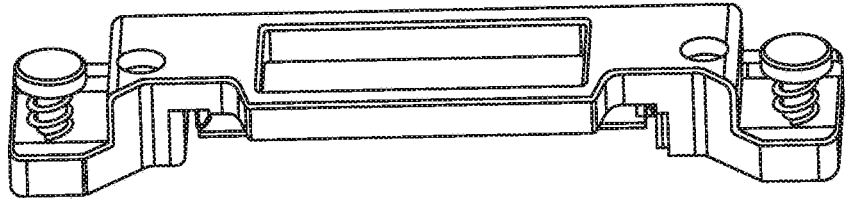
FIG. 24C is a diagram illustrating a top part of an example compartment with a capture antibody glass slide, according to some embodiments.

In various embodiments, the base may be configured with two shafts, which accurately guide the top of the compartment down onto the base. FIG. 24B is a diagram illustrating a base of an example compartment. FIG. 24C is a diagram illustrating a top part of an example compartment with a capture antibody glass slide. In various embodiments, the top of the compartment has features that allow the user to easily insert and remove the capture agent substrate. The capture agent substrate may be located accurately to the top by features that limit movement. Another spring may be used to apply a nesting force on the capture antibody glass slide for proper positioning. The top part features two bushings, which ride along the shafts of the base.

Figure 24D:
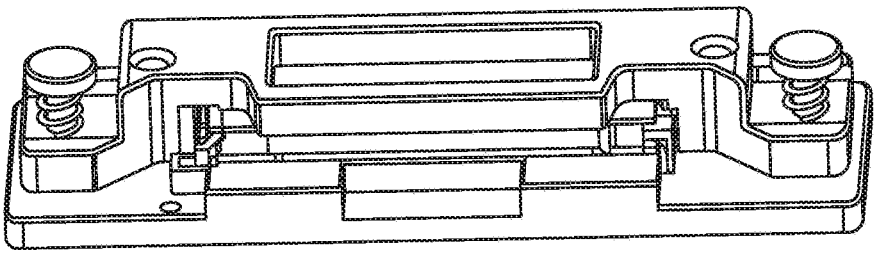
FIG. 24D is a diagram illustrating an example assembled compartment with engaged shoulder screws, according to some embodiments.

In various embodiments, to clamp, the top part is guided down toward the base by engaging the shafts and bushings. Shoulder screws are then engaged by the user with their fingers. When the shoulder screws are fully engaged, compression springs provide a uniform and magnitude specific compression force between the capture agent substrate and microchamber substrate. The magnitude specific compression force is repeatable and desirably does not place excessive stress on the capture agent substrate. This uniform and magnitude specific compression force helps ensure the capture agent substrate isolates the individual microchambers apart to eliminate cross-contamination. This compression force may be maintained throughout incubation or culturing of the disclosed assays. The cumulative benefit of positioning the consumable, capture agent substrate, and the shafts and bushings, is the ability to properly align the microchambers and antibodies. FIG. 24D depicts an assembled compartment with engaged shoulder screws, according to some embodiments. In the engaged position, cells are positioned within the microchambers and secreted proteins are introduced to the antibodies on the antibody encoded slide.

Openings in the top part and bottom part provide a pathway for light, which allows for bright field and fluorescent microscopy of the microchambers and cells. Microscopy may be improved by removing or eliminating material on either side of consumable and capture agent substrate. A feature on the base of the compartment allows the user to view a barcode, which may be affixed to the capture agent substrate.

The benefits of the clamping device disclosure include but are not limited to: tool-less operation for clamping; elimination of the need for user finesse; a design that yields repeatable results through clamping by different users; the ability to conduct microscopy with multiple fluorophores (cell stains); robustness for extended use; and the ability to perform a variety of cytokine response protocols.

The manual device performs similar clamping procedures as the automated instrument, and can involve user intervention. The user may bring the clamping device to a microscope for imaging. The device is then placed in an incubator. The capture agent substrate may then be manually cleaned and prepared with the appropriate reagents. The capture agent substrate can then be imaged with a microarray scanner.

As noted above, the imaging of samples using fluorescence imaging techniques may be complicated by the presence of glares from light sources and/or by the lack of uniformity of the illumination provided by the light sources. Disclosed herein are apparatus, methods and systems for microarray imaging of samples, and more particularly, apparatus, methods and systems for properly analyzing images of samples, for producing homogenous illumination of light sources on samples, and for reducing or removing glare from light sources applied onto samples.

In some embodiments, a camera may acquire an image of a dye-labelled sample (e.g., biological sample such as cells or tissues) when the sample fluoresces due to illumination by a light source (e.g., a laser). The graphical details of the sample depicted within the image, however, may depend on the color models used to interpret the colors captured by the image. A color model is a system that allows for the creation of a larger or full range of colors from a smaller set of primary colors. For example, red (R), green (G) and blue (B) can be combined in different manner to produce a wider spectrum of colors. In some embodiments, color models can be defined in a variety of ways, some examples of which include, but are not limited to, the so-called sRGB, ProPhoto RGB, Adobe 1998, wide gamut RGB, CIE XYZ, and/or the like. In some embodiments, the color models are available in post-processing programs (e.g., Adobe Photoshop), but can also be available when images are pre-processed in a "raw" state before algorithms have been used to make an interpretation of the colors in an image.

In some embodiments, as mentioned above, color images captured by a camera can be made up of three channels: red, green and blue (RGB). The intensities of each channel, however, may depend on the particular color model chosen for interpreting the colors of the image. The intensities may be represented by the so-called greyscale image that runs the gamut from completely black (representing weakest intensity) to completely white (representing strongest intensity). In some embodiments, the greyscale of each channel may be affected differently by different choices of color models. That is, in some embodiments, different color models may be used to assign higher or lower intensities to a channel. As such, by separating the channels from the color images to extract the greyscale images for one or more of the channels, varying intensities for each channel may be obtained, which is particularly useful for studying samples that may provide strongly contrasting signals.

For example, some signals from a sample fluorescence may be too weak to be picked up when a particular color model is used to interpret the color image of the sample while a choice of a different color model may capture the signals with at least adequate detail. Similarly, some signals may appear too strong or bright when interpreted using one color model, while a different color model may lessen the strength or brightness of the acquired signal and allow for more details to emerge that would have otherwise been concealed by the brightness.

Figure 25A:
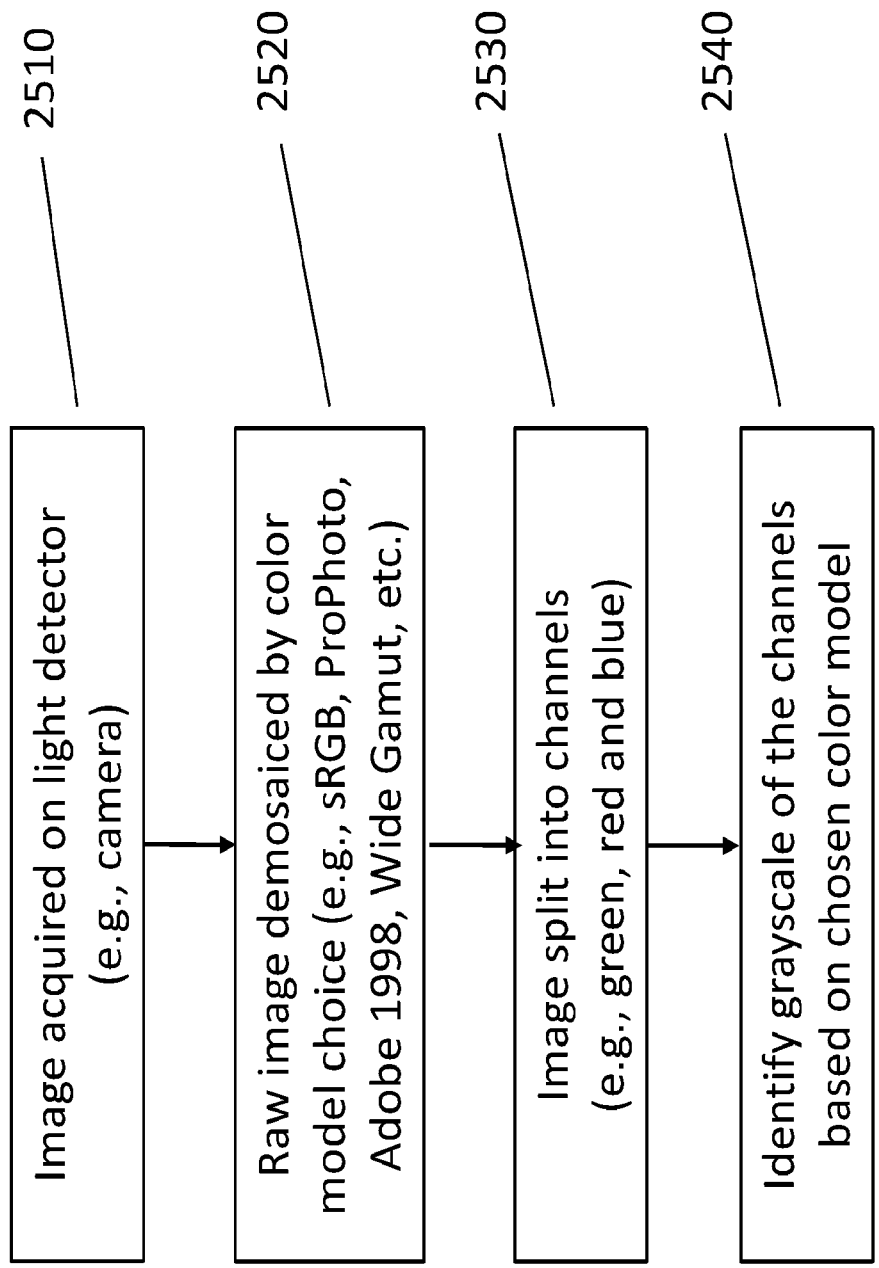
FIGS. 25A-B shows an example flowchart (FIG. 25A) illustrating the use of color models for controlling greyscale intensities in color channels, according to some embodiments.

With reference to FIG. 25A, in some embodiments, an example flowchart illustrating the use of color models for controlling greyscale intensities in color channels is shown.

Figure 25B:
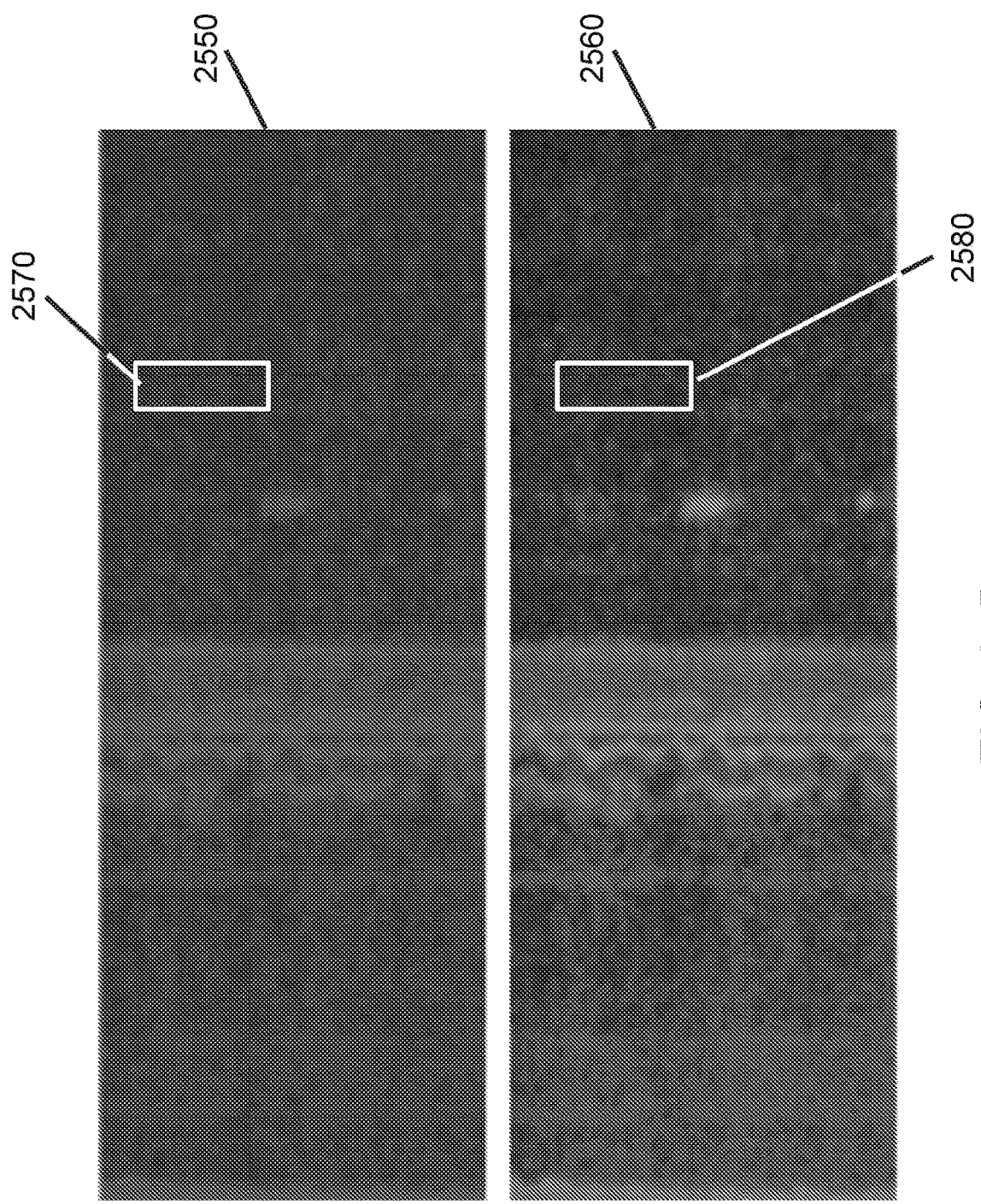

In some embodiments, an image acquired on camera, e.g., 2510, may be demosaiced by a choice of a color model, e.g., 2520. That is, in some embodiments, the mosaic raw image obtained by the camera is processed to obtain a full color version of the image, which may then further be split into channels, e.g., 2530. For example, the image may be split into red, green and blue channels. In some embodiments, the intensities or greyscale representations of each channel may vary based on the color model used, and as such, by varying the color model, different intensities may be obtained for each channel. In some embodiments, this may allow for, as discussed above, accurately capturing signals that may be on, or in the vicinity of, either extreme ends signal intensity (i.e., too weak or too strong) and which may have been difficult or even impossible to observe (for example, in some embodiments, the grayscale levels in a microarray image can be composed of overly faint and overly bright signals). By controlling for loss of signal at the highly dim and highly bright parts of images (e.g., where signals are near pure black and pure white on the greyscale), in some embodiments, potentially important sample information may be obtained. FIG. 25B shows an example specific implementation of the use of different color models (e.g., sRGB 2550 and ProPhoto 2560 color models) to control or assign different grayscale intensities to an image of a sample. Images 2550 and 2560 represent the same image of a sample that is demosaiced by different color models (sRGB and ProPhoto in the specific embodiments shown in FIG. 1B) and the images 2550 and 2560 have different grayscale intensities for same regions in the images 2550 and 2560 representing same portion of the sample. For example, the regions 2570 and 2580 have different grayscale intensities even though the two regions represent same portion of the sample (e.g., the grayscale intensity of region 2580 may be about two to three times as much as the intensity of region 2570 in the specific embodiment shown in FIG. 25B). In such embodiments, details that may be obscured due to the high or low intensities of one of the regions 2570 and 2580 may be enhanced and clarified in the other of the regions 2570 and 2580.

With reference to FIGS. 26A-D, in some embodiments, example schematic (FIG. 26A) and graphical (FIGS. 26B-D) illustrations showing the production of at least nearly homogenous illumination spots of a light source on a sample due to the use of a rotating disk are depicted. In some embodiments, a light source such as a laser may be used with the goal of producing a homogenous spot on some surface. In some embodiments, however, the laser may create a spot where the intensity of the light may vary across the extent of that spot. For example, the spot may comprise light and dark patterns, which may represent the lack of uniformity or homogeneousness. In some embodiments, diffusion filters can be used to reduce or eliminate the patterns and create the desired homogenous or at least nearly homogenous spot illumination. For example, these diffusion disks can be made from sandblasted glass to produce a frosted surface specifically for blurring and softening the light source, but many other means can also be used. In some embodiments, the diffusion disks may, however, include defects, which may then lead to the appearance of non-uniformity or non-homogeneity on the illumination spot due to the focusing of the defects on the spot by the highly focused and directed light from a laser. In some embodiments, the lack of uniformity caused by diffusion disk defects may be more pronounced than that generated by the laser itself. In such embodiments, a power source such as a motor may be used to rotate the diffusion disk such that the defects blend in together and the illumination spot appears uniform or homogenous. For example, the illumination spot may appear to be uniform or homogenous to the human eye. In some instances, the illumination spot may appear to be uniform or homogenous when an image is taken and analyzed via, for example, an image analysis software.

Figure 26A:
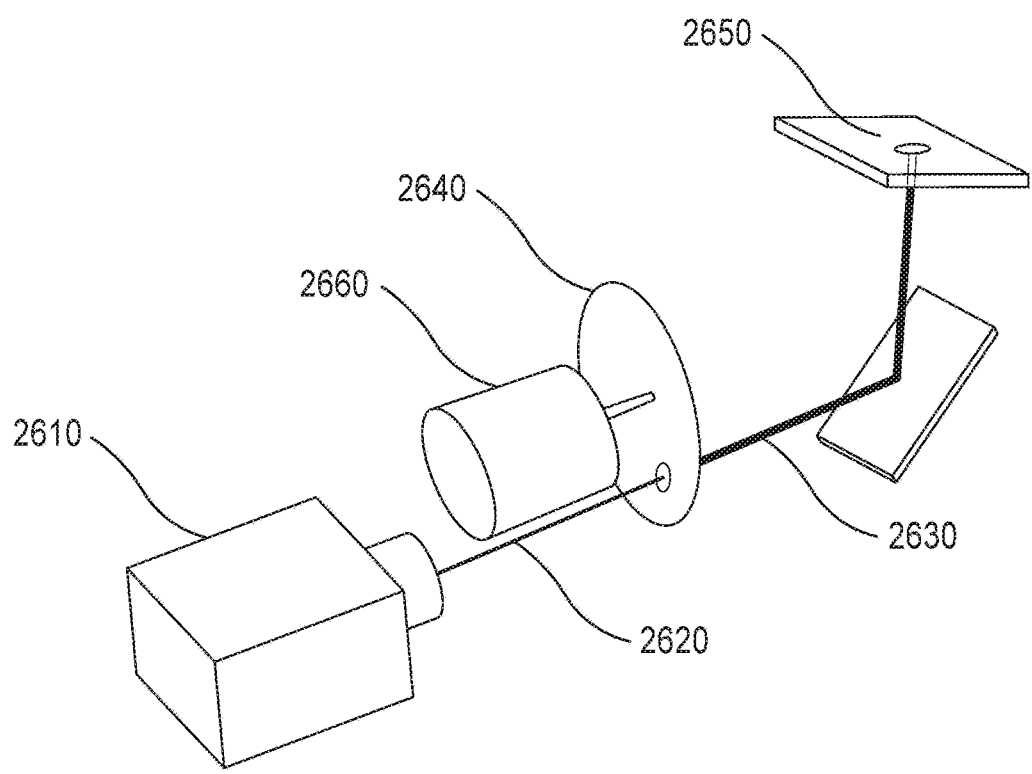
FIGS. 26A-D show example schematic (FIG. 26A) and graphical (FIGS. 26B-D) illustrations of the production of homogenous illumination spots on a sample due to the use of a rotating disk, according to some embodiments.
Figure 26B:
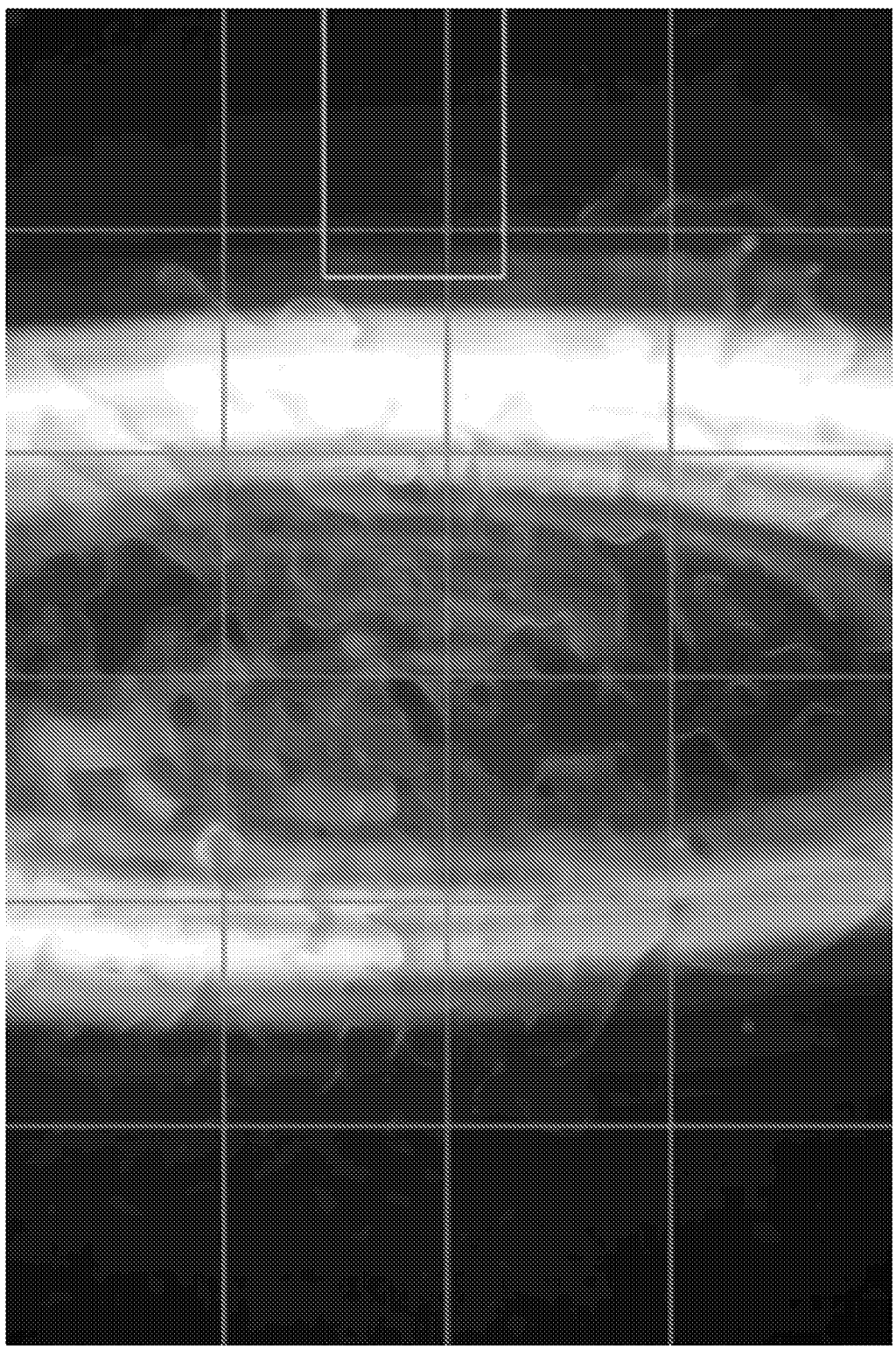
Figure 26C:
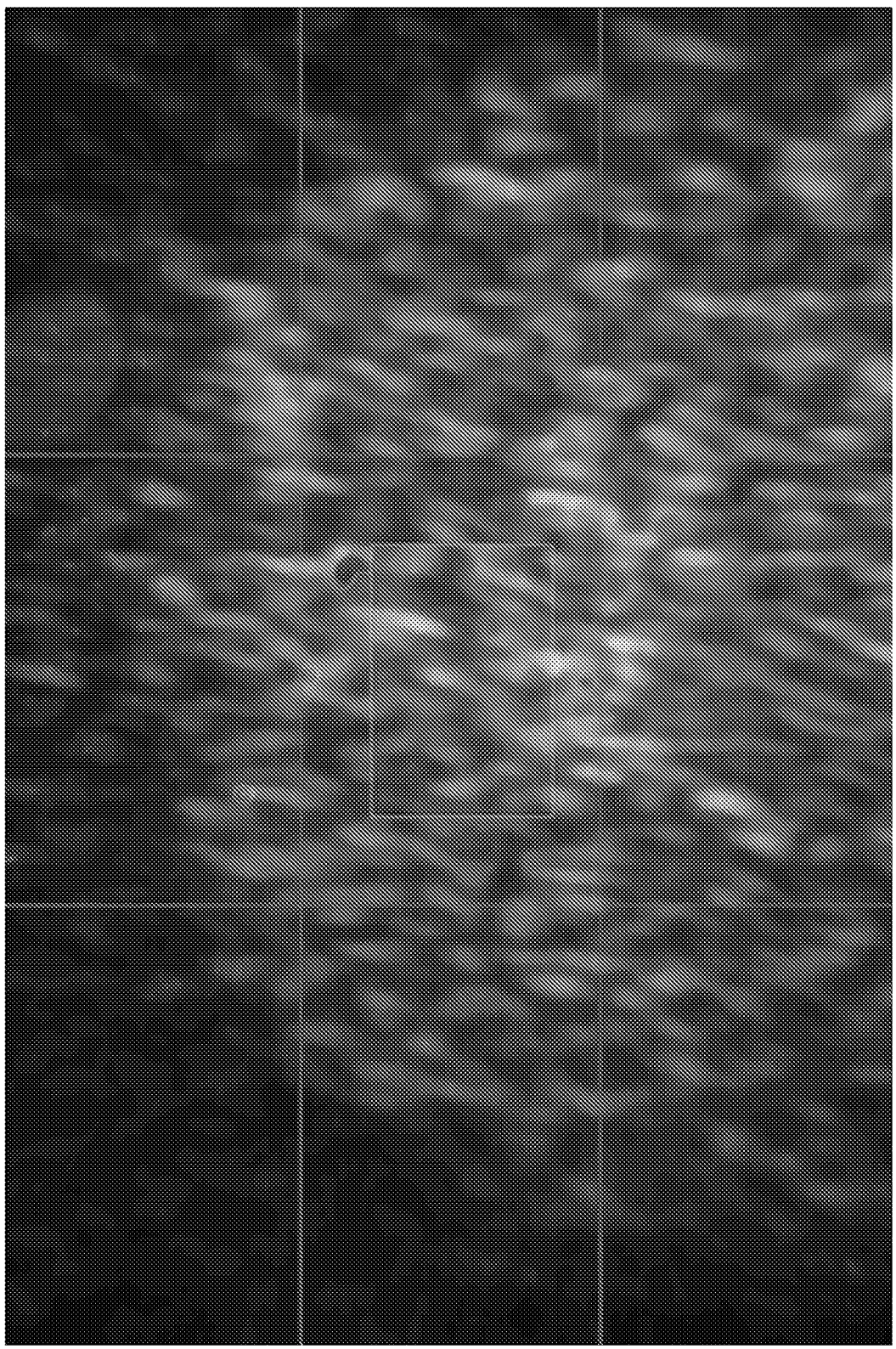
Figure 26D:
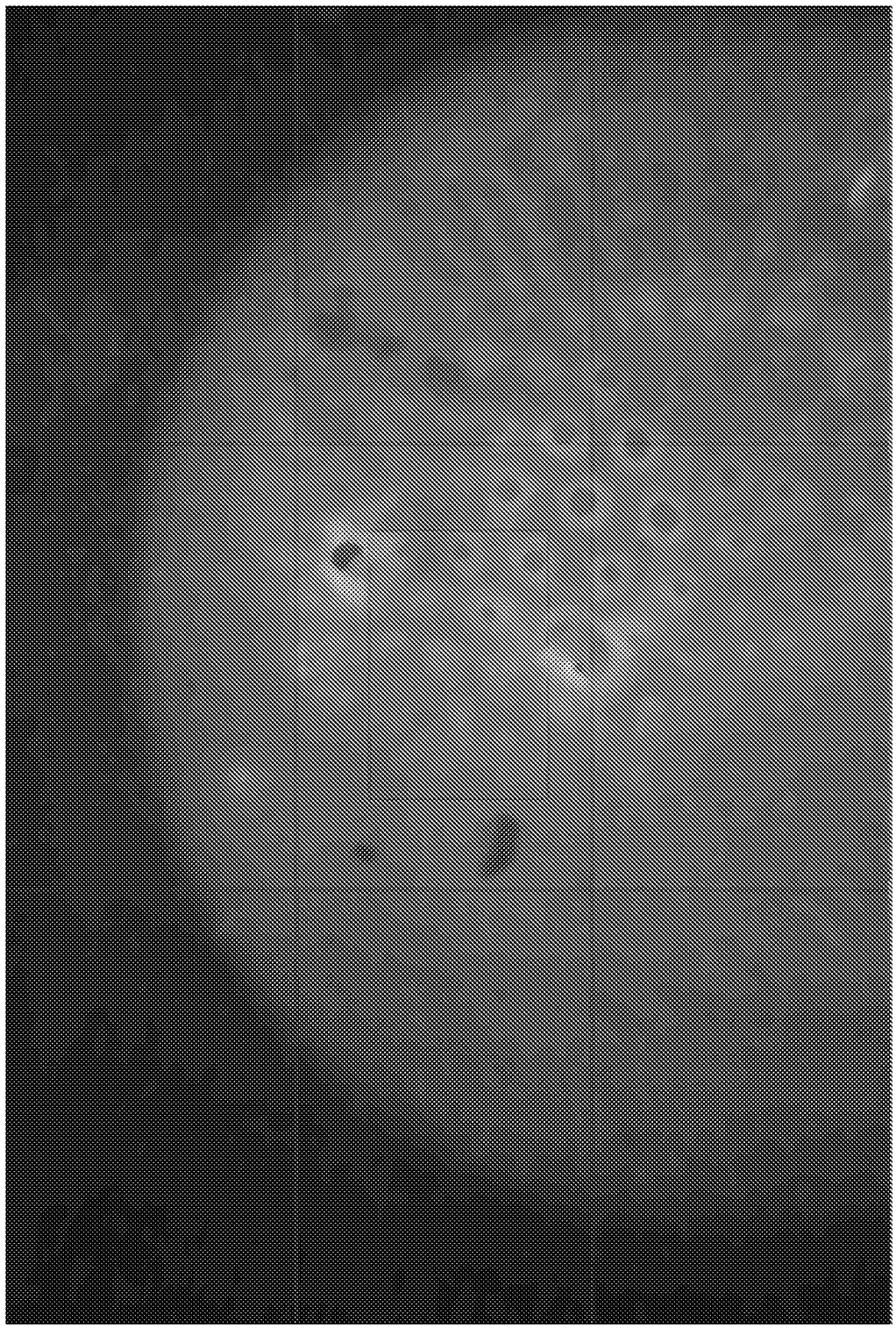

For example, when laser source 2610 emits a focused laser beam 2620, in some embodiments, the laser beam may not entirely be uniform and the non-uniformity may show in the illumination spot 2650. In some embodiments, the diffusion disk 2640 may itself contain defects (e.g., when the disk 2640 is treated to reduce or eliminate the illumination spot patterns caused by the laser) and these defects may cause the focused laser beam 2620 to become a less focused and diffused beam 2630 that is non-uniform and thus exacerbate the lack of uniformity at the illumination spot 2650. In some embodiments, a motor 2660 may be employed to rotate the diffusion disk 2640 which may result in the illumination spot appearing as uniform or homogenous. In some embodiments, the rotation speed may exceed about 25 rpm, about 30 rpm, about 40 rpm, about 50 rpm, about 60 rpm, about 75 rpm, about 80 rpm, including values and subranges therebetween. In some embodiments, the rotation speed may be in the range from about 50 rpm to about 300 rpm, from about 50 rpm to about 200 rpm, from about 50 rpm to about 150 rpm, from about 50 rpm to about 100 rpm, including values and subranges therebetween. FIGS. 26B-D show a specific example implementation of the use of a rotating diffusion disk 240 to create an illumination spot that is more uniform or homogenous (FIG. 26D) compared to when the diffusion disk 240 is not rotating (FIG. 26C). FIG. 26B shows an example embodiment where the laser spot itself has patterns (i.e., it is non-homogenous). In some embodiments, the beam may have any of circular, elliptical or rectangular shapes.

Figure 27:
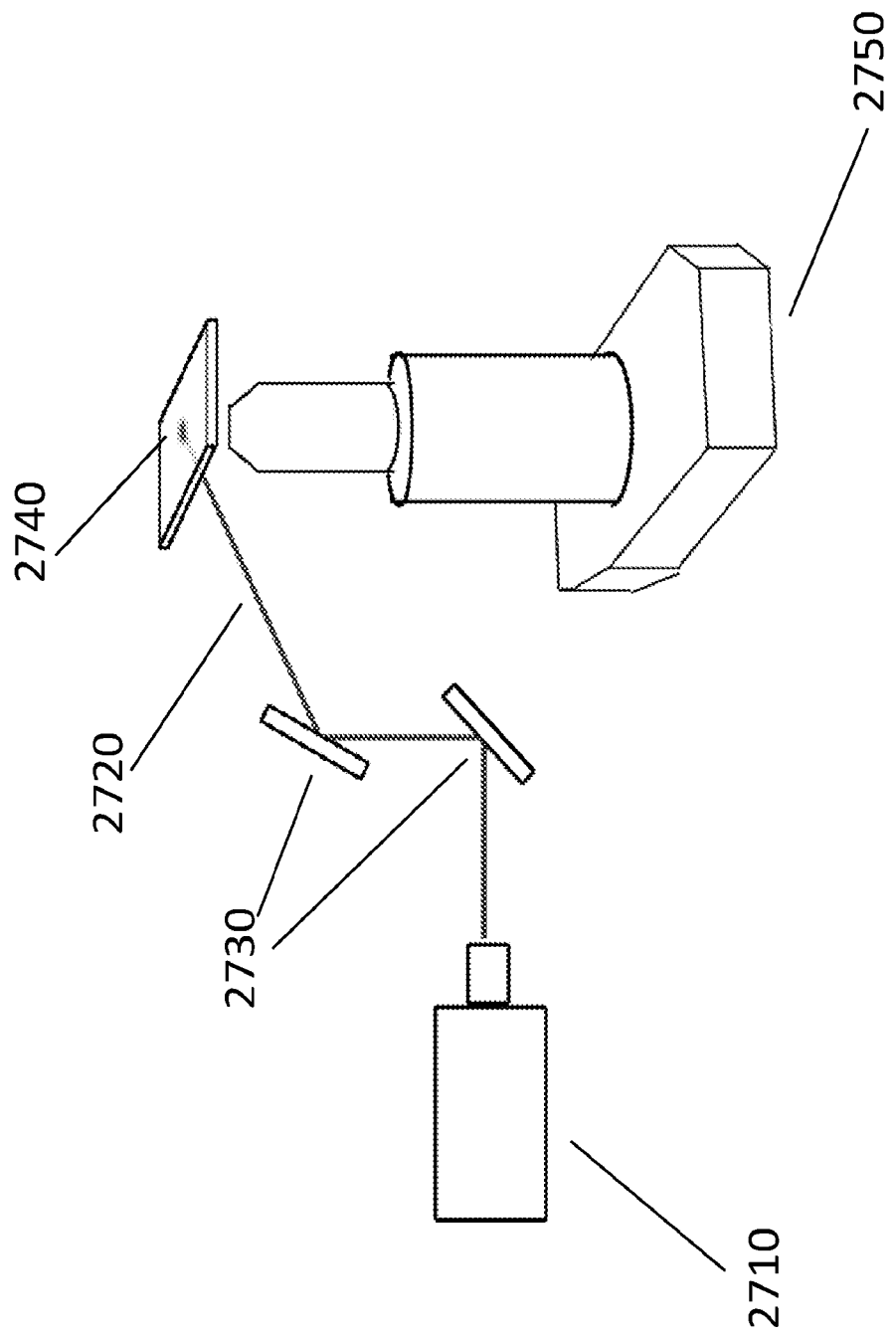
FIG. 27 shows an example set-up of a widefield microscope for studying a sample including a light source directly projected onto the sample, according to some embodiments.

With reference to FIG. 27, in some embodiments, an example set-up of a widefield microscope for studying a sample including a light source directly projected onto the sample is shown. In some embodiments, when imaging a sample (e.g., biological samples such as cells, tissues, etc.) on a microarray, the samples may be labelled with a dye and the fluorescence that is released by the sample when illuminated by a light source such as a laser can be detected by a light detector (e.g., camera). In some embodiments, the light from the light source may reflect off a mirror that is angled at about 45° with respect to the path of the light to be reflected towards the sample. An example of such a mirror is a dichroic mirror that is coated (e.g., double layer coating) such that it allows certain wavelengths of light through while blocking the passage of others. In some embodiments, an excitation filter may also be used to filter out undesirable wavelengths from the laser light before the laser light strikes the dichroic mirror. The dichroic mirror and/or the excitation filter, however, may cause illumination issues such as reduction of the power or intensity of the light and/or glare (e.g., within the structures that hold the optical components, an example of which includes the filter cube). In some embodiments, such issues may be resolved or reduced by projecting light (e.g., laser) onto the sample itself. In some embodiments, such projection may occur in the presence of the dichroic mirror and/or the excitation filter, while in others, it may occur in the absence of the dichroic mirror and/or the excitation filter. The latter embodiments include instances where a single wavelength laser system is used (that is, there may be no need for wavelength filtering). Other instances include situations where when using a single laser once a time, the excitation wavelength could be far away enough to the fluorescent wavelength (obviating the need for the camera to use a filter). As an additional example, an excitation wavelength that is not sensitive by the camera, such as UV, may also be used.

In some embodiments, the projection may be aided by lenses and/or filters located between the sample and the light source, the locations being such that the above-noted issues such as glare are at least reduced if not eliminated. Further, when the light source is a laser, in some embodiments, the nature of the light may provide better edge detail in samples and potentially greater contrast. In some embodiments, such projected light set-ups to image or study samples may also be used, besides for microarray imaging or scanning as mentioned above, in high magnification microscopes (e.g., compound microscopes), and/or the like. In some embodiments, the set-up may also be used in lower magnification microscopes such as stereo or dissection microscopes. In some embodiments, the projected light system and/or method discussed above can be different from the microscopy method known as total internal reflection fluorescence where evanescent wave from a totally internally reflected incident light illuminates the sample and causes the sample to fluoresce. With reference to the projected light method discussed herein, however, little or no total internal reflection may occur when the laser light illuminates the sample. In such embodiments, the sample may fluoresce as a result of illumination by the incident light itself, as opposed to any evanescent wave. In some embodiments, however, the fluorescence from a sample may be from both the projected light and any evanescent wave that may have been generated due to total internal reflection.

FIG. 27 shows an example set up where light from a light source 2710 such as a laser is projected onto a sample location 2740 with the aid of mirrors 2730 and other components such as lenses, filters, etc. (not shown). Such a set-up includes the situation where the light path (the path the light takes after being emitted by the light source 2710) and the imaging path (the path leading into the light detector 2750) may not entirely intersect and as such facilitate the reduction or elimination of illumination issues such as glare. In some embodiments, such a set-up may also aid in reducing or eliminating reduction in the power or intensity of the light impinging onto the sample. For example, in some embodiments, the light may be directly applied to the sample without the aid of other components such as mirrors and filters and in such embodiments, there can be little if no reduction in the power or intensity of the light illuminating the sample.

Figure 28:
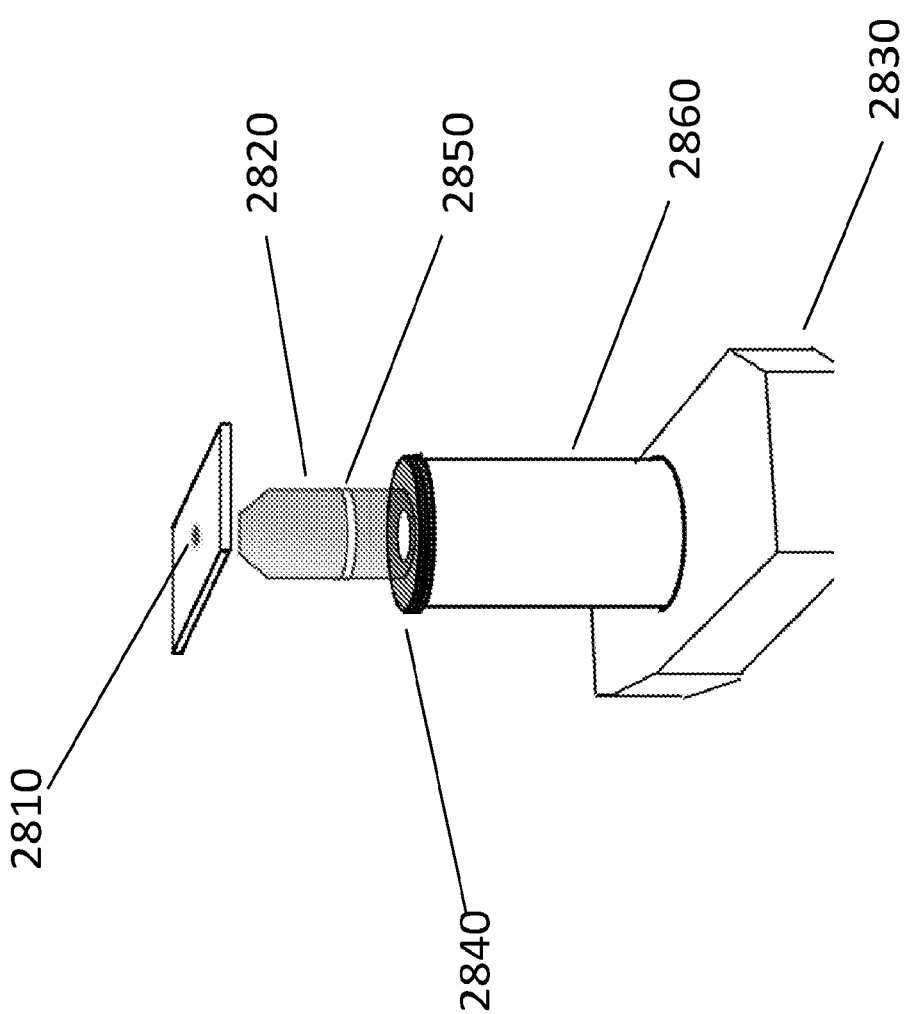
FIG. 28 shows an example schematic of a widefield microscope with an aperture configured for removing or reducing glare from a light source, according to some embodiments.

As mentioned above, illumination issues such as glares may be undesirable when performing microarray imaging or scanning and one may wish to reduce if not eliminate such issues. In some embodiments, an aperture may be used for removing or reducing glare from a light source in widefield compound microscopes, and FIG. 28 shows an example illustration of such a microscope. In some embodiments, an aperture or a pinhole 2840 may be situated in between the lens (also known as the objective) 2820 and the light detector (e.g., camera) 2830 so as to filter out glare when performing an imaging or scanning of the sample 2810. In some embodiments, the aperture may be fixed in size (e.g., radius, diameter, etc.), while in others it may be adjustable in size.

With reference to FIG. 28, in some embodiments, the light causing the fluorescence by the sample 2810 may be a projected light, such as the set-up shown in FIG. 27. In some cases, other set-ups may be used as well. In some embodiments, the aperture or pinhole 2840 may be located "downstream" from the lens or objective 2820. That is, the aperture 2840 may be located after the lens 2820 along the path the light takes from the sample 2810 to the light detector 2830. In such embodiments, any other aperture may not be located along the light path between the light source (not shown) and the lens 2830 and/or between the sample 2810 and the lens 2820. In some instances, the light source (not shown) can be an LED. In some embodiments, an additional illumination source, such as a collimated LED, could be used for microchamber identification. In some embodiments, the aperture 2840 may be the only aperture in the imaging or scanning system or microscope of FIG. 28 that includes the aperture 2840. In some embodiments, the imaging or scanning system or microscope of FIG. 28 may not include a mirror angled at about 45° with respect to the path of the light and configured to filter out at least some wavelengths of the light. For example, the system or microscope may be configured such that there is a direct "line of sight" between the sample 2810, the lens 2820, other components such as a filter 2850, the aperture 2840, possible additional optics 2860 and the light detector 2830 without the presence of a mirror (a dichroic mirror or otherwise) along this "line of sight." In some embodiments, as discussed above, there may not be another aperture along this line of sight or there may not be an aperture along the "line of sight" running from the sample 2810 to the lens 2820.

Any and all references to publications or other documents, including but not limited to, patents, patent applications, articles, webpages, books, etc., presented in the present application, are herein incorporated by reference in their entirety.

Accordingly, exemplary embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements. In other words, elements from one or another disclosed embodiment may be interchangeable with elements from other disclosed embodiments, thereby supporting yet other embodiments. Still other embodiments are possible with embodiments disclosed herein (or features thereof) combined with embodiments disclosed in the related applications and/or references incorporated by reference, or combined with elements/features/functionality of the embodiments from the incorporated by reference. In addition, one or more features/elements of disclosed embodiments may be removed and still result in patentable subject matter (and thus, resulting in yet more embodiments of the subject disclosure). Certain embodiments may be patentable over the prior art for specifically lacking one or more elements, features, and/or functionality of that disclosed in the prior art. Accordingly, claims directed to such distinguishing embodiments (among the many embodiments disclosed herein) may include one or more negative limitations.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in some embodiments, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in some embodiments, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, the term "about" when used in conjunction with numerical values and/or ranges generally refers to those numerical values and/or ranges near to a recited numerical value and/or range. In some instances, the term "about" can mean within ±10% of the recited value. For example, in some instances, "about 100 [units]" can mean within ±10% of 100 (e.g., from 90 to 110).

The invention claimed is:

1. An apparatus configured to analyze substances expressed by a biological cell, the apparatus comprising:
    a first compressible substrate comprising:
        a length extending in a first direction, a first end and a second end separated by the length, and a width extending in a second direction;
        a compressible material including a plurality of microchambers molded in the compressible material, the plurality of microchambers having an open side and configured to receive a biological cell, each microchamber having a width extending in the second direction, a length extending in the first direction, and a depth; and
    a second substrate configured for reversible sealing attachment with the first substrate, the second substrate including an array of approximately linear and parallel, isolated capture areas (CAs) extending in the second direction, each CA having a predetermined width, wherein each CA comprises a specific capture antibody;
    wherein upon attachment of the second substrate with the first compressible substrate:
        an assembly is formed such that the open side of the plurality of chambers is covered by the second substrate and a cavity is established between the first compressible substrate and the second substrate,
        the cavity is configured to receive a sample comprising a plurality of biological cells;
        upon compressing the first compressible substrate against the second substrate, each micro-chamber is reversibly sealed with the second substrate and traps a single cell from the plurality of biological cells of the sample received,
        and
        a portion of each of the plurality of CAs are exposed in each of the chambers.

2. The apparatus of claim 1, further comprising a compression compartment for housing the assembly.

3. The apparatus of claim 2, wherein the compression compartment comprises compression means configured to compress the assembly.

4. The apparatus of claim 2, wherein a base of the compartment is configured with one or more features that allow easy insertion and removal of the apparatus.

5. The apparatus of claim 4, wherein the one or more features comprise a cutout.

6. The apparatus of claim 4, wherein the base is configured with at least one shaft, the at least one shaft is configured to accurately guide a top of the compartment onto the base.

7. The apparatus of claim 6, further comprising shoulder screws configured for hand manipulation by a user.

8. The apparatus of claim 6, further comprising one or more compression springs, and wherein upon fully engaging respective shoulder screws associated therewith, the one or more compression springs provide a uniform and/or magnitude specific compression force between the second substrate and first substrate.

9. The apparatus of claim 8, wherein the magnitude specific compression force is configured to be repeatable and/or not place excessive stress on the second substrate.

10. The apparatus of claim 2, wherein the compression compartment includes a spring.

11. The apparatus of claim 2, wherein the compression compartment includes a clamp.

12. The apparatus of claim 2, further comprising one or more openings configured for providing a pathway for light.

13. The apparatus of claim 2, further comprising a feature on a base of the compartment configured to enable viewing one or more CAs of the second substrate.

14. The apparatus of claim 1, wherein the first substrate is secured, bonded or attached to the second substrate.

15. The apparatus of claim 14, wherein the bond is established between the second substrate and first substrate by activating corresponding mating surfaces of each substrate.

16. The apparatus of claim 15, wherein activating of mating surfaces comprises plasma treatment.

17. The apparatus of claim 1, wherein the first substrate comprises silicone.

18. The apparatus of claim 1, wherein the second substrate comprises a glass substrate.

* * * * *

UNITED STATES PATENT AND TRADEMARK OFFICE
CERTIFICATE OF CORRECTION

| | | |
|---|---|---|
| PATENT NO. | : 11,525,783 B2 | Page 1 of 1 |
| APPLICATION NO. | : 16/463333 | |
| DATED | : December 13, 2022 | |
| INVENTOR(S) | : Tsiomplikas et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 246 days.

Signed and Sealed this
Thirty-first Day of December, 2024

Derrick Brent
*Acting Director of the United States Patent and Trademark Office*